US008116551B2

(12) United States Patent
Gallagher et al.

(10) Patent No.: US 8,116,551 B2
(45) Date of Patent: Feb. 14, 2012

(54) METHOD AND SYSTEM FOR IMAGE ANALYSIS

(75) Inventors: William Gallagher, Rathgar (IE); Elton Rexhepaj, Terenure (IE); Donal Brennan, Portobello (IE)

(73) Assignee: University College, Dublin, National University of Ireland, Dublin (IE)

( * ) Notice: Subject to any disclaimer, the term of this patent is extended or adjusted under 35 U.S.C. 154(b) by 54 days.

(21) Appl. No.: 12/746,165

(22) PCT Filed: Dec. 4, 2008

(86) PCT No.: PCT/IE2008/000119
§ 371 (c)(1),
(2), (4) Date: Jun. 3, 2010

(87) PCT Pub. No.: WO2009/072098
PCT Pub. Date: Jun. 11, 2009

(65) Prior Publication Data
US 2010/0254589 A1    Oct. 7, 2010

(30) Foreign Application Priority Data
Dec. 4, 2007  (IE) .................................. S2007/0882

(51) Int. Cl.
*G06K 9/00* (2006.01)
(52) U.S. Cl. ......................... 382/133; 382/128; 382/162
(58) Field of Classification Search .................. 382/100, 382/128, 133, 164, 173
See application file for complete search history.

(56) References Cited

U.S. PATENT DOCUMENTS

| 5,828,776 | A | 10/1998 | Lee et al. | |
| 7,796,815 | B2* | 9/2010 | Muschler et al. | 382/173 |
| 2003/0002737 | A1 | 1/2003 | Bankman et al. | |
| 2004/0114800 | A1* | 6/2004 | Ponomarev et al. | 382/173 |
| 2005/0075537 | A1 | 4/2005 | Chen et al. | |
| 2006/0072804 | A1 | 4/2006 | Watson et al. | |
| 2006/0280352 | A1* | 12/2006 | Muschler et al. | 382/133 |
| 2009/0129671 | A1* | 5/2009 | Hu et al. | 382/173 |
| 2009/0129673 | A1* | 5/2009 | Simon et al. | 382/173 |

FOREIGN PATENT DOCUMENTS

WO     WO 96/09606       3/1996
WO     WO 2005/091203    9/2005

OTHER PUBLICATIONS

Barnes et al., "Immunohistochemical Determination of Oestrogen Receptor: Comparison of Different Methods of Assessment of Staining and Correlation with Clinical Outcome of Breast Cancer Patients," British Journal of Cancer, vol. 74, pp. 1445-1451 (1996).

(Continued)

*Primary Examiner* — Stephen Koziol
(74) *Attorney, Agent, or Firm* — Hunton & Williams LLP

(57) ABSTRACT

The present invention relates generally to a method for determining the level of expression of one or more candidate objects of interest in a biological sample. In particular, the present invention relates to a method for determining the level of expression of one or more candidate objects of interest using image analysis. More specifically, the present invention relates to a method and a system for determining the level of expression of one or more candidate objects of interest using an automated (computer-aided) image analysis system.

15 Claims, 61 Drawing Sheets

OTHER PUBLICATIONS

Camp et al., "Automated Subcellular Localization and Quantification of Protein Expression in Tissue Microarrays," Nature Medicine, vol. 8, pp. 1323-1328 (2002).

Cross, "Observer Accuracy in Estimating Proportions in Images: Implications for the Semi Quantitative Assessment of Staining Reactions and a Proposal for a New System," Journal of Clinical Pathology, vol. 54, pp. 385-390 (2001).

Fernandez et al., "Infrared Spectroscopic Imaging for Histopathologic Recognition," Nature Biotechnology, vol. 24, pp. 469-474 (2005).

Lehr et al., "Quantitative Evaluation of HER2/neu Status in Breast Cancer by Fluorescence In Situ Hybridization and by Immunohistochemistry With Image Analysis," American Journal of Clinical Pathology, vol. 115, pp. 814-822 (2001).

O'Brien et al., "CENP-F Expression is Associated with Poor Prognosis and Chromosomal Instability in Patients with Primary Breast Cancer," International Journal of Cancer, vol. 120, pp. 1434-1443 (2007).

Rexheepaj et al., "Novel Image Analysis Approach for Quantifying Expression of Nuclear Proteins by Immunohistochemistry: Application to Measurement of Oestrogen and Progesterone Receptor Levels in Breast Cancer," Breast Cancer Research, vol. 10, No. 5, pp. 1-10 (2008).

Shi et al., "Tumor Classification by Tissue Microarray Profiling: Random Forest Clustering Applied to Renal Cell Carcinoma," Modern Pathology, vol. 18, pp. 547-557 (2005).

International Search Report for International Application No. PCT/IE2008/000119 mailed Mar. 23, 2009.

Written Opinion for International Application No. PCT/IE2008/000119 mailed Mar. 23, 2009.

* cited by examiner

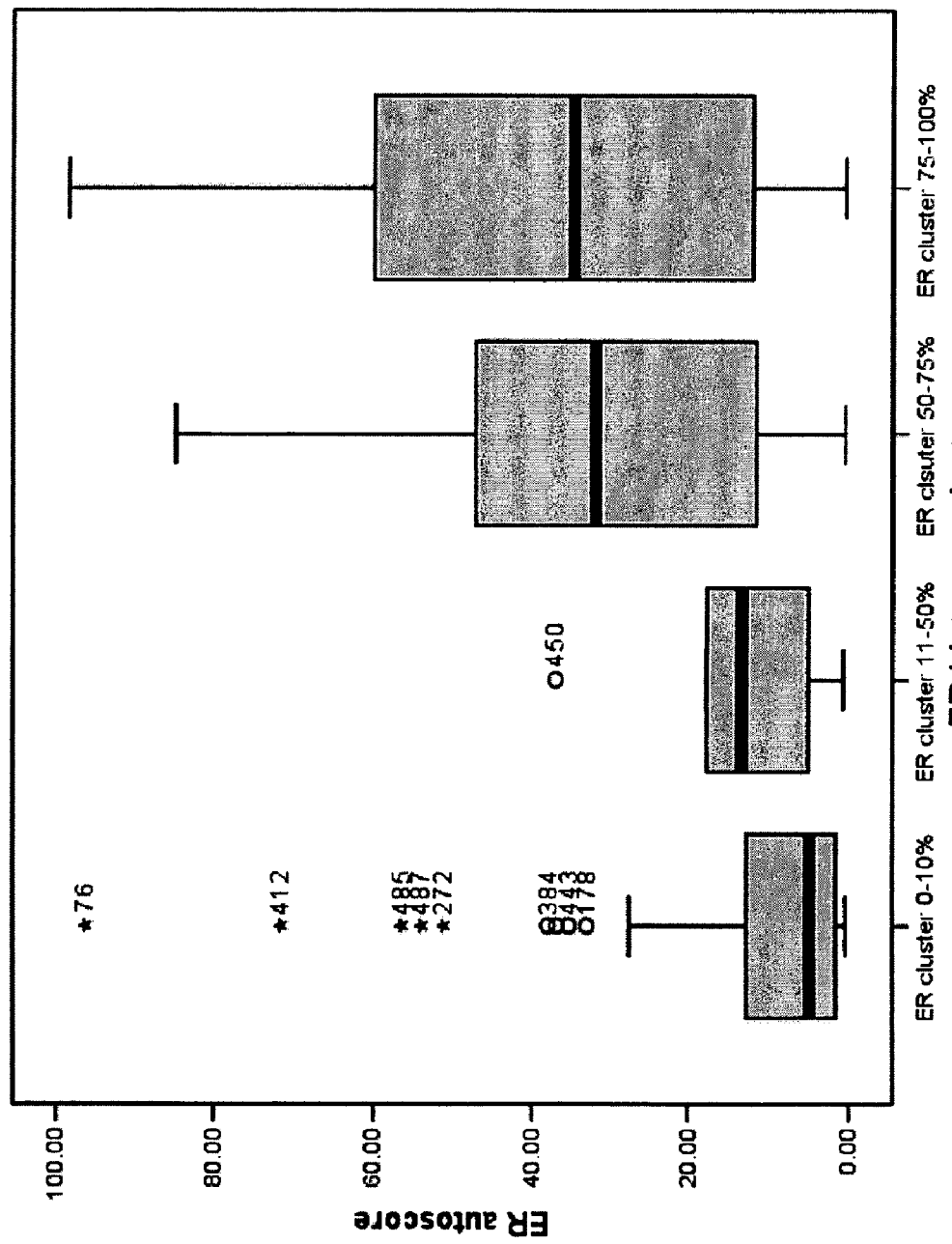

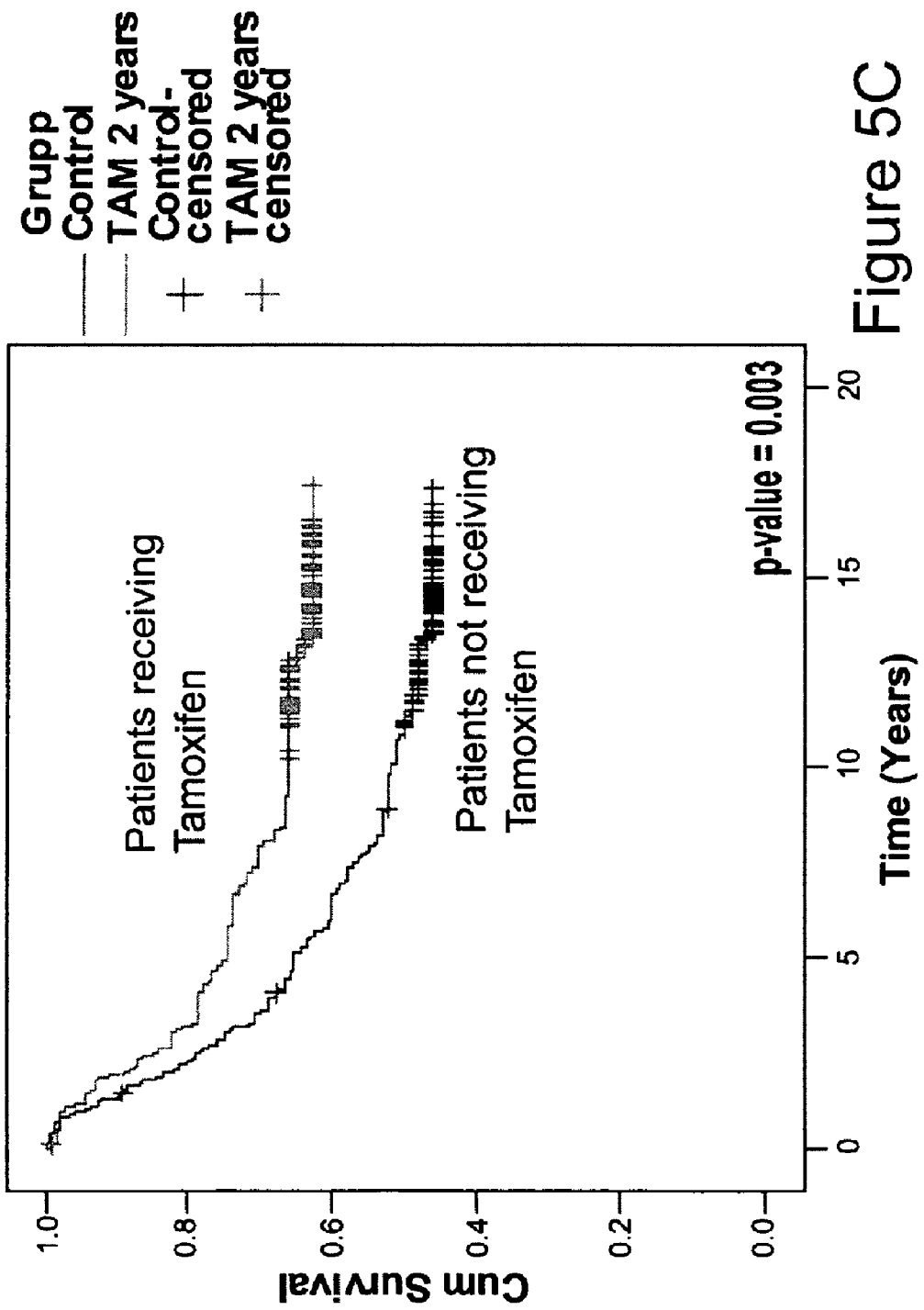

1) Separation of DAB from Haematoxylin

> Representative tumour nuclear DAB negative patterns are selected and converted into LUV colour space

⬇

> Mean L levels for each pattern are computed based on the images selected above

⬇

> Based on the thresholds defined above DAB is separated from Haematoxylin

⬇

> Tissue is separated from slide background using a set of RBB thresholds optimised for IHC and the Aperio scanner

⬇

> RGB values of Haematoxylin positive pixels are converted in the HSV colour space to separate connective tissue from nuclear negative staining

Figure 7A

2) Segmentation of all nuclear patterns

> Convert image from RGB to CIE LUV uniform colour space and then convert the luminance channel (L) to gray level

⬇

> Adjust contrast of the gray level representation above

⬇

> Apply mean shift segmentation to separate nuclear staining from background cytoplasmic staining.

⬇

> Extract gray level values of pixels isolated above

⬇

> Adjust contrast of the gray level representation above

⬇

> Apply watershed segmentation to identify all nuclei

Figure 7B

Extraction of DAB positive nuclei and their morphological and spatial properties 1) Find for each DAB positive nuclei:
- X, Y position in the image
- Area
- The small and big axis of the outbound ellipse

Measure the distance between each nuclei and its neighbours

2) Nuclei-to-nuclei distances are clustered in two groups:
- Distances of nuclei belonging to nuclei part of the same tumor gland (cluster D1)
- Distances of isolated nuclei or nuclei part of different tumor glands (cluster D2)

Identify nuclei part of cluster D1 and discard nuclei in cluster D2

3) From the nuclei identified above the following features are extracted:
Mean area (MAP), mean length of small and big axis, mean (MDN) and max nuclei-to-nuclei distance, total number of nuclei and mean intensity of DAB positive nuclei

Figure 8A

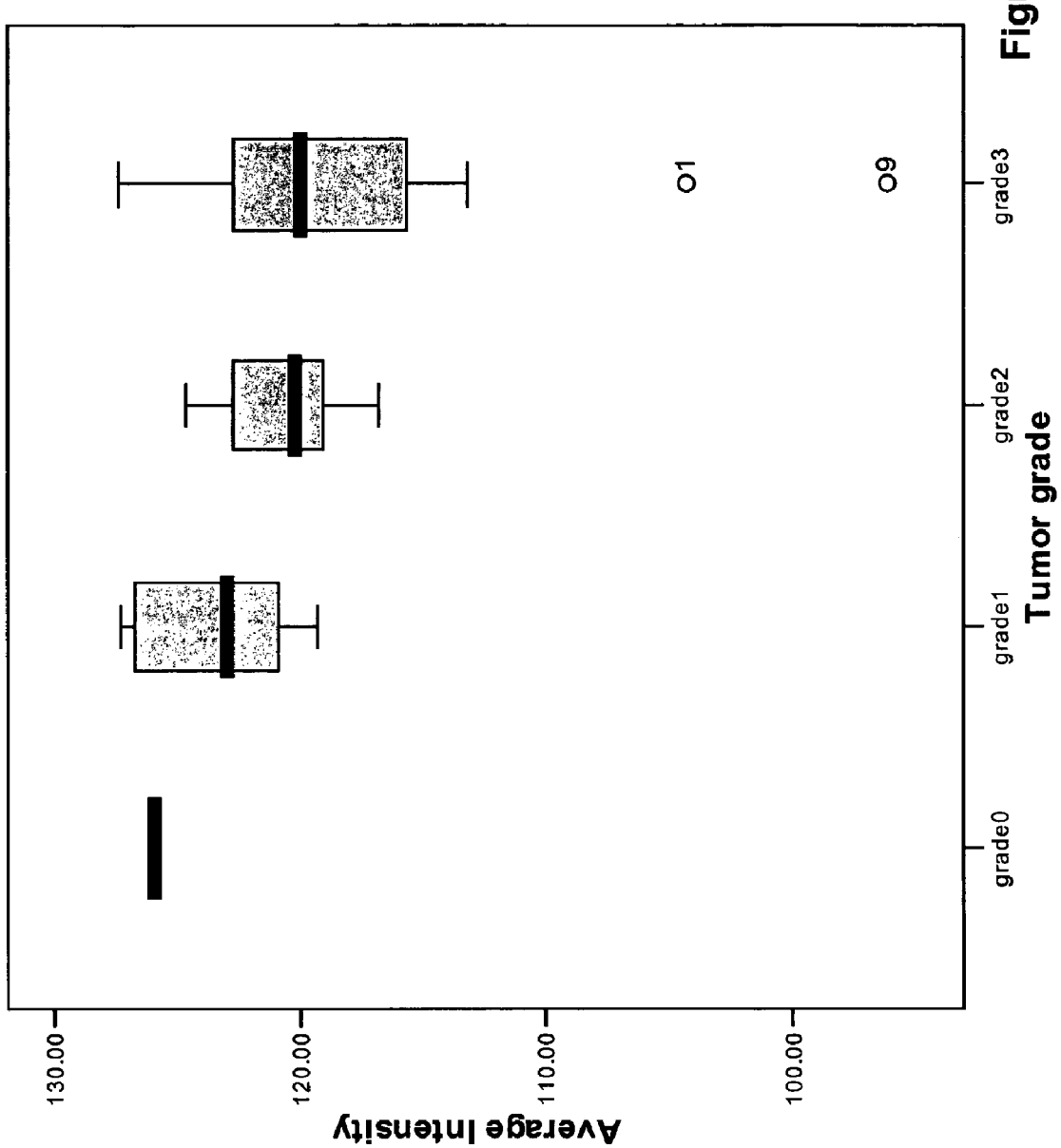

| | | Cases | | | | | |
|---|---|---|---|---|---|---|---|
| | | Valid | | Missing | | Total | |
| | | N | Percent | N | Percent | N | Percent |
| V8 | V16 grade0 | 1 | 100.0% | 0 | .0% | 1 | 100.0% |
| | grade1 | 9 | 100.0% | 0 | .0% | 9 | 100.0% |
| | grade2 | 5 | 100.0% | 0 | .0% | 5 | 100.0% |
| | grade3 | 14 | 100.0% | 0 | .0% | 14 | 100.0% |

Figure 11C

METHOD AND SYSTEM FOR IMAGE ANALYSIS

This application is a national stage application of International Application No. PCT/IE2008/000119, filed Dec. 4, 2008, which claims the benefit of priority to Irish patent application number IE S2007/0882, filed Dec. 4, 2007, the disclosures of each of which are herein incorporated by reference in their entireties.

TECHNICAL FIELD

The present invention relates generally to a method for determining the level of expression of one or more candidate objects of interest in a biological sample. In particular, the present invention relates to a method for determining the level of expression of one or more candidate objects of interest using image analysis. More specifically, the present invention relates to a method for determining the level of expression of one or more candidate objects of interest using an automated (computer-aided) image analysis system.

BACKGROUND OF THE INVENTION

One of the disappointing aspects of the post-genomic era is that whilst a plethora of putative biomarkers have undergone preliminary clinical evaluations, only a small minority have received regulatory approval for clinical use from agencies such as the US Food & Drug Administration (FDA). This is evident from the small number of clinical markers currently used in breast cancer. Although the sequencing of the human genome is likely to have a profound influence on public health in the long-term, there have not as yet been a large number of practical advances regarding the development of new biomarkers based on this information. This has led to a concern that the level of investment in research is not being reflected in improved clinical outcomes, and there is particular concern that the benefits from the 'genetic revolution' have been slow to arrive. This apparent bottleneck in transfer from putative biomarker discovery to clinical application is primarily down to a lack of rigorous validation of emerging biomarkers.

In the field of medical diagnostics including oncology, the detection, identification, quantitation and characterization of cells of interest, such as cancer cells, through testing of biological specimens is an important aspect of diagnosis. In aiding a clinician in the diagnosis of cancer, a pathologist faces two key problems. Firstly, the pathologist must determine whether a tissue or cell sample removed from a patient is benign or malignant. Secondly, upon reaching a determination that the tissue or cell sample is malignant, the pathologist must then classify the aggressiveness of the cancer and determine its clinical and biological behavior.

A diagnosis of cancer must be confirmed through histological examination of a tissue or a cell sample removed from a patient. Such histological examination entails tissue-staining procedures that allow the morphological features of the tissue to be readily examined under a light microscope. The pathologist, after having examined the stained tissue or cell sample, makes qualitative determinations of the state of the tissue or the patient from whom the sample was removed and whether the tissue is benign or malignant. The aggressiveness of the tumour, however, is difficult to ascertain using standard histological techniques. The clinician uses the pathologist's histological analysis to select a suitable treatment, balancing the resistance or responsiveness of the cancer to therapy with the potential harm to the patient resulting from the selected therapy (Muss et al., 1994, N. Engl. J. Med. 330: 1260-66).

In the past, the examination of biological specimens has been performed manually by either a laboratory technician or a pathologist. In the manual method, a slide prepared with a biological specimen is viewed at a low magnification under a microscope to visually locate candidate cells of interest. Those areas of the slide where cells of interest are located are then viewed at a higher magnification to confirm those objects as cells of interest, such as tumour or cancer cells. The manual method is a tedious, time consuming subjective and often variable process to which only limited statistical confidence can be assigned due to inherent intra- and inter-observer variability [31, 32].

In the manual method, Immunohistochemistry (IHC) performed on formalin fixed tissue sections is the most commonly used assay and has replaced other biochemical-based methods using cell suspensions, which consisted of a mixture of normal and malignant tissues. In this regard, IHC based receptor analysis enables assessment of the tissue architecture and is also applicable on small tumours, which were often not suitable for biochemistry based assays. By way of example, hormone receptor status is routinely evaluated in all resected primary breast cancer tumours to assess the levels of Estrogen Receptor (ER) and Progesterone Receptor (PR). Currently, hormone receptor status is manually assessed by a pathologist and an arbitrary cut off of 10% positive cells (regardless of intensity) is used to decide whether a patient should have adjuvant hormonal therapy. Such an arbitrary cut off can lead to significant intra-observer variability.

Although there has been a concerted effort to improve IHC by the use of external quality assurance schemes, there is no equivalent check on those undertaking assessment. Whilst most of the known IHC histological scoring methods have been shown to correlate with clinical outcome when used by experienced pathologists [16, 17] an inherent intra- and inter-observer variability is a significant problem. For example, one study of 172 German pathologists highlighted the difficulties that can arise with manual interpretation, with 24% of ER staining interpreted as being falsely negative [18]. Thus IHC continues to lag behind in two key areas, which are: (i) interpretation and analysis of the stained target protein and (ii) accurate quantification of signal.

Some investigators believe that the solution to the problem of interpretation may be found in improved methods of image analysis [19-22]. Image analysis offers the potential to develop objective automated linear quantitative scoring models for IHC. A move away from the semi-quantitative manual scoring models currently employed would lead to less variability in results, increased throughput and the identification of new prognostic subgroups, which may not have been evident following initial manual analysis.

Accordingly, more recently, the visual examination of tissue and cell samples is often augmented by the use of a semi-automated (computer-aided) image analysis system. A representative system includes a computer that receives a magnified image of the tissue or cell sample from a television camera and processes the received optical image. Image analysis is generally used to assess the affinity of stains, such as IHC stains, for various biological markers.

The coupling of affinity staining and computer-aided image analysis has permitted clinicians to better select optimal therapies for their patients (such as, for example, hormone therapy for cancers that are ER and PR positive and anti-oncogene receptor therapy, such as using monoclonal antibodies directed against HER-2/neu (Herceptin), Epidermal Growth Factor Receptor (EGFR), or C225, alone or in combination with chemotherapy). In addition, image analysis techniques can be used to quantitate other receptors such as those in the erbB receptor family (HER-1, HER-2/neu, HER-3, and HER-4), their ligands (EGF, NDF, and TGFa), and downstream signals (PI3 kinase, Akt, MAP kinase, and JUN kinase).

Indeed, most of the high throughput work to date on image analysis of IHC of breast cancer receptor, such as ER, PR and HER2, has concentrated on the use of tissue microarrays (TMAs). With the advent of TMAs and high throughput pathology, new demands have been placed on the quality, reproducibility and accuracy of this high throughput platform, including the standardisation of interpretation for affinity stained biological specimens. Some of these approaches/systems have become redundant, while others allow (through use of a semi-automated image analysis approach) an increased sensitivity in relation to scoring of staining intensity.

One problem associated with the foregoing semi-automated systems is the difficulty in distinguishing between specifically stained (that is, positively stained) cells of interest, non-specifically stained (that is, negatively stained) cells of interest and background cells which are not of interest. By way of example, many semi-automated systems appear to have difficulty in distinguishing between negative tumour nuclei from stromal tissue and nuclei from lymphocytic infiltrate when assessing the level of ER and/or PR in biological samples.

Another problem associated with the semi-automated approach is the requirement for a manual calibration of the system to determine the morphologic and/or colorimetric features and/or patterns of the candidate cells of interest. This manual calibration step requires the continued need for operator input to initially locate candidate objects of interest for analysis. Such continued dependence on a manual input can lead to errors including cells of interest being missed. Such errors can be critical especially in assays for so-called rare events, such as, for example, finding one tumour cell in a cell population of one million normal cells. In certain rare event detection applications, it is important not to have false negatives. That is, it is important not to miss groups of disease specific cells, such as tumour cells clusters, despite their sparse occurrence and difficulty of detection.

For certain disease-specific states, the semi-automated approach also requires the intervention of an expert to distinguish between abnormal and normal cells. Differentiation based on some morphological features associated with certain disease specific cells, such as, for example, tumour cells, is subtle and requires an experienced pathologist for detection. Consequently, a prior knowledge of or an intensive training to identify the morphological features of the candidate cells and background stroma or epithelium cells is required to run the image analysis methods and systems implementing such methods which are disclosed in the art. By way of example, WO 2004/079636 (Aperio) discloses a semi-automated image analysis method and a system implementing the method which require both a training stage (by, for example, an expert in the biological sciences) and a pattern recognition stage.

A semi-automated image analysis approach which uses a "supervised" training step can be extremely time consuming because it requires a high degree of training to identify and/or quantify candidate cells of interest. This is not only true for tumour cell detection, but also for other applications ranging from neutrophil alkaline phosphatase assays, reticulocyte counting and maturation assessment, and others. The associated manual labor leads to a high cost for these procedures in addition to the potential errors that can arise from long, tedious manual examinations.

A further problem associated with the foregoing semi-automated systems is linked to the high degree of variability in respect to disease specific patterns across different patient samples. The currently available image analysis methods and systems implementing such methods often fail to reproduce the same results across different patient samples because they fail to allow for disease specific heterogeneity, such as tumour cell heterogeneity, on a patient by patient basis. In some instances, non-specific disease patterns are often misinterpreted as disease specific patterns. Indeed, one of the arguments leveled at TMAs is that they may not give a true representation of target biomarker that may have a heterogeneous pattern of expression across different patient samples.

Although TMA staining techniques have provided a considerable advantage in speeding up molecular assaying, the analysis of such results continues to be time-consuming and may be subject to more increased error than other types of assay systems. What is needed, therefore, is an improved image analysis method and system implementing such a method, which would provide for the rapid assay of a microarray so that the advantages of bulk microarray treatment techniques can be fully realized. If the true potential of TMAs is to be fulfilled, an improved image analysis method to rapidly and precisely quantify the expression of candidate biomarkers of interest within each tissue sample is required.

A need exists, therefore, for an improved image analysis method and an automated system for implementing the image analysis method which eliminates the need for operator input to locate and identify candidate objects of interest in a biological sample for analysis.

A need also exists for an improved automated image analysis method and a system for implementing the image analysis method which can quickly and accurately scan large amounts of biological material on a slide and provide an accurate measurement of the level of expression of one or more candidate objects of interest in a biological sample. Crucially, there is a need to develop approaches that can accurately quantify biomarker expression at different subcellular levels, be that at a nuclear, cytoplasmic and/or membraneous level.

The development of such methods and systems implementing such methods would have wide application in the treatment of diseases, such as cancer.

SUMMARY OF THE INVENTION

An image analysis method has been developed which recognises differences in the profiles of one or more candidate objects of interest which may be present in biological samples from subjects with various diseases. In particular, the image analysis method and the image analysis system implementing the method facilitates the accurate detection, differentiation and quantitation of one or more candidate objects of interest in different biological samples. Thus, the image analysis method and system for implementing the image analysis method of the present invention provides a standardised interpretation method and a standardised system for the analysis of biological samples because it takes account of cellular and/or tissue heterogeneity across different patient samples.

In this regard, both the image analysis method and the system for implementing the image analysis method assimilate the morphological characteristics and/or patterns of positively stained candidate objects of interest, such as positively stained cells, and then use the assimilated morphological characteristics and/or patterns of the positively stained cells to segment the negative stained cells into relevant and irrelevant group. The irrelevant group can then be eliminated from the analysis. The contribution of each positive stained cell of interest and each negatively stained cell of interest is determined by an auto-calibration step. Using this non-supervised learning approach, subtle, non-obvious differences in the morphological characteristics of candidate cells of interest can be detected with high sensitivity, selectivity and accuracy. The image analysis method and the system for implementing the image analysis method of the present invention have applications in many different fields. In particular, the method and the system have applications in the diagnosis and/or prevention and/or treatment and/or prognosis of patients with different disease states.

The method of the present invention may be implemented using a computer to provide a fully automated system to accurately assess the expression levels of one or more candidate objects of interest, especially in a large number of biological samples from patients, such as those used in High Throughput Screening (HTS) of TMAs.

Using this image analysis method and system, a variety of different thresholds and their effect on patient outcome were examined using three different types of TMAs. In this regard, a threshold of 10% in the continuous data was found to correlate well with the clinical outcome of the same threshold in the manual data. Moreover, a threshold of 7.0% in ER and 5% in PR continuous data was found to be as good as a 10% threshold in predicting patient outcome. These data indicate that more optimal thresholds can be identified using the continuous data produced by this image analysis method.

In a clinical context, the image analysis method and system for implementing the image analysis method of the present invention may be used as a diagnostic aid for quantifying the level of expression of one or more candidate objects of interest on full-face sections.

In a research context, the image analysis method and system for implementing the image analysis method of the present invention may be used to screen a cohort of patient samples for tissue samples that are either negatively stained for the one or more candidate objects of interest or that are clearly positively stained for the one or more candidate objects of interest. When applied to TMAs, the image analysis method may be used to predict the level of expression of each candidate object of interest and a pathologist may validate the output as a continuous variable on those tissue cores. In particular, the image analysis method can easily be utilised to examine expression levels of a range of candidate objects of interest which are biomarkers for different disease states.

Statements of Invention

Accordingly, in one aspect of the invention, there is provided a method for the analysis of an image of a biological sample comprising one or more candidate objects of interest, comprising the steps of:
obtaining an image of the biological sample;
separating the image of the biological sample into a First Image and a Second Image;
assimilating the morphological features and/or morphological patterns of the one or more candidate objects of interest in the First Image;
applying to the Second Image the morphological features and/or morphological pattern assimilated from the First Image;
eliminating from the Second Image objects with non-matching morphological features and/or non-matching morphological patterns with the one or more candidate objects of interest in the First Image; and
quantitating the level of expression of the one or more candidate objects of interest in the First Image using the matching morphological features and/or morphological patterns of the one or more candidate objects in the First Image and the Second Image.

In a second aspect of the invention, there is provided a method for the automated analysis of an image of a biological sample comprising one or more candidate objects of interest, comprising the steps of:
obtaining an image of the biological sample;
separating the image of the biological sample into a First Image and a Second Image;
assimilating the morphological features and/or morphological pattern of the one or more candidate object or areas of interest in the First Image;
applying to the Second Image the morphological features and/or morphological pattern assimilated from the First Image;
eliminating from the Second Image objects with non-matching morphological features and/or non-matching morphological patterns with the one or more candidate objects of interest in the First Image; and
quantitating the level of expression of the one or more candidate objects of interest in the First Image using the matching morphological features and/or morphological patterns of the one or more candidate objects in the First Image and the Second Image.

In a third aspect of the invention, there is provided a computer program stored on a computer-readable medium, for the automated image analysis of a biological sample, the computer program comprising instructions for causing a computer to: process a biological sample comprising one or more candidate objects of interest; obtain an image of the biological sample; separate the image of the biological sample into a First Image and a Second Image; assimilate the relevant morphological features and/or morphological pattern of the one or more candidate objects of interest in the First Image; apply to the Second Image the morphological features and/or morphological pattern assimilated from the First Image; eliminate from the Second Image objects with non-matching morphological features and/or non-matching morphological patterns with the one or more candidate objects of interest in the First Image; and quantitate the level of expression of the one or more candidate objects of interest in the First Image using the matching morphological features and/or morphological patterns of the one or more candidate objects in the First Image and the Second Image.

In a fourth aspect of the invention, there is provided a computer executing the computer program of the third aspect.

In a fifth aspect of the invention, there is provided an apparatus for quantification of one or more candidate objects of interest in a biological sample comprising: means for obtaining an image of the biological sample;
means for separating the image of the biological sample into a First Image and a Second Image;
means for assimilating the relevant morphological features and/or morphological pattern of the one or more candidate objects of interest in the First Image;
means for applying to the Second Image the morphological features and/or morphological pattern assimilated from the First Image;
means for eliminating from the Second Image objects with non-matching morphological features and/or non-matching morphological patterns with the one or more candidate objects of interest in the First Image; and
means for quantitating the level of expression of the one or more candidate objects of interest in the First Image using the matching morphological features and/or morphological patterns of the one or more candidate objects in the First Image and the Second Image.

In a sixth aspect of the invention, there is provided an automated system for quantification of one or more candidate objects of interest in a biological sample comprising
means for obtaining an image of the biological sample;
means for separating the image of the biological samples into a First Image and a Second Image;
means for assimilating the relevant morphological features and/or morphological pattern of the one or more candidate objects of interest in the First Image;
means for applying to the Second Image the morphological features and/or morphological pattern assimilated from the First Image;
means for eliminating from the Second Image objects with non-matching morphological features and/or non-matching morphological patterns with the one or more candidate objects of interest in the First Image; and
means for quantitating the level of expression of the one or more candidate objects of interest in the First Image using the matching morphological features and/or morphological patterns of the one or more candidate objects in the First Image and the Second Image.

Advantageously, the method and/or apparatus and/or system of the present invention provide for an automated analysis of an image of a biological sample which eliminates the need for operator input to locate and identify candidate objects of interest for analysis.

In particular, the present invention also provides a fully/completely automated, local non-supervised leaning approach for distinguishing different morphologic patterns for individual patients. This approach does not require any prior knowledge on the morphological features of the candidate objects of interest, such as cells, which allows a non-expert user to easily use the automated image analysis method and/or the system which implements the image analysis method. In addition, this approach also eliminates the manual step of calibration and thus saves valuable time for both researchers and clinicians.

In one embodiment of these aspects, the First Image and the Second Image are optically enhanced.

In a further embodiment of these aspects, the First Image and the Second Image are optically enhanced by transforming substantially all of the First Image and the Second Image from a first colour space to a second colour space.

In another embodiment of these aspects, the morphological features and/or morphological pattern of the one or more of the candidate objects of interest in the First Image are assimilated by measuring the distance between the candidate objects of interest and then grouping the candidate objects of interest into at least a first spatially adjacent group and a second spatially distant group such that the mean distance between and the mean area encompassed by the candidate objects of interest in the one or more spatially adjacent groups represents a candidate positive group.

As used herein, the term "spatially adjacent group" means a plurality of candidate objects of interest which are in close proximity to each other.

As used herein, the term "spatially distant group" means a plurality of candidate objects of interest which are spaced apart or far removed from each other.

In an additional embodiment of these aspects, the morphological features and/or morphological pattern of the one or more candidate positive groups in the First Image are matched with the same morphological features and/or morphological pattern of the one or more candidate objects of interest in the Second Image to form one or more candidate negative groups in the Second Image.

In a further embodiment of these aspects, objects with non-matching morphological features and/or non-matching morphological patterns with the one or more candidate objects of interest in the candidate positive group are eliminated using a threshold analysis technique. Using this technique, a boundary is set on the mean area encompassed by the one or more candidate objects of interest in the candidate positive group and/or the mean distance between the candidate objects of interest in the candidate positive group. Once the boundaries are set, any parts (eg any objects) of the First Image and/or the Second Image with boundary values which are above or below the thresholds which have been set, are eliminated. Preferably, the "boundary" is selected from the group consisting of a standard deviation (STD) value or a STD range.

In an even further embodiment of these aspects, the quantitation of the level of expression of the candidate positive group is expressed as a percentage of the total number of candidate objects of interest in the candidate positive group and the candidate negative group. Advantageously, the method of the present invention uses an "internal calibration" or "self-training" step for each biological sample which relies on feature matches (such as, for example, similar shape and/or size of one or more candidate objects of interest) and cluster pattern matches (such as, for example, equivalent distance between spatially adjacent candidate objects of interest) for marker positive and marker negative cells of interest) and feature mis-matches and cluster pattern mis-matches to differentiate marker negatively stained candidate objects of interest from background objects. In other words, the contribution of each candidate positive group and each candidate negative group is independently calibrated (or measured) for each patient sample which makes allowance for disease specific heterogeneity on a patient by patient basis.

Preferably the one or more candidate objects of interest is/are detected by immunochemistry.

Preferably the one or more candidate objects of interest is/are detected by a stain.

Preferably the one or more candidate objects of interest is/are detected by a combination of immunohistochemistry and a stain.

Preferably the stain is a protein stain.

Preferably the biological sample is selected from the group consisting of a tissue sample, a tissue section, a tissue microarray and a cellular sample.

Preferably the biological sample is a tumour sample.

The image analysis method and the system implementing the image analysis method of the present invention is particularly advantageous for distinguishing different morphologic features and/or patterns of candidate objects of interest from (TMA) samples. The fully automated image analysis method and system implementing the image analysis method of the present invention also allows high throughput screening (HTS) and provides a "standardized" method which removes the subjective analysis aspect of the manual method. The automated image analysis method and system of the present invention thus allows for the rapid, precise and in-depth evaluation of disease specific heterogeneous cells, such as heterogeneous tumour cells, located on histologic slide or from individual cores on a TMA.

Preferably the image is a digital image. Advantageously, each digital image is automatically calibrated on a sample by sample basis.

Preferably the image is obtainable by scanning a biological sample.

In an seventh aspect of the invention, there is provided a method for determining the level of expression of one or more candidate objects of interest in a biological sample, wherein the method comprises:

immunohistochemically staining the biological sample;

obtaining an image of the biological sample;

separating the image of the biological sample into a First Image and a Second Image;

assimilating the morphological features and/or morphological pattern of the one or more candidate objects of interest in the First Image;

applying to the Second Image the morphological features and/or morphological pattern assimilated from the First Image;

eliminating from the Second Image objects with non-matching morphological features and/or non-matching morphological patterns with the one or more candidate objects of interest in the First Image; and quantitating the level of expression of the one or more candidate objects of interest in the First Image using the matching morphological features and/or morphological patterns of the one or more candidate objects in the First Image and the Second Image.

In one embodiment of this aspect, the one or more candidate objects of interest is/are expressed in tumour cells.

In a further embodiment of this aspect, the one or more candidate objects of interest is/are expressed in a nucleus of a tumour cell.

In yet another embodiment of this aspect, the one or more candidate objects of interest is/are selected from the group consisting of an Estrogen Receptor (ER) and/or a Progesterone Receptor (PR).

The method of the present invention offers several advantages over techniques disclosed in the prior art. By way of example, using the method of the present invention, the level of expression of one or more candidate objects of interest may be assayed in the tumour cells of a tissue sample (excluding normal tissue removed from the patient with the tumour sample), thus generating a more meaningful quantitation of the specific candidate object of interest within the tissue sample. Furthermore, the method of the present invention overcomes the problems associated with cell staining variability that result from variations in staining conditions.

The image analysis method and the system for implementing the image analysis method of the present invention are particularly suited to the analysis of cells, such as tumour cells, because a key step in the method of the present invention resides in the recognition of disease specific cellular patterns in the microscopic images of the biological sample which are based on specific morphological features associated with the target cells of interest. By way of example, tumour cells may be differentiated from normal cells based on the following morphological features which include but are not limited to cell size, nuclear-to-cytoplasmic ratio, roundness, density, colour and texture, nuclear size and shape. Generally speaking, tumour cell nuclei are usually large and round whereas normal nuclei are smaller and/or irregular in shape.

The image analysis method and the system for implementing the image analysis method of the present invention are suitable for rare event finding, such as the detection of micromestasis clusters, tissue identification, such as location of regions of analysis for immunohistochemical assays and rapid screening of tissue samples, such as histology sections arranged as TMAs.

As the Examples demonstrate, the method is particularly effective in differentiating between candidate positive cells, such as tumour positive nuclei, candidate negative cells, such as tumour negative nuclei and non specific cells, such as non-tumour nuclei (such as, for example, nuclei from lymphocyte infiltrates). Many other commercially available image analysis methods appear to have difficulty in distinguishing candidate negative cells, such as negative tumour nuclei from non-relevant cells such as stromal tissue and lymphycyte infiltrated cells.

The method of the present invention is particularly useful for determining the level of expression of receptor proteins such as the estrogen receptor (ER) and the progesterone receptor (PR) as these proteins play a major role in determining specific biological therapeutic approaches.

In an eighth aspect of the present invention, there is provided a system for processing a digital image and an image processing method comprising the steps for processing a digital image as set out in any one or more of the FIGS. 6, 7, 8 and 9. The image analysis method and the system for implementing the image analysis method of the present invention allow for the conservation of precious tissue resources because a "bright field" method (ie using light microscopy) which permits the use of previously stained sections and provides a simple system, which dispenses with need for additional hardware such as filters and the like.

DETAILED DESCRIPTION AND DEFINITIONS

Various terms that will be used throughout the specification have meanings that will be well understood by the skilled addressee. However, for ease of reference, some of these terms will now be defined.

As used herein, the term biological sample means a sample of biological origin. The term "sample" includes cellular material derived from a subject. The biological sample includes but is not limited to a hair sample, a skin sample, a tissue sample, a tissue section, a biopsy sample, a cultured cell, a cultured cell media, a biological fluid specimen, for example, a blood fraction cytospun on a microscope slide or a cell suspension directly seeded on a slide. The term "sample" also includes media containing isolated cells. The sample may be a human, animal or plant cell or tissue sample. The quantity of sample required to obtain a reaction may be determined by one skilled in the art by standard laboratory techniques. The optimal quantity of sample may be determined by serial dilution.

The term "tissue" refers to a mass of connected cells (such as, for example, Central Nervous System (CNS) tissue, neural tissue, eye tissue or the like) derived from a human or other animal and includes the connecting material and the liquid material in association with the cells. The term "biological fluid" refers to liquid material derived from a human or other animal. Such biological fluids include, but are not limited to, blood, plasma, serum, serum derivatives, bile, phlegm, saliva, sweat, amniotic fluid, and cerebrospinal fluid (CSF), such as lumbar or entricular CSF.

Typically, a biological sample such as but not limited to a sample from: bone marrow, lymph nodes, peripheral blood, cerebrospinal fluid (CSF), urine, effusions, fine needle aspirates, peripheral blood scrapings or other material which is prepared by staining the specimen to identify one or more candidate objects of interest, such as cells and cell features of interest.

As used herein, a "candidate object of interest" means a molecule or a group of molecules or a marker or a group of markers (also known as "biomarkers"), which is/are present in only a subset of the components of a biological sample and therefore identifies specifically the components of the biological sample having that molecule or marker. By way of example, the candidate object of interest includes but is not limited to any one or more of the following: a cell, a group of cells or a cluster of cells, a cell membrane, a cell cytoplasm, a cell nucleus, a cell nucleoli, a cell surface molecule or marker, a cell fragment, a specific cell structure, a cell protein (such as an antigen) and a cell area and/or a region encompassed by a cell or a group of cells in a biological sample. The term also covers any molecular abnormality in a cell when compared with a normal cell.

In the context of the present invention, examples of specific candidate objects of interest include but are not limited to antigens which are recognized by specific antibodies (such as, for example, monoclonals or polyclonals) and can be detected by techniques which include but are not limited to histochemistry, immunohistochemistry, cytochemistry, immunocytochemistry, immunofluorescence, in-situ hybridization and the like. Generally, gene expression is detected using in-situ hybridization while protein expression is determined using histochemistry or immunohistochemistry, cytochemistry or immunocytochemistry. The techniques of the present invention also cover co-localisation of one or more candidate objects of interest.

Preferably the candidate marker of interest is detected using histochemistry and/or immunohistochemistry.

Preferably the candidate marker of interest is detected using cytochemistry and/or immunocytochemistry.

Preferably the candidate marker of interest is detected using immunohistochemistry and cytochemistry.

Immunohistochemical Staining

Immunohistochemical (IHC) techniques as used herein encompass the use of reagents detecting one or more candidate objects of interest, such as cell specific markers. Such reagents include, for example, antibodies and nucleic acids probes. One method of biological sample preparation to detect a candidate object of interest is to react a specimen with a specific probe. Any probes that can be detectably labeled and that specifically bind to one or more candidate objects of interest may be used in the practice of the methods of the invention. Examples of specific probes include but are not limited to a monoclonal antibody and/or fragments thereof, a polyclonal antiserum and the like which are often used to identify candidate objects of interest, such as proteins or polypeptides of interest in a biological sample.

IHC localization of proteins or polypeptides of interest uses the ability of antibodies to bind specific antigens, such as onco-proteins and enzymes, with high affinity. These antibodies can be used to localize antigens to subcellular compartments or individual cells within a tissue, such as a paraffin embedded tissue section which can be prepared according to a conventional procedure. The antibodies are incubated with the sample for a time to form complexes if these antigens are present. The reaction may be detected using an enzymatic reaction, such as alkaline phosphatase or glucose oxidase or peroxidase to convert a soluble colorless substrate to a colored insoluble precipitate, or by directly conjugating a dye to the probe.

In one preferred embodiment, the candidate object of interest is identified by adding a detectably-labeled primary antibody specific for the target protein, or alternatively an unlabeled primary antibody and a detectably-labeled secondary antibody specific for the primary antibody. A number of techniques are utilized to label candidate objects of interest according to IHC techniques. Such techniques are discussed in Current Protocols in Molecular Biology, Unit 14 et seq., eds. Ausubel, et al., John Wiley & Sons, 1995, the disclosure of which is incorporated herein by reference. By way of example, an anti-estrogen receptor (ER) antibody labels epithelial cells of breast carcinomas which express ER. An IHC assay of the ER is performed using an anti-ER antibody, for example the well-characterized 1D5 clone, and the methods of Pertchuk et al. (Cancer 77: 2514.sub.—2519, 1996) or a commercially available IHC system such as that provided by DAKO (Carpenteria Calif; DAKO LSAB2 Immunostaining System).

Likewise, an anti-progesterone receptor (PR) antibody labels epithelial cells of breast carcinomas which express PR. An IHC assay of the PR is performed using an anti-PR antibody, for example the well-characterized 1A6 clone, and the methods of Pertchuk et al. (Cancer 77: 2514 2519, 1996).

In one preferred embodiment, the complexes are visualized by treating the sections with a stain such as diaminobenzidine (DAB) to produce a brown stain under appropriate conditions. In a further step, the tissue is counterstained with another optical enhancement factor, for example haematoxylin or ethyl green. Although a staining technique using peroxidase and haematoxylin or ethyl green is exemplary, other stains and optical enhancement factors are also suitable such as alkaline phosphatase based with specific chromages such as Fast Red, Fast Green and the like.

The Examples demonstrate the use of a two-component immunohistochemical staining system which is used to differentially stain a target nuclear protein (such as ER and/or PR) and the tissue or cell sample so that the stained target protein (such as ER and/or PR) can be more readily distinguished from the counterstained tissue or cell sample. As the Examples demonstrate, the target protein is stained using diaminobenzidine (DAB) and the tissue or cell sample is counterstained using either haematoxylin, ethyl green or methylene blue or the like.

This, in a further preferred embodiment, the cell specific marker is detected by a nuclear stain and counterstain.

The term "nuclear stain" refers to a cytochemical stain that preferentially stains the nuclei of eukaryotic cells. Many nuclear stains are intercalating dyes. The term "intercalating dye" refers to a chemical compound that can insert itself in between adjacent nucleotides of a nucleic acid to provide a detectable color. Many nuclear stains are known in the art, with one of the most commonly used being haematoxylin. Haematoxylin is often used in combination with various metallic salts (mordants). Haematoxylin stains are used for different staining purposes, and have a variety of colors, depending on the metal used. Aluminum lakes are purple to blue, depending on pH. Iron lakes are blue-black. Chromium lakes are blue-black. Copper lakes are blue-green to purple. Nickel lakes are various shades of violet. Tin lakes are red. Lead lakes are dark brown. Osmium lakes are greenish brown. Other nuclear stains include but are not limited to Giemsa stain, methyl green, Nuclear Fast-Red, Hoechst 33342, Hoechst 33258, thiazole orange, DAPI, ethidium bromide, propidium iodide, TOTO, YoYo-1, SYTOX Blue, SYTOX Green, 7-Aminoactinomycin, 9-Amino-6-chloro-2-methoxyacridine, and acridine homodimer.

The term "counterstain" when used in combination with nuclear stains, refers to cytochemical stains that bind to a region of a eukaryotic cell other than the nucleus. The purpose of a counter-stain is to stain with a colour contrasting to the principal stain, thus making the stained structure more visible. Many counterstains are known in the art. One of the most common is eosin, which stains eukaryotic cell cytoplasm to varying shades of pink. Other counterstains are specific for a particular organelle or a protein in a cell. For example, the Kleihauer-Betke cytochemical stain is specific for hemoglobin F, a hemoglobin type preferentially expressed in fetal cells and therefore can be defined as a specific marker of fetal red blood cells.

In another preferred embodiment, a combination of techniques using both chemical staining and/or immunohistochemical and/or in-situ hybridization may be used in the present methods. For example, numerous subsamples may be prepared from a single tissue specimen. A first subsample may be chemically stained as discussed above, and a subsequent subsample may be subjected to immuno-histochemical and in-situ hybridization techniques. Images of each subsamples are prepared and processed as discussed below.

Preferably the one or more candidate objects of interest is/are detected using in-situ hybridisation In the case of in-situ hybridization, typically, the marker which hybridizes specifically to a nucleic acid probe is detectably labeled. In-situ hybridization techniques include the use of specifically labeled nucleic acid probes, which bind to cellular RNA or DNA in individual cells or tissue section. Suitable nucleic acid probes may be prepared using standard molecular biology techniques including subcloning plasmid preparation, and radiolabeling or non-radioactive labeling of the nucleic acid probe. In preferred embodiments, the detectable label is a chromagen or a fluorophore. Such labels include enzyme, radioisotopes, fluorescence or other labels well known in the art. In-situ hybridization is often performed on either paraffin or frozen sections. Such techniques often include fine sectioning of tissues to provide samples that are only a single to a few cell layers thick. For example paraffin blocks containing a tissue sample are cut into thin, approximately 8 micron tissue sections, which are subsequently mounted on slides to be further processed for in situ hybridization. Alternatively, methacrylate may be used for sectioning. Cryosectioning techniques are particularly suitable for immunohistochemistry and enzyme histochemistry.

Preferably the one or more candidate objects of interest is/are detected using a fluorescence stain.

In one embodiment, the candidate objects of interest may be identified using FISH (fluorescence in-situ hybridization). A FISH sample is prepared by using a probe that binds to a particular DNA sequence in the chromosomes in a sample and the probe is labeled with a fluorescent dye.

Preferably the one or more candidate objects of interest is/are detected using immunofluorescence.

Immunofluorescent labeling of a tissue section often uses a sandwich assay or a primary antibody and secondary antibody-fluorochrome conjugate. Slides containing a tissue section of interest are washed in phosphate buffered saline and then exposed to a primary antibody which will bind to the protein object of interest. Subsequently the slides are washed and exposed to the secondary antibody which binds to the first or primary antibody. The slide is washed and then developed.

Fluorescent stains include Hoechst 33342; Hoechst 33258 (Calbiochem), a bisbenzimide DNA intercalator that excites in the near UV (350 nm) and emits in the blue region (450 nm); thiazole orange, a fluorogenic stain for DNA that excites in the blue region (515 nm) and emits in the green region (530 nm) of the visible spectrum; DAPI; ethidium bromide; propidium iodide; TOTO; YOYO-1; and SYTOX Blue or Green stains are also encompassed by the current invention. Several dyes either bind GC-rich or AT-rich chromosomal regions preferentially or show differences in fluorescence intensity upon binding those regions, yielding fluorescent banding patterns. For example, 7-Aminoactinomycin D binds selectively to GC-rich DNA regions and 9-Amino-6-chloro-2-methoxyacridine fluoresces with greatest intensity in AT-rich DNA regions. Acridine homodimer fluoresces preferentially when bound to AT-rich DNA regions.

A combination of techniques using both chemical staining and/or immunohistochemical and/or in-situ hybridization and/or immunofluorescence may be used in the image analysis method of the present invention. For example, numerous subsamples may be prepared from a single tissue specimen. A first subsample may be chemically stained as discussed above, and a subsequent subsample may be subjected to immunohistochemical and/or in-situ hybridization techniques. Each subsample is scanned and processed as discussed below.

In one preferred embodiment, the biological sample is mounted on a microscope slide. In another preferred embodiment, the biological sample is presented as part of a tissue microarray (TMA).

Tissue Microarray Technology (TMA)

Tissue Microarray (TMA) technology is a platform for high-throughput pathology and is increasingly being used as a downstream validation tools from DNA microarray-based gene expression profiling studies. The fundamental basis of all of these applications is that TMAs facilitate rapid translation of molecular discoveries to clinical applications by revealing the cellular localisation, prevalence and clinical significance of candidate biomarkers. A TMA is a collection of tissue specimens arranged on a glass slide in a grid-like fashion. TMAs were developed by Kononen et al in 1998 [28] and are a high throughput method for the simultaneous investigation of biomarkers in multiple tissue specimens. Since their inception by Kononen et at in 1998, they have become entrenched in the arsenal of tools and platforms used in translational research [29].

TMAs are assembled by acquiring cylindrical cores (0.6-2.0 mm in diameter) from donor paraffin-embedded tissues and re-embedding them within a single recipient block. In this way, tissue from hundreds of specimens can be inserted into a single paraffin block. The resultant TMA is then sectioned, with 50-75 sections being generated per block. Individual sections with approximately two to three hundred circular tissue sample "dots" may be placed on a microscope slide which can then be subjected to a variety of assays. The most commonly performed assay on TMAs is immunohistochemistry (IHC). However, TNA-based studies employing in-situ hybridization (ISH) for DNA and RNA are increasing in popularity. TMAs have also been used for infra-red spectroscopic and protein blotting studies.

Thus, the image analysis method and the system implementing the method of the present invention also relates to processing of images of a TMA made up of a plurality of TMA dots which have been stained using a combination of techniques including both chemical staining and/or immunohistochemical and/or in-situ hybridization. For example, numerous tissue microarray dots may be prepared from a single tissue specimen. A first subsample may be chemically stained as discussed above, and a subsequent subsample may be subjected to immunohistochemical and in situ hybridization techniques. Each subsample is scanned and processed as discussed below.

Image Analysis Method

The image analysis method of the present invention is useful for accurately determining expression levels of one or more candidate objects of interest of a biological sample.

Specifically, the present invention provides an image analysis method for determining the expression level of one or more candidate objects of interest in a biological sample using a computer-aided image analysis system to enhance and process optical images of a biological sample, such as an immunohistochemically (IHC) stained tissue or cell sample, and to determine the level of expression of the one or more candidate objects of interest in the biological sample. More specifically, the present invention provides a method for determining the level of expression of a target protein in, for example, the tumour cells of a tissue or cell sample removed from a patient.

Summary of the Procedure

The image analysis method of the present invention is practiced on a biological sample comprising one or more candidate objects of interest is generally as follows. After staining, such as IHC staining of the biological sample, an image of the candidate positive cells (hereinafter referred to as a First Image) and the candidate negative cells together with the non-relevant cells (hereinafter referred to as a Second Image) is used to characterize and differentiate between the candidate positive cells, the candidate negative cells and the non-relevant (background) cells based on the morphological attributes and patterns of the candidate positive cells. Once identified, the non-relevant cells can be eliminated from the analysis. The percentage of candidate positive cells is then quantitated as a percentage of the total number of candidate positive and candidate negative cells. The following steps describe the image processing and image analysis methods which are utilized to determine the level of expression of the one or more candidate object of interest in a biological sample of interest.

Staining

As noted above, a specimen cell population is prepared with special staining and counterstaining technique using IHC or any other suitable staining methods known in the art. Appropriate stains and counterstains are selected by their ability to distinguish between the one or more candidate objects of interest. By way of example, specific candidate objects of interest, such as target proteins, may be detected using a specific reagent, most preferably an antibody, that is itself detectably labeled, or using an unlabeled, target protein-specific, or primary antibody and a second antibody that is detectably labeled and recognizes the target protein-specific, or primary antibody. Alternatively, any molecule that can be detectably labeled and that specifically binds to the target protein can be used in the practice of the image analysis method of the present invention.

In a preferred embodiment of the image analysis method of the present invention, a two-component IHC staining system is used to differentially stain the one or more candidate objects of interest, such as a target protein in the tissue or cell sample so that the stained candidate object of interest, such as the target protein, can be more readily distinguished from the counterstained tissue or cell sample. For example, in a first step, any expressed target protein in a cell is identified by adding a detectably-labeled primary antibody specific for the target protein, or alternatively an unlabeled primary antibody and a detectably-labeled secondary antibody specific for the primary antibody. The antibodies are incubated with the sample for a time to form complexes if these target proteins (such as antigens) are present. The complexes are then visualized by virtues of being coupled with a stain such as diaminobenzidine (DAB). The tissue is counterstained with another optical enhancement factor, for example haematoxylin or ethyl green or methylene blue. Although a staining technique using DAB and haematoxylin is exemplary, other stains and optical enhancement factors are also suitable such as alkaline phosphatase based with specific chromogens such as Fast Red, Fast Green, and the like.

Following staining, such as staining described above, for the one or more candidate objects of interest, an optical image of the biological sample, such as the tissue or cell sample, is generated. Using a computer-aided image analysis system, the image is separated into a pair of images, referred to as a First Image and a Second Image.

In one preferred embodiment, and as demonstrated in the Examples, the First image is one in which only those tissue areas with nuclear receptor staining (DAB) for a particular target (such as ER) are optically enhanced while the Second Image is one in which all of the cell nuclei are optically enhanced (using, for example, haematoxylin, ethyl green or Fast Green or the like).

Preferably the image is a digitized image.

As used herein, the term "digitized image" means an electronic representation of a traditional glass slide, which can be laterally examined and viewed under different magnifications using a computer, in a similar fashion to viewing a glass slide using a microscope.

Preferably the digitized image is obtainable by scanning a slide.

The present invention provides techniques for the scanning and analysis of large numbers of cytology and histology samples, using, for example, a flatbed scanner to capture images of the structures of interest (such as, for example, cells, groups of cells, and the like). The scanner provides sufficient image resolution to allow for the analysis of biological samples provided with one or more relevant markers to produce enough brightfield contrast to recognize one or more candidate objects of interest, including samples subjected to such common pathology staining techniques as ICC (immunocytochemistry), IHC (immunohistochemistry), or in-situ hybridization.

Although flatbed scanners have not been designed for the purpose of producing digital image of a biological sample for subsequent analysis and classification, the present invention is able to use such scanners to enable the automated analysis of a large number of samples with a practical throughput. This has potentially immense consequences in many high-volume scanning applications. In particular, the use of a flatbed scanner makes it possible to quickly analyze the large number of slides per patient created by the serial sectioning described above, in particular, for the production of TMAs. Examples of devices that include both image capture and analysis functions include but are not limited to the Aperio Scanscope (Aperio Technologies, Vista, Calif., USA0 and ACIS (Calrient, Inc, Aliso Viejo, Calif., USA) systems.

Image Processing

The image processing steps for the First Image and the Second Image include but are not limited to color space conversion steps, segmentation steps, morphological processing steps and quantitative analysis steps. The sequence of steps may be optimized for specific reagents and/or reagent combinations, the implementation of which would be routine. The first two image processing steps comprising colour space conversion steps and segmentation steps are generally known image processing building blocks steps. However, the subsequent image processing steps which rely on morphologically processing steps and/or the image quantitation steps have not previously been disclosed in the art in the field of automated image analysis of biological samples. In particular, the morphological processing steps have not been disclosed either in the context of IHC staining analysis and/or IHC staining analysis of TMAs. More specifically, the morphological processing steps which rely on the morphological characteristics (such as, for example, size and shape of the one or more candidate objects of interest) and/or morphological patterns of the one or more candidate objects of interest, such as groups of target cells of interest, have not previously been applied to quantitate IHC staining of tumour cells from TMA samples. An overview of the preferred process is shown in FIGS. 6, 7, 8 and 9 and is described in the Specific Examples.

Colour Conversion Process

The chain of the decision making steps based on the morphological characteristics of the candidate objects of interest, such as target cells of interest, preferably begins with a colour space conversion process which process is also known interchangeably throughout the specification and in the art as a colour channel coding process, a colour channel optimization process, a colour deconvolution process or a colour space transformation process.

The purpose of the colour channel conversion process is to optially enhance the positive image relative to the negative image. The effect of the colour transformation process is to optically enhance (make darker/lighter) those areas of the sample where one or more candidate objects of interest are positively stained, such as with DAB, and to make lighter/darker those one or more candidate objects of interest which are negatively stained, such as, for example, with only green counterstain. The implementation of this step provides a convenient and advantageous method for discriminating between two differentially stained areas.

Using conventional colour channel transformation, three colour stains in an original image such as red, green, blue stains (as known as RGB) may be accurately separated and the contribution of each stain can be measured independently. In addition, relatively lightly stained candidate objects of interest may be distinguished from more intensely stained candidate objects of interest by virtue of different colour saturations. It is generally desirable to transform the matrix of RGB values to a different color space because the difference between candidate objects of interest and their background, such as tumour and normal cells, may be more accurately determined from their respective colors.

One classical method converts the three colour stains (such as red, green, blue, RGB stains) colour information, in the original image into another color space, such as an HSI (hue, saturation, intensity) space. In this color conversion operation, a ratio of two of the RGB signal values is formed to provide a means for discriminating color information. With three signal values for each pixel, nine different ratios can be formed: R1R, R/G, RUB, G/G, G/B, G/R, B/B, B/G, B/R. The optimal ratio to select depends upon the range of color information expected in the slide specimen.

Other known methods for discriminating color information convert the RGB colour space to HSV or LUV colour spaces.

Preferably, the colour space transformation coverts the RGB colour space to an LAB/LUV colour space. LAB and LUV are perceptually uniform colour spaces in which calculated distances between colours in a colour space approximately reflect visually perceived colour differences. L is a lightness scale from 0 (black) to 100 (reference white), A and U are red-green scales and B and V are yellow-blue scales. DAB is extracted from the original image and converted from RGB to CIE LUV color space. There are numerous alternative colour representations (see, e.g. [1], [2]), which transform the RGB values linearly or non-linearly to different colour spaces. A brief summary and description of some of the most commonly used device independent color spaces follows:

| Colour Space | | |
|---|---|---|
| XYZ | Y = Luminescence (cd/m2) | XZ = spectral weighting curves (spectral locus) |
| xyY | Y = Luminescence (cd/m2) | xy = chromaticity coordinates (spectral locus) |
| Lab | L = Luminescence (density) | a = red/green; b = blue/yellow |
| Luv | L = Luminescence | u = saturation v = hue angle |
| LCh | L = Luminescence | C = chromacity h = hue angle |
| YCrCb | Y = Luminescence | Cr = red/yellow Cb = blue/yellow |
| YUV | Y = Luminescence | U & V = Color information |
| UVW | W = Luminescence | U & V = Color information |
| CMYK | | C = cyan, M = magenta, Y = yellow, K = black |
| RGB | Color matching curves | R = 700 nm G = 546.1 nm B = 435.8 nm |

It is recognized that there are various other staining or optical enhancement methods and filtering methods which can be used to optically enhance one particular area or feature over another cell feature. Typical stains used for detecting candidate objects of interest, such as tumour cells, are predominantly red.

By way of example, stains such as DAB, New Fuchsin, AEC are typically "reddish" in color, as opposed to predominantly green or blue. Thus, the pixels of a candidate object of interest which has been stained may contain a red component which is larger than either the green or blue components. A ratio of red divided by blue (R/B) provides a value which is greater than one for candidate objects of interest, such as tumour cells, but is approximately one for any clear or white areas on the slide. Since the remaining objects, such as the normal cells, typically are stained blue, the R/B ratio for pixels of these latter cells yields values of less than one. The R/B ratio is one example of a preferred method for clearly separating the color information typical in these colour channel conversion applications.

This technique can also be applied where a marker is expressed in both the nucleus and cytoplasm. The original image may contain both nuclear and cytoplasmic staining combined. In this regard, DAB is a nuclear and cytoplasmic stain whereas haematoxylin is a nuclear stain only. Using colour space transformation, the brown colour (positive cells) may be separated from the blue colour (negative cells). Candidate objects of interest retain more of the stain and thus appear red while DAB negative tumour cells and normal (non-tumour) cells remain unstained. The specimens may also be counterstained with haematoxylin so that the nuclei of all non DAB positive cells appear blue. In addition to these objects, dirt and debris can appear as black, gray, or can also be lightly stained red or blue depending on the staining procedures utilized. The residual plasma or other fluids also present on a smear may also possess some color.

Of the cells which appear blue, a subset may comprise DAB negative tumour cells.

Colour Segmentation

The separated images may be further enhanced using segmentation techniques.

In particular, the separated images may be further enhanced using conventional colour segmentation methods.

As used herein, the term "segmentation" means a demarcation of the First Image and optionally the Second Image based on colour. In other words, the term "segmentation" means creating a more defined or visible or clearer or a more enhanced image of the candidate object of interest while suppressing the background material.

Preferably the segmentation step includes one or more mean-shift segmentation steps.

Mean shift segmentation is a process which is well known to the person skilled in the art. Mean shift segmentation techniques are discussed in the following publications, all of which are incorporated herein by reference: Sangwine, SAH, "*The Colour Image Processing Handbook*" REN ed, CAHall, 1998, London; Gonzalaez R "*Digital Image Processing*" Reading, Ed Addison-Wesley, 1992, MA; Comanicu, P M "Mean Shift: "*A robust approach towards feature space analysis*" IEEE Trans Pattern Anal Machine INtell 2002 24: 603-619; and Yang C, DeMenthon, D, Davis, L "*Mean Shift Analysis using quasi-Newton Methods*" IEEE International Conference on Image Processing 2003: 447-450.

Preferably the segmentation step includes one or more watershed segmentation steps.

Watershed segmentation is a process which is well known to the person skilled in the art. Watershed segmentation techniques are disclosed in, for example, WO 2005/119595.

The purpose of watershed segmentation is to create a 3D view of the stains, again to provide a clearer, more defined image of the positively stained candidate objects of interest (as presented in the First Image) relative to the negatively stained candidate object of interest (as presented in the Second Image).

To further differentiate those areas, an (automated) threshold setting technique may be used where a boundary can be set on the areas (in the first and second images) under consideration. When the boundaries are set, the images are formed by eliminating all parts of the image that are below the thresholds which have been set. A threshold is set for the First Image, and a second threshold is set for the Second Image.

Morphological Processing

After the colour channel conversion steps and the colour segmentation steps, a morphological analysis of the segmented images is performed. In order to take account of possible heterogeneity between candidate objects of interest across a range of disease specific biological samples, the morphological and/or spatial parameters describing the characteristic and/or patterns of the more than one candidate object of interest are defined on a sample by sample basis. That is, the parameters defining the morphological characteristics and/or patterns of the positively stained candidate objects of interest are assimilated and the same morphological and spatial parameters are applied to separate the negatively stained candidate objects of interest from any non relevant objects which are not of interest. In one preferred embodiment, the positively stained candidate objects of interest are characterized morphologically based on size and shape and characterized spatially by grouping candidate objects of interest which are in close proximity together to form a candidate positive group. This group is then matched with any negatively stained candidate objects of interest. Any objects which are not of interest are eliminated because of their non-matching morphological and/or spatial characteristics, such as, for example, different size and shape or distant location from the location of the candidate negative group.

As used herein, the term "morphological feature" means any attribute/characteristic that may be exhibited by a candidate object of interest, such as shape, size, of one or more candidate objects of interest within a biological sample, such as a TMA sample. Such morphological features include but are not limited to: cell size, nuclear-to-cytoplasmic ratio, roundness, density, colour and texture, nuclear size and shape and nucleoli size and shape.

Preferably the morphological features and/or morphological pattern of the one or more of the candidate objects of interest in the First Image are assimilated by measuring the distance between the candidate objects of interest and then grouping the candidate objects of interest into at least a first spatially adjacent group and a second spatially distant group such that the mean distance between and the mean area encompassed by the candidate objects of interest in the spatially adjacent group represents a candidate positive group. Preferably the spatially adjacent group is a group of candidate objects of interest which are in close proximity to each other. Given their close proximity, the spread of the data points for distance between and/or area encompassed by the candidate objects are generally close to the mean value and so the standard deviation (STD) values are also small. Preferably, the STD value is used as a boundary value to distinguish between candidate objects of interest in one or more spatially adjacent groups and/or in one or more spatially distant groups.

In a further preferred step, the morphological features and/or morphological pattern of the one or more candidate positive groups in the First Image is matched with the same morphological features and/or morphological pattern of the one or more candidate objects of interest in the Second Image to form a candidate negative group in the Second Image.

An additional step comprises the step of eliminating from the Second Image objects with non-matching morphological features and/or non-matching morphological patterns with the one or more candidate positive groups.

Finally, the quantitation of the level of expression of the candidate positive group is expressed as a percentage of the total number of candidate objects of interest in the candidate positive group and the candidate negative group.

In one preferred embodiment, as set out in Example 1, the morphological analysis of the segmented images in the First Image is described in more detail as follows:

The location of each candidate object of interest was determined using the x, and y co-ordinates for the one or more candidate objects of interest in the First Image;

The size of the area encompassed by the one or more candidate objects of interest is determined by using the major axis length and the minor axis length of the smallest ellipse containing the candidate object of interest;

The distance between the centre of the smallest ellipse containing each candidate object of interest and the centre of the smallest ellipse containing each neighbouring candidate object of interest is measured;

Using these measurements, the candidate objects of interest are segmented into at least two groups, these being, at least a spatially adjacent group comprising candidate objects of interest in close proximity to each other and at least a spatially distant group comprising candidate objects of interest which are spaced apart or far removed from each other;

This spatially adjacent group (known hereinafter as the candidate positive group) is defined by the following parameters which include but are not limited to:

Mean minimum and maximum distances between the centre of the smallest ellipse containing each candidate object of interest and the centre of the smallest ellipse containing each neighbouring candidate object of interest;

Mean minor axis length of the of the smallest ellipse containing the candidate object of interest;

Mean major axis length of the of the smallest ellipse containing the candidate object of interest;

Mean area encompassed by the spatially adjacent candidate objects of interest;

Number of positively stained candidate objects of interest; and optionally,

Mean degree of staining of the positively stained candidate objects of interest.

A morphological analysis of the segmented images in the Second Image is performed using similar processing steps. The morphological features and/or morphological pattern assimilated from the First Image are applied to the Second Image;

Any objects with matching morphological features and morphological patterns in the First Image and the Second Image are retained while any objects with non-matching morphological features and non-matching morphological patterns in the Second Image are eliminated from the Second Image.

In this regard, objects with non-matching morphological features and/or non-matching morphological patterns with the one or more candidate objects of interest in the candidate positive group are eliminated using a threshold analysis step. Using this step, a boundary is set on the area encompassed by the candidate positive group and/or the mean distance between the candidate objects of interest in the candidate positive group.

Preferably the boundary value (AREA_THRESH) defines the mean area encompassed by the candidate objects of interest candidate positive group.

Preferably the boundary value (DIST_THRESH) defines the mean distance between candidate objects of interest in the candidate positive group.

Preferably the boundary value (CONNECT_THRESH) defines the number of candidate objects of interest in the candidate positive group which are in close proximity to each other.

Once the boundaries are set, any parts (eg any objects) of the Second Image with boundary values which are above or below the thresholds which have been set, are eliminated. Preferably, the "boundary" is selected from the group consisting of a standard deviation (STD) value or a STD range value.

As used herein, the term "Standard Deviation (STD)" is a measure of the dispersion of a set of data from its mean. If the data points are closed to the mean, then the STD is small. If many data points are far from the mean, then the STD is large. If any or all of the data values are equal, then the STD is zero.

Preferably, the boundary value (AREA-STD) defines the standard deviation of the mean area encompassed by all of the candidate objects of interest in the candidate negative group. This boundary value is used in a threshold analysis step so that any parts or any objects with a value less than the AREA_STD value are eliminated from the Second Image.

Preferably, the boundary value (AREA_THRESH) is used in a threshold analysis step so that any objects with a value greater than the AREA_THRESH value are eliminated from the Second Image.

Preferably the objects with a value greater than an AREA_THRESH value include objects whose area is bigger than AREA_THRESH+2*AREA_STD.

Preferably the boundary value (DIST_THRESH) is used in a threshold analysis step so that any objects whose shortest distance between the centre of the objects is larger than the DIST_THRESH value are discarded.

Preferably the boundary value (CONNECT_THRESH) is used in a threshold analysis step so that any objects with a value less than the CONNECT_THRESH value are eliminated from the Second Image.

Finally, the level of expression of the one or more candidate objects of interest in the First Image is quantitated using the matching morphological features and/or morphological patterns of the one or more candidate objects in the First Image and the Second Image.

Quantitation of the Level of Expression

In the practice of the method of the present invention, the level of expression of the one or more candidate objects of interest, such as a target protein, in a biological sample is quantitated. That is, the level of expression of a candidate object of interest in a biological sample is determined by relating the amount and/or degree (such as intensity) of staining of the candidate positive group relative the degree of staining of the candidate positive group and the candidate negative group.

In one preferred embodiment, the total number of DAB positive cells corresponding with the positively stained candidate objects of interest and the total number of DAB negative cells corresponding with the negatively stained candidate objects of interest is determined, the non-tumour cells having been eliminated. The level of expression of the DAB positive cells is thus expressed as a percentage of the total number of DAB positive and DAB negative cells Computer Implementation As discussed above, an initial step in automating microscopic inspection is to create a virtual slide, that is, a high resolution digital image of a slide.

As used herein, the term "automated" means computer-aided. Aspects of the invention may be implemented in hardware or software, or a combination of both. However, preferably, the image analysis method of the present invention is implemented in one or more computer programs encoded in a computer readable medium and executing on one or more programmable computers. Output information generated upon execution of the computer program(s) is transmitted to one or more computer output devices, in a known fashion.

In preferred embodiments, specific staining of one or more candidate objects of interest is detected, measured and quantitated using image analysis equipment, defined herein as comprising a light or a fluorescence microscope, and image-transmitting camera and a view screen, most preferably also comprising a computer that can be used to direct the operation of the device and also store and manipulate the information collected, most preferably in the form of an optical image of certain regions of a stained tissue preparation. Image analysis devices useful in the practice of this invention include but are not limited to the CAS 200 system (Becton Dickenson, Mountain View, Calif.) and Aperio systems.

In one preferred embodiment, the system comprises a server that maintains or has access to application software which when executed performs a plurality of image processing and analysis steps. Preferably, the server additionally has access to a plurality of virtual slides. The server executes a selected routine on an identified virtual slide and provides as output the resulting data. The virtual slide can be accessed locally or remotely across a network. Similarly, the image processing routines can be obtained from local storage or across a network, or both. Advantageously, certain common routines may be stored locally for inclusion in other local or remotely obtained routines.

Utility of the Invention

The image analysis method and the system for implementing the image analysis method of the present invention have wide applications in the diagnosis, prevention, treatment and prognosis of different disease states. In this regard, the invention has utility in the field of oncology for the detection of disease states which include but are not limited to: melanoma, leukemia, breast cancer, colon cancer, prostate cancer, cervical tissue cancer, bladder cancer, lung cancer, ovarian cancer and colorectal cancer.

One particular application is in the field of abnormal cell growth and proliferation. It is known in the art that a number of cellular proteins are related to cell proliferation and cell signaling. Many of these proteins are critical for normal cell growth but may also be responsible for abnormal cell growth. By way of example, the hormones estrogen and progesterone send signals through their respective nuclear receptors to stimulate responsive breast cancer cells to grow. After a breast cancer is removed, the cancer cells are tested to see if they have hormone receptors. Presence of each one of these markers is used clinically to predict the likelihood of response to hormonal therapies. As the Examples demonstrate, the invention provides an automated image analysis method and a system for implementing the image analysis method for the immunohistochemical (IHC) analyses of estrogen receptor (ER) and progesterone receptor (PR) in a large number of patient samples.

Whilst the detection of the relative presences within a tumour of cancerous cells expressing ER and/or PR and cancerous cells not expressing these proteins is a specific example of how the present invention has utility, it also has comparable utility in assessing other tumours for which biomarkers are available. One common phenomenon displayed by tumours is that they show heterogenous characteristics. This applies both between individual cells; between individual clumps of cells in the same tumour mass; between individual tumour masses in the same patient; and between tumour masses of the same general type in different patients. The invention enables the diagnostic method to be fine tuned so that an accurate individual assessment can be made for each cancer-tissue biopsy harvested for any individual biomarker.

The image analysis method and the system for implementing the image analysis method of the present invention also has utility in the field of oncology for the early detection of minimal residual disease ("micrometastases") and metastatic recurring disease (MM/MRD). Metastasis is the biological process whereby a cancer spreads to the distant part of the body from its original site. A micrometastases is the presence of a small number of tumour cells particularly in the lymph nodes and bone marrow. For patients with tumours, a key question is whether cancer cells are metastasizing, that is, breaking free from the tumour and traveling to other areas of the body through the bloodstream. The desirability of analyzing lymph nodes of cancer patients for micrometastatic (tumour) cells is well established, both as an indicator of patient prognosis and as a possible guide as to the advisability of treatment with adjuvant therapy (chemotherapy/hormones). Micrometastasis is a practically useful rare-event finding application that can benefit greatly from the systems and methods of the present invention. A particular application is the detection of micrometastatic (tumour) cells in lymph nodes, but the invention can be used for many applications, especially when large numbers of samples need to be processed.

The image analysis method and the system for implementing the image analysis method of the present invention also has utility in the field of oncology for the detection of Micrometastases/Metastatic Recurring Disease (MM/MRD). A metastatic recurring disease is similar to micrometastasis, but is detected after cancer therapy rather than before therapy. An immunohistochemical assay for Micrometastases/Metastatic Recurring Disease (MM/MRD) is performed using a monoclonal antibody which reacts with an antigen (a metastatic-specific mucin) found in bladder, prostate and breast cancers.

In one preferred embodiment, the image analysis method and the system for implementing the image analysis method of the present invention has utility for the detection of cervical cancer. Cervical cancer is characterized by a cervical dysplasia which refers to the replacement of the normal or metaplastic epithelium with atypical epithelial cells that have cytologic features that are pre-malignant (nuclear hyperchromatism, nuclear enlargement and irregular outlines, increased nuclear-to-cytoplasmic ratio, increased prominence of nucleoli (a nucleolius is an organelle in a cell nucleus) and chromosomal abnormalities. The changes seen in dysplastic cells are of the same kind but of a lesser degree than those of frankly malignant cells. In addition, there are degrees of dysplasia (mild, moderate, severe).

Other applications of the image analysis method and the system for implementing the image analysis method of the present invention which are within the scope of the invention, include but are not limited to analyses for HER2 (neu), and the epidermal growth factor receptor (EGFR), and signal transduction receptors (such as, for example, PI3K/Akt, MAPk, and JUN kinase), MIB-I, Microvessel density analysis, the oncogene p53, immunophenotyping, haematoxylin/eosin (H/E) morphological analysis, undifferentiated tumour classification, antibody titering, prominence of nucleoli, HIV p24, human papiloma virus (HPV; for cervical biopsy), and mitotic index. Generally speaking, any diagnostic method utilizing IHC or the like staining techniques is within the scope of the present invention.

HER2 (neu) is a growth factor receptor and when found within tumour cells amounts to an aggressively growing tumour. Studies have determined that there is a significantly decreased disease-free survival and overall survival of a patient with over-expression of HER2. Before an oncologist prescribes an anti-HER2/neu therapeutic agent, an immunohistochemistry (IHC) assessment for HER2/neu is desirable. Three general methods are currently available for the detection of HER2/neu: genetic detection, protein expression, and protein activity. In-situ hybridization methods are typically used for HER2/neu genetic detection. IHC methods are used for the assessment of HER2/neu protein expression. Therapeutic availability increases the need for a standard methodology for assessing the expression of HER2/neu.

MIB-1 is an antibody that can be used in IHC assays for the antigen Ki-67. The clinical stage at first presentation is related to the proliferative index measured with Ki-67. High index values of Ki-67 are positively correlated with metastasis, death from neoplasia, low disease-free survival rates, and low overall survival rates.

Microvessel density analysis is a measure of new blood vessel formation (angiogenesis). Angiogenesis is characteristic of growing tumours. Intratumour microvessel density can be assessed by anti-CD34 immunostaining.

Overexpression of the p53 oncogene has been implicated as the most common genetic alteration in the development of human malignancies. Investigations of a variety of malignancies, including neoplasms of breast, colon, ovary, lung, liver, mesenchyme, bladder and myeloid, have suggested a contributing role of p53 mutation in the development of malignancy. The highest frequency of expression has been demonstrated in tumours of the breast, colon and ovary. A wide variety of normal cells do express a wildtype form of p53 but generally in restricted amounts. Overexpression and mutation of p53 have not been recognized in benign tumours or in normal tissue. An immunohistochemical assay of p53 is available and uses an anti-p53 antibody, for example the well-characterized DO-7 clone.

In virtual microscopy, the image analysis method and the system for implementing the method are suitable for tissue identification, such as locating regions of analysis for IHC assays, and rapid screening of tissue samples, such as histology sections arranged as tissue microarrays (TMAs). Other useful applications include but are not limited to prenatal diagnosis of fetal cells in maternal blood and in the field of infectious diseases to identify pathogens and viral loads, alkaline phosphatase assessments, reticulocyte counting, and others which include but are not limited to nuclei counting, cell scoring, determination of: mitotic index, live/dead cells, cell health, granularity, angiogenesis tube formation, neurite outgrowth, cell cycle, monopole detection, cell proliferation, cell migration (such as, for example, in response to a foreign antigen in the lung), cell nuclei counting, cell scoring, identification of sub-populations of cells tagged with a second probe (ie co-localisation and double labeling), single marker quantification, pathway analysis, adipogenesis, fatty vacuole determination in liver, targeting cells in active mitosis using commercially available markers for M phase, apoptosis (distinguishing between live and dead cells), cell proliferation, cell death, lack of cell death associated with cancer, premature cell death associated with neuromuscular disease (Alzheimers, Parkinsons), Cytotoxicity and Apoptosis, Cell Health, Classification of cells into four classes (Viable, Early apoptotic, late apoptotic, and necrotic), Granularity, Detection of granules, Optional nuclear marker for normalized counts, GPCR internalization, Assays of clustering target molecules, Angiogenesis Tube Formation, Measuring and characterizing endothelial tube formation (a model system for angiogenesis), Promotion or inhibition of blood vessel formation, Relevant for cancer, diabetes and other vascular disease research, Neurite Outgrowth, Measuring and characterizing outgrowths (length and branching) (filaments and cell bodies), Useful in the study of neurodegenerative disease such as Alzheimer's and Parkinson's, Neurodegenerative research (eg spinal cord research), Cell differentiation (eg stem cell research), Cell Cycle analyses, Cancer Research, Nuclear stain provides DNA content and average intensity indicates mitosis—5 classifications of cell cycle stage, Optional mitosis-specific staining, Optional apoptosis staining, Monopole Detection, Cancer research, Disruption of normal bipolar spindle formation, Disruption of centrosome separation (e.g. using monastrol), Classification of cells as interphase, bipole or monopole. If the method is used to quantitate EGFR in various cell lines, then images analysis methodology would be used to determine the number of receptors per cell.

As regards neutrophil detection, certain white blood cells known as neutrophils may be stained with Fast Red, a commonly known stain, to identify alkaline phosphatase in the cytoplasm of the cells. To further identify these cells and the material within them, the specimen may be counterstained with hematoxylin to identify the nucleus of the cells. In cells so treated, the cytoplasm bearing alkaline phosphatase becomes a shade of red proportionate to the amount of alkaline phosphatase in the cytoplasm and the nucleus becomes blue. However, where the cytoplasm and nucleus overlap, the cell appears purple. These color combinations appear to preclude the finding of a focused Z position using the focus processes discussed above. Other useful applications include prenatal diagnosis of fetal cells in maternal blood and in the field of infectious diseases to identify pathogens and viral loads, alkaline phosphatase assessments, reticulocyte counting, and others.

Whilst the present invention is described herein by way of example with particular reference to ER and/or PR as biomarkers, it will be appreciated that other biomarkers and combinations of biomarkers can equally be utilized in accordance with the principles of the invention as set out herein. Reference is made to generation and manipulation of a First Image and a Second Image and it will be apparent to the skilled person having the advantage of knowledge of the invention described herein that third and subsequent images may be added to the invention depending on the particular biomarkers or combination of biomarkers indicated by a clinician or otherwise for analysis in any particular case. The present invention includes such further applications within its scope.

Automated detection of nuclear proteins can be applied in many areas in addition to use of ER and PR as biomarkers in breast cancer diagnosis. For example, the ER and PR biomarkers are also useful for other cancer types such as ovarian and endometrial cancer (Takeshima et al. 2008, *Am J Clin Pathol* 130(5): 771-9: Soslow 2008, *Int J Gynecol Pathol* 27(2): 161-74: and Hogdall, et al. 2007, *Oncol Rep* 18(5): 1051-9).

In addition biomarker p53 IHC is used as a biomarker for ovarian cancer (Darcy et al. 2008, *Gynecol Oncol*—111(3): 487-95), endometrial cancer (Steinbakk et al. 2008, *Am J Obstet Gynecol*—October 29. [Epub ahead of print]) head and neck cancer (Schumaker et al. 2008, *Clin Cancer Res* 14(18): 5877-83) and colorectal cancer (Lan et al. 2007, *Int J Colorectal Dis* 22(5): 499-506 and Resnick et al. 2004, *Clin Cancer Res* 10(9): 3069-75). Also biomarker Ki-67, a marker of proliferation, is used in a wide variety of different tumour types.

Another area that the present invention is applicable to is the diagnosis of inherited cancer syndromes. It may be possible to decrease the number of patients who require mutation analysis by profiling tumors of their family members using IHC. This would be of particular importance for BRCA1 and BRCA2 in breast and ovarian cancer. Both BRCA1 and BRCA2 are nuclear proteins which can be quantified using the method of the present invention. Also, loss of BRCA2 expression may be a predictor of response to PARP inhibitors in breast and ovarian cancer (Edwards et al. 2008, *Nature* 451(7182): 1111-5), outlining another application of the present invention. An additional application of the present invention is to quantify mismatch repair genes in colorectal cancer as a marker of microsatellite instability and HNPCC (heriditary nonpolyposis colorectal cancer) namely MLH1, MLH2 and MSH6 (Muller et al. 2006, *Int J Colorectal Dis* 21(7): 632-41 and Hendriks et al. 2003, *Am J Pathol* 162(2): 469-77).

Application of the invention to non-malignant diseases is also envisaged. For example, detection of a nuclear signal in ulcerative colitis specimens is possible. The identification of new biomarkers to predict disease progression and treatment response in inflammatory bowel disease will enable the application of personalized treatment protocols and the quantification of nuclear IHC signal may play a role in this.

Other aspects of the present invention are presented below by way of numbered paragraphs which include:

1. A method for the analysis of an image of a biological sample comprising one or more candidate objects of interest, comprising the steps of:

obtaining an image of the biological sample;

separating the image of the biological sample into a First Image and a Second Image;

assimilating the morphological features and/or morphological pattern of the one or more candidate objects of interest in the First Image;

applying to the Second Image the morphological features and/or morphological pattern assimilated from the First Image;

eliminating from the Second Image objects with non-matching morphological features and/or non-matching morphological patterns with the one or more candidate objects of interest in the First Image; and quantitating the level of expression of the one or more candidate objects of interest in the First Image using the matching morphological features and/or morphological patterns of the one or more candidate objects in the First Image and the Second Image.

2. The method of paragraph 1 wherein the First Image and the Second Image are optically enhanced.

3. The method according to paragraphs 1 or 2 wherein the First Image and the Second Image are optically enhanced by transforming substantially all of the First Image and the Second Image from a first colour space to a second colour space.

4. The method of any one of paragraphs 1-3 wherein the morphological features and/or morphological pattern of the one or more of the candidate objects of interest in the First Image is assimilated by measuring the distance between the candidate objects of interest and then grouping the candidate objects of interest into at least a first spatially adjacent group and a second spatially distant group such that the mean distance between and the mean area encompassed by the candidate objects of interest in the one or more spatially adjacent group represents a candidate positive group.

5. The method of paragraph 4 wherein the morphological features and/or morphological pattern of the one or more candidate positive groups in the First Image is matched with the same morphological features and/or morphological pattern of the one or more candidate objects of interest in the Second Image to form one or more candidate negative groups in the Second Image.

6. The method of paragraph 5 further comprising the step of eliminating from the Second Image objects with non-matching morphological features and/or non-matching morphological patterns with the one or more candidate positive groups.

7. The method of any one of paragraphs 4-6 wherein the quantitation of the level of expression of the candidate positive group is expressed as a percentage of the total number of candidate objects of interest in the candidate positive group and the candidate negative group.

8. The method of any one of paragraphs 1-7 wherein the one or more candidate objects of interest is/are detected by immunochemistry.

9. The method of any one of paragraphs 1-7 wherein the one or more candidate objects of interest is/are detected by a stain.

10. The method of any one of paragraphs 1-8 wherein the one or more candidate objects of interest is/are detected by a combination of immunohistochemistry and a stain.

11. The method of paragraph 9 or paragraph 10 wherein the stain is a protein stain.

12. The method of any one of paragraphs 1-11 wherein the biological sample is selected from the group consisting of a tissue sample, a tissue section, a tissue microarray and a cellular sample.

13. The method according to any one of paragraphs 1-12 wherein the biological sample is a tumour cell or tissue sample.

14. A method for the automated analysis of an image of a biological sample comprising one or more candidate objects of interest comprising the steps of:

obtaining an image of the biological sample;

separating the image of the biological sample into a First Image and a Second Image;

assimilating the morphological features and/or morphological pattern of the one or more candidate object of interest in the First Image;

applying to the Second Image the morphological features and/or morphological pattern assimilated from the First Image;

eliminating from the Second Image objects with non-matching morphological features and/or non-matching morphological patterns with the one or more candidate objects of interest in the First Image; and quantitating the level of expression of the one or more candidate objects of interest in the First Image using the matching morphological features and/or morphological patterns of the one or more candidate objects in the First Image and the Second Image.

15. The method of paragraph 14 wherein the image is a digital image.

16. The method of paragraph 14 or paragraph 15 wherein the method is as defined in any one of paragraphs 2-13.

17. A computer program stored on a computer-readable medium, for an automated image analysis of a biological sample, the computer program comprising instructions for causing a computer to: process a biological sample comprising one or more candidate objects of interest; obtain an image of the biological sample; separate the image of the biological sample into a First Image and a Second Image; assimilate the relevant morphological features and/or morphological pattern of the one or more candidate objects of interest in the First Image; apply to the Second Image the morphological features and/or morphological pattern assimilated from the First Image; eliminate from the Second Image objects with non-matching morphological features and/or non-matching morphological patterns with the one or more candidate objects of interest in the First Image; and quantitate the level of expression of the one or more candidate objects of interest in the First Image using the matching morphological features and/or morphological patterns of the one or more candidate objects in the First Image and the Second Image.

18. A computer comprising a computer program as defined in the previous paragraph.

19. An apparatus for quantification of one or more candidate objects of interest in a biological sample comprising means for obtaining an image of the biological sample;

means for separating the image of the biological samples into a First Image and a Second Image;

means for assimilating the morphological features and/or morphological pattern of the one or more candidate objects of interest in the First Image;

means for applying to the Second Image the morphological features and/or morphological pattern assimilated from the First Image;

means for eliminating from the Second Image objects with non-matching morphological features and/or non-matching morphological patterns with the one or more candidate objects of interest in the First Image; and means for quantitating the level of expression of the one or more candidate objects of interest in the First Image using the matching morphological features and/or morphological patterns of the one or more candidate objects in the First Image and the Second Image.

20. An automated system for quantification of one or more candidate object of interest in a biological sample comprising:
means for obtaining an image of the biological sample;
means for separating the image of the biological samples into a First Image and a Second Image;
means for assimilating the morphological features and/or morphological pattern of the one or more candidate objects of interest in the First Image;
means for applying to the Second Image the morphological features and/or morphological pattern assimilated from the First Image;
Means for eliminating from the Second Image objects with non-matching morphological features and/or non-matching morphological patterns with the one or more candidate objects of interest in the First Image; and
means for quantitating the level of expression of the one or more candidate objects of interest in the First Image using the matching morphological features and/or morphological patterns of the one or more candidate objects in the First Image and the Second Image.

21. A method for determining the level of expression of one or more candidate objects of interest in a biological sample, wherein the method comprises:
immunohistochemically staining the biological sample;
obtaining an image of the biological sample;
separating the image of the biological sample into a First Image and a Second Image;
assimilating the relevant morphological features and/or morphological pattern of the one or more candidate objects of interest in the First Image;
applying to the Second Image the morphological features and/or morphological pattern assimilated from the First Image;
eliminating from the Second Image objects with non-matching morphological features and/or non-matching morphological patterns with the one or more candidate objects of interest in the First Image; and
quantitating the level of expression of the one or more candidate objects or areas of interest in the First Image using the matching morphological features and/or morphological patterns of the one or more candidate objects in the First Image and the Second Image.

22. The method of paragraph 21 wherein the one or more candidate objects of interest is/are expressed in tumour cells.

23. The method of paragraph 22 wherein the one or more candidate objects of interest is/are expressed in a nucleus of a tumour cell.

24. The method of paragraph 22 or paragraph 23 wherein the one or more candidate objects of interest is/are selected from the group consisting of an Estrogen Receptor (ER) and/or a Progesterone Receptor (PR).

25. The method of any one of paragraphs 21-24 wherein the image of the biological sample is obtained by scanning the biological sample.

26. A system for processing a digital image comprising an image processing method comprising the steps for processing a digital image as set out in any one or more of the FIGS. 6, 7, 8 and 9.

27. The method according to any one of paragraphs 21-25 or the system as defined in paragraph 26 wherein the method or the system is an automated (computer-aided) method or system.

28. The method or the system according to paragraph 27 wherein the method or the system is a completely automated (computer-aided) method or system.

29. A method or a system or an apparatus substantially as described herein and with reference to the description and/or the accompanying Figures.

Aspects of the invention will be apparent by reference to the appended claims.

As used herein, obtaining an image of a biological sample may refer to using a pre-prepared image or to generating a new image de-novo. In appropriate cases, this may mean taking an image created in the standard manner and digitising it or otherwise transferring it to render it suitable for use in the method, system or apparatus of the present invention.

EXAMPLES

The invention is now further described only by way of the following examples in which reference is made to the following Figures in which:

FIGS. 3A to 3H are graphs showing ER and PR histocore correlation of data for tissue cohort II of FIGS. 2B and 2C;

FIGS. 5A to 5D are graphs showing the RFC and tamoxifen response;

FIGS. 7A and 7B are flow diagrams showing in further detail the first, second and fourth steps of the image analysis method shown in FIG. 6A;

FIG. 8A is a flow diagram showing in further detail the third step of the image analysis method shown in FIG. 6A

FIGS. 11A to 11C show the correlation between manual and automated scoring for biomarker P53 in bladder tumor tissue;

All of the original Figures with images of tissue staining in colour, were submitted at the Receiving Office on the filing date of this International application. These colour images may also be obtained from the following links.
http://www.ucd.ie/gallagherlab/members/elton/pct_figures/fig1_a_col.tif
http://www.ucd.ie/gallagherlab/members/elton/pct_figures/fig1_b_col.tif
http://www.ucd.ie/gallagherlab/members/elton/pct_figures/fig1_c_col.tif
http://www.ucd.ie/gallagherlab/members/elton/pct_figures/fig1_d_col.tif
http://www.ucd.ie/gallagherlab/members/elton/pct_figures/fig1_e_col.tif
http://www.ucd.ie/gallagherlab/members/elton/pct_figures/fige_d_col.tif
http://www.ucd.ie/gallagherlab/members/elton/pct_figures/fig1_b_col.tif
http://www.ucd.ie/gallagherlab/members/elton/pct_figures/fig6_b_col.tif
http://www.ucd.ie/gallagherlab/members/elton/pct_figures/fig12_a_col.tif
http://www.ucd.ie/gallagherlab/members/elton/pct_figures/fig12_b_col.tif
http://www.ucd.ie/gallagherlab/members/elton/pct_figures/fig12_c_col.tif
http://www.ucd.ie/gallagherlab/members/elton/pct_figures/fig12_d_col.tif
http://www.ucd.ie/gallagherlab/members/elton/pct_figures/fig13_a_col.tif
http://www.ucd.ie/gallagherlab/members/elton/pct_figures/fig13_c_col.tif
http://www.ucd.ie/gallagherlab/members/elton/pct_figures/fig13_d_col.tif
http://www.ucd.ie/gallagherlab/members/elton/pct_figures/fig13_e_col.tif
http://www.ucd.ie/gallagherlab/members/elton/pct_figures/fig13_f_col.tif
http://www.ucd.ie/gallagherlab/members/elton/pct_figures/fig15_a_col.tif
http://www.ucd.ie/gallagherlab/members/elton/pct_figures/fig15_b_col.tif
http://www.ucd.ie/gallagherlab/members/elton/pct_figures/fig8_b_col.tif
http://www.ucd.ie/gallagherlab/members/elton/pct_figures/fig9_b_col.tif
http://www.ucd.ie/gallagherlab/members/elton/pct_figures/fig13_b_col.tif Example 1

Figure 6A:
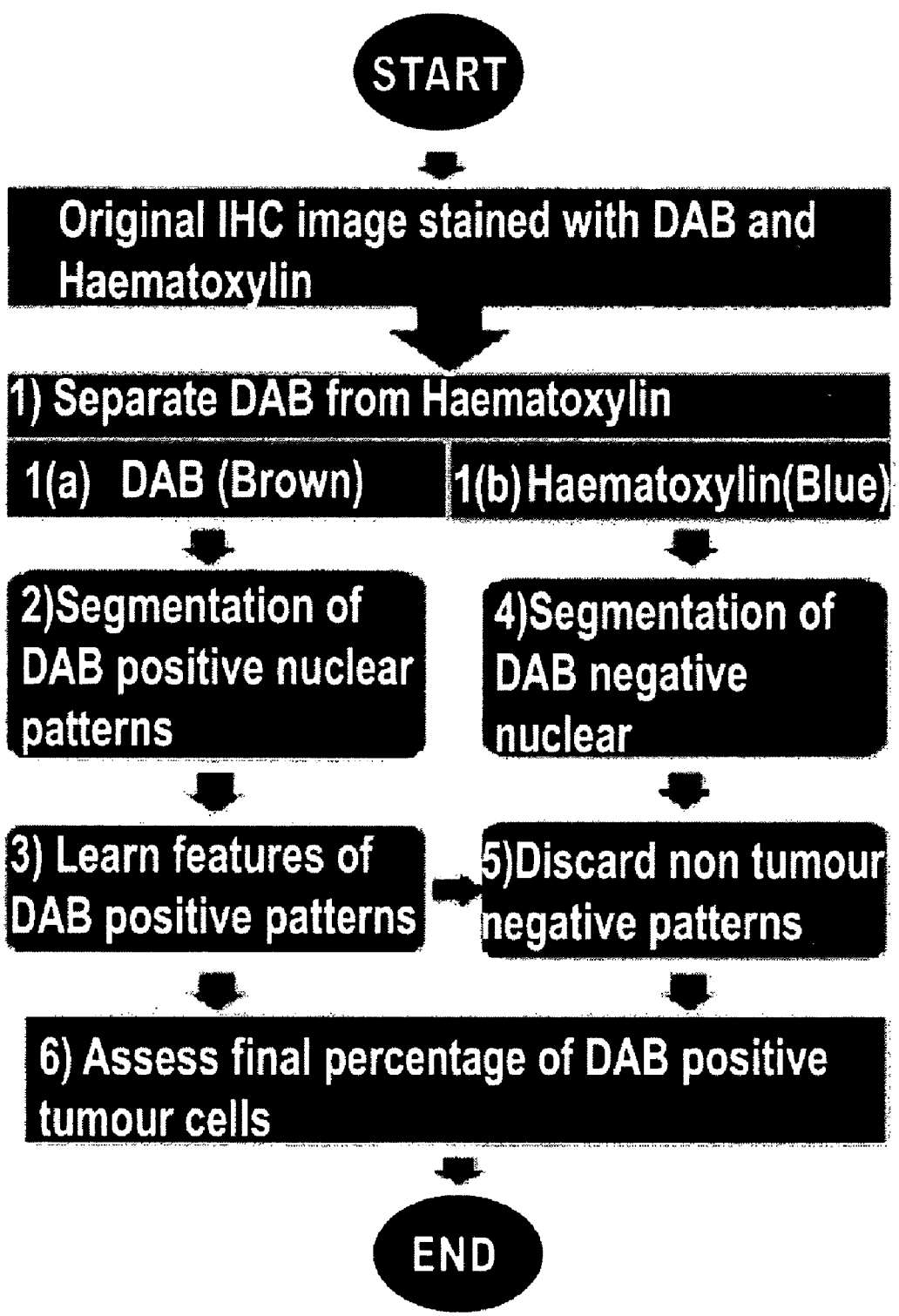
FIG. 6A is a flow diagram showing steps 1 to 6 performed in the image analysis method according to an embodiment of the present invention.

In one specific Example, the steps of the Image Analysis Method of the present invention are shown in the flow diagram of FIG. 6A. The images output following performance of each step of the method are shown in FIG. 6B.

The method proceeds in 6 steps, which are described with reference to FIGS. 6A and 6B as follows:
Step 0=Original IHC image is stained with DAB and haematoxylin (the result of which is shown as image 0 in FIG. 6B)
Step 1 (including steps 1(a) and 1(b))=Separation of DAB from haematoxylin (resulting in image 1(a) in FIG. 6B (shows DAB staining) and image 1(b) in FIG. 6B (shows haematoxylin staining).
Step 2=Segmentation of DAB positive nuclear patterns (shown as image 2 in FIG. 6B)
Step 3=Extraction of DAB nuclei and an explanation of how the morphological analysis is described mathematically (shown as image 3 in FIG. 6B)
Step 4=Segmentation of DAB negative nucleic patterns (shown as image 4 in FIG. 6B)
Step 5=Extraction of DAB negative nuclei (the step indicated by the reference numeral 5 in FIG. 6B)
Step 6=Determination of level of expression of the biomarker (the step indicated by the reference numeral 6 in FIG. 6B).

Figure 1A:
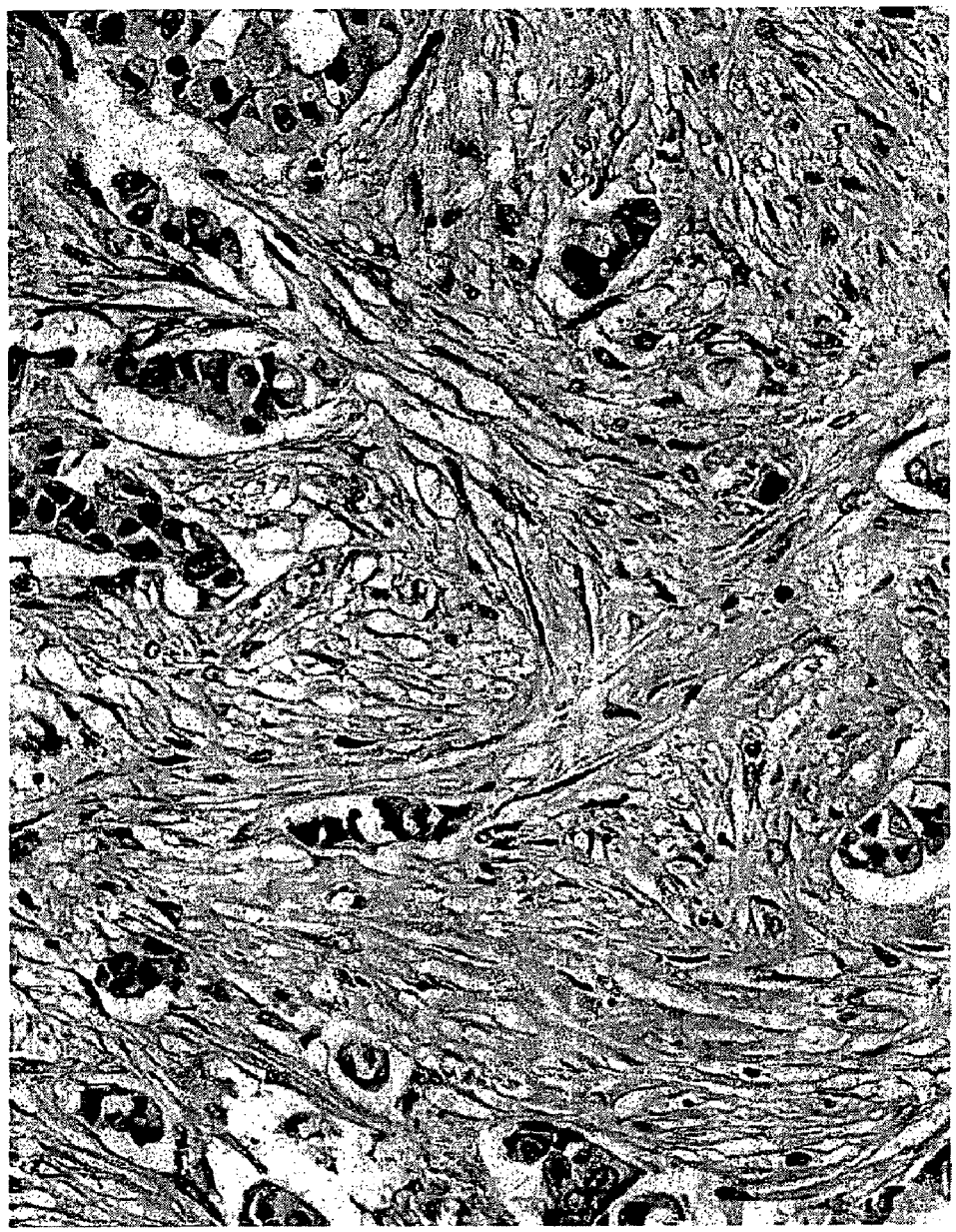
FIGS. 1A to 1F are 500×500 pixel images of a section of tissue illustrating an image analysis method according to an embodiment of the present invention.
Figure 1B:
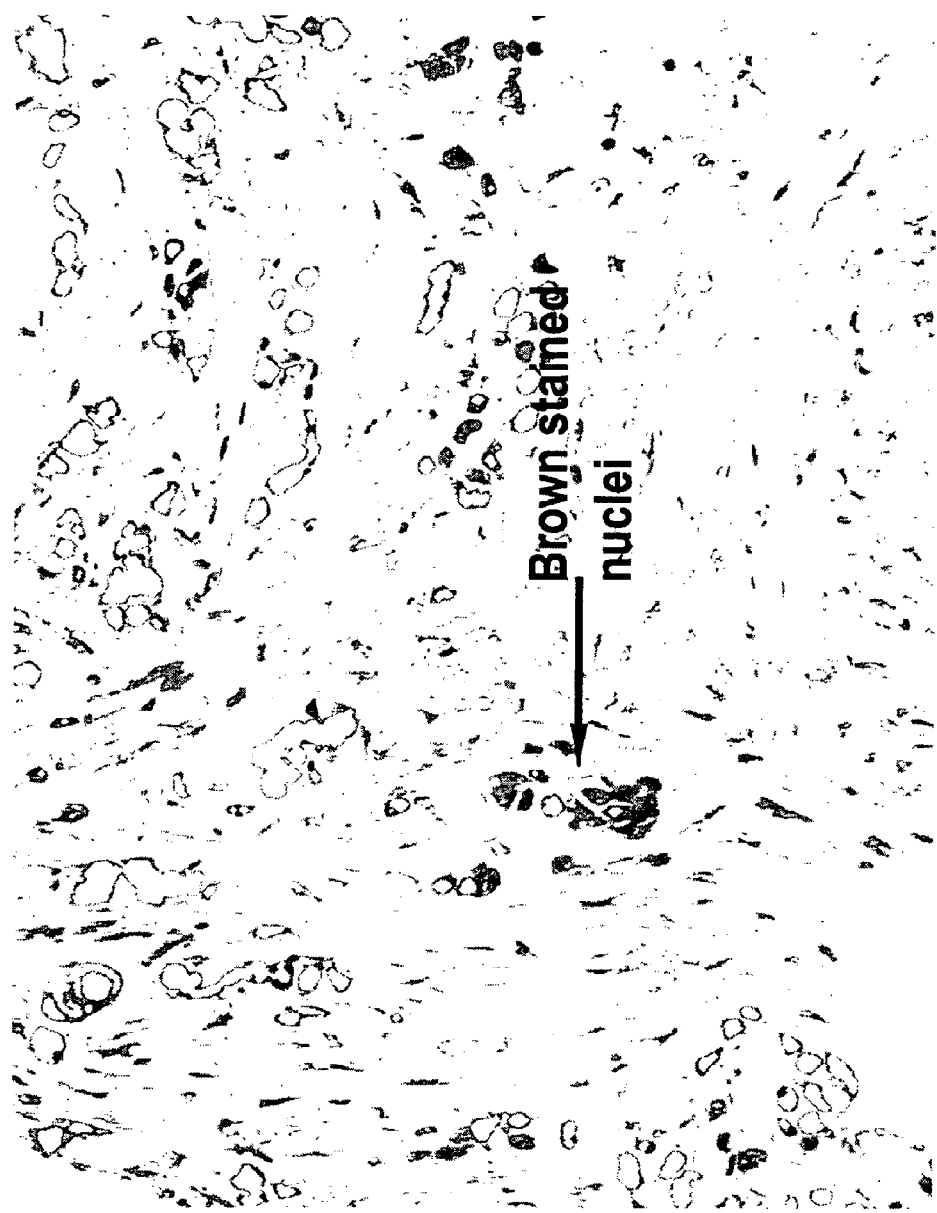
Figure 1C:
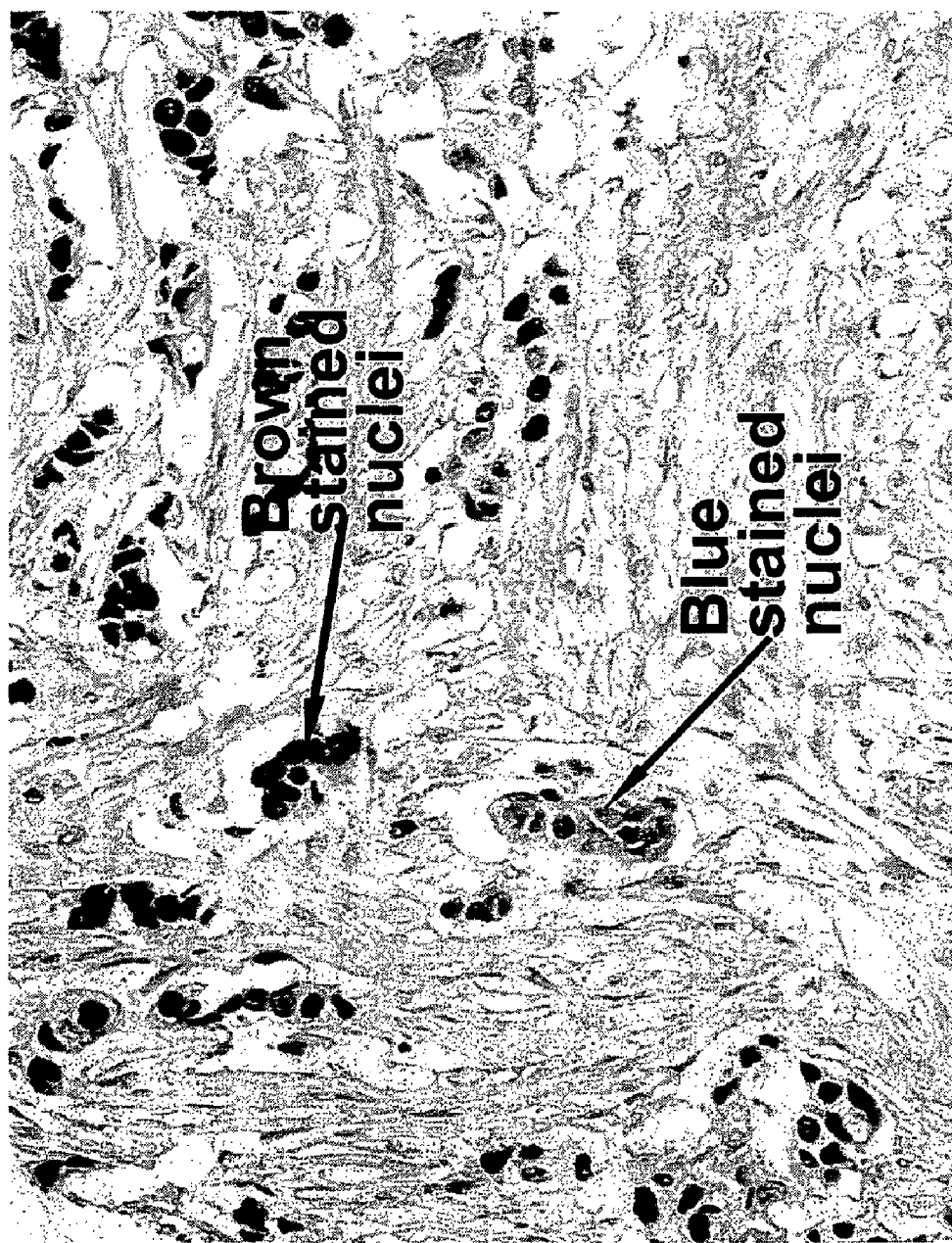
Figure 1D:
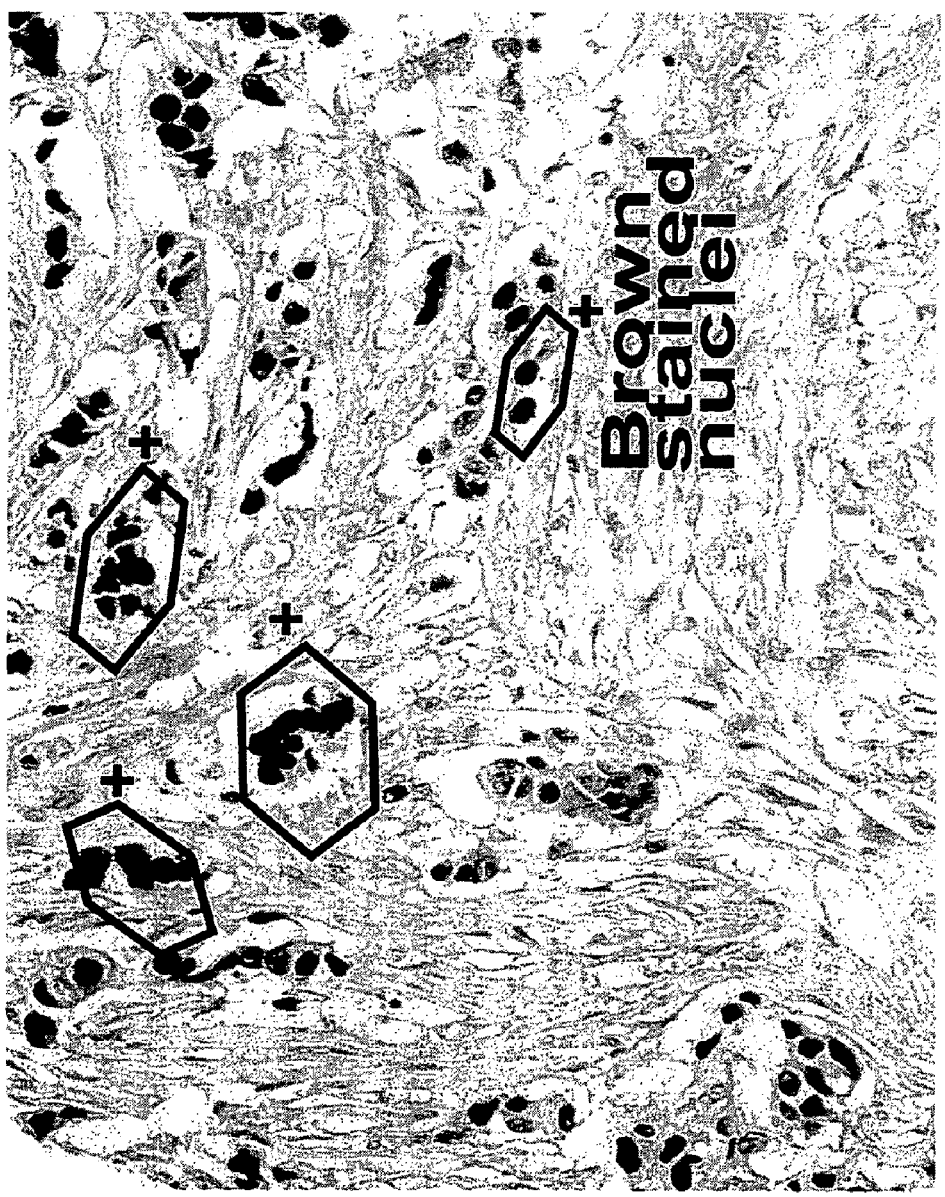
Figure 1E:
Figure 1F:
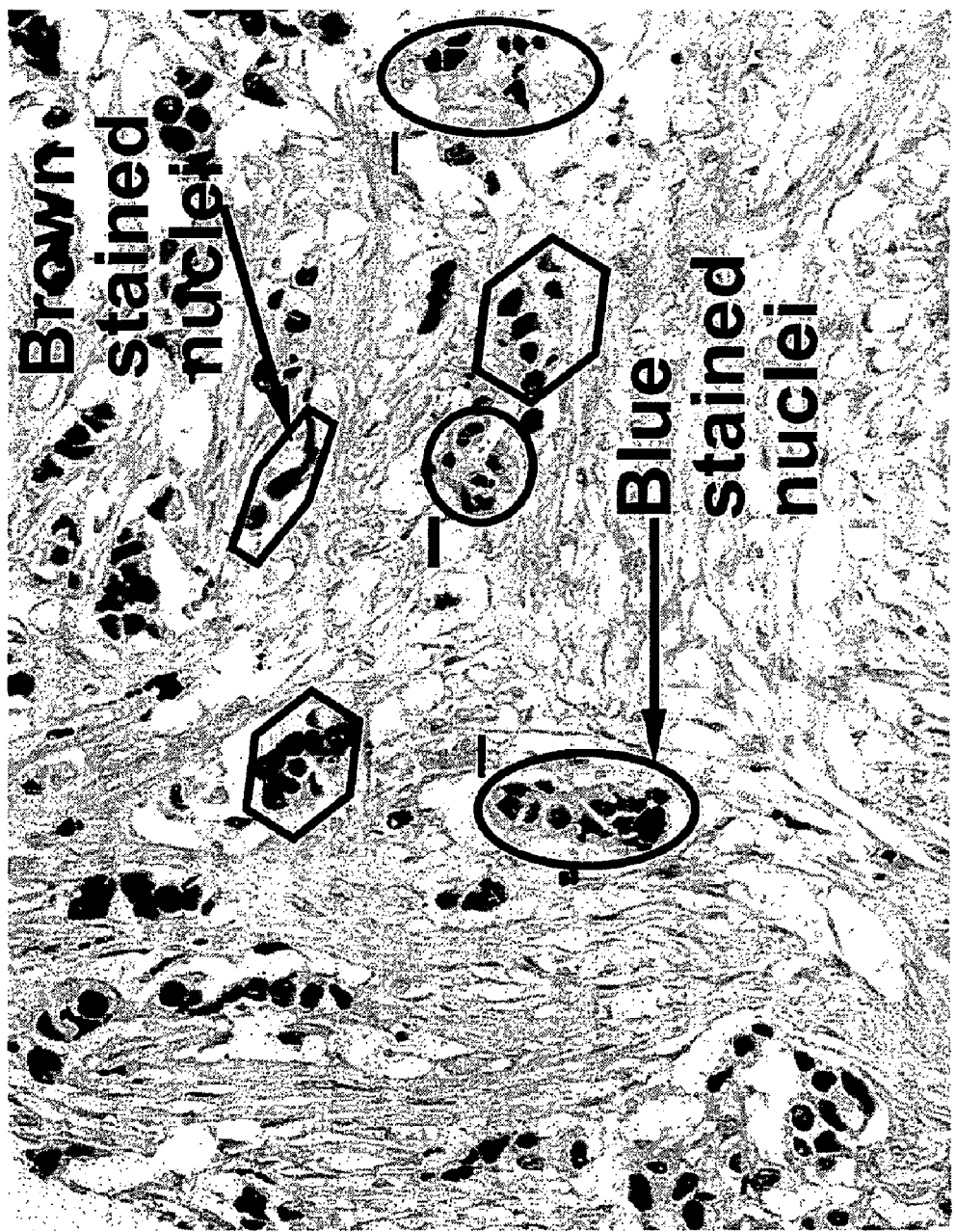
Figure 6B:
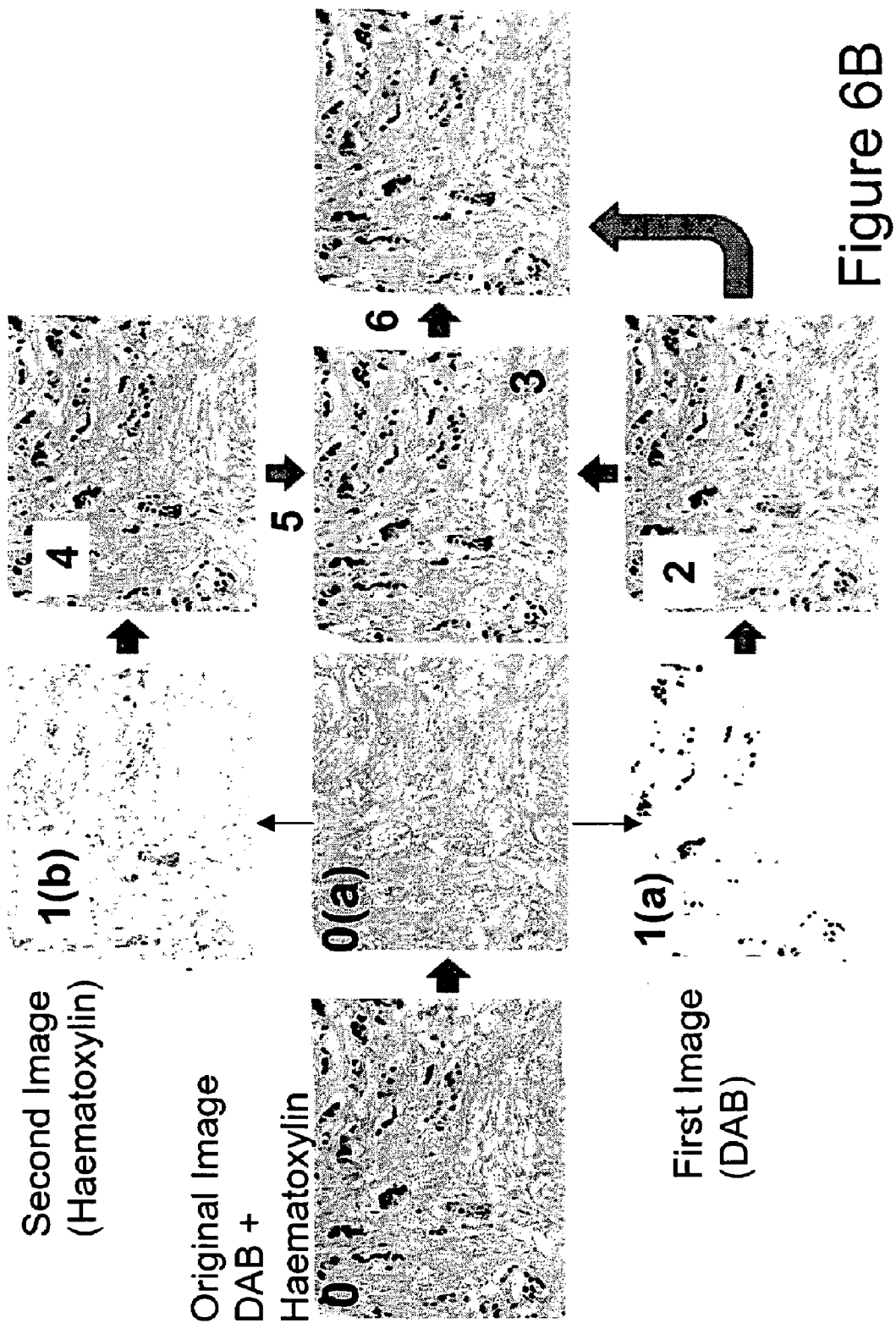
FIG. 6B shows 500×500 pixel digital images of a section of tissue, in which each image shows the output after performance of each step of the image analysis method shown in FIG. 6A.

The images shown in FIGS. 1A to 1F are of the same section of tissue illustrated in FIG. 6B and provide a further example showing the output after each step of the method. FIG. 1C shows an original immunohistochemistry (IHC) section. FIG. 1A shows an equivalent H&E (haematoxylin and eosin) section. FIG. 1E shows the original IHC section of FIG. 1C after the removal of DAB-negative tumour nuclei, thus showing brown stained DAB-positive tumour nuclei. FIG. 1B shows the original IHC section of FIG. 1C after the extraction of DAB-positive tumour nuclei, thus showing blue stained DAB-negative tumour nuclei. FIG. 1D shows the original IHC section of FIG. 1C in which a selection of brown stained DAB-positive tumour nuclei are shown circled, labeled with a '+' symbol. In practice, such brown stained tumour nuclei may appear as red stained tumour nuclei. FIG. 1F shows the original IHC section of FIG. 1C in which a selection of brown stained DAB-positive tumour nuclei are shown circled, labeled with a '+' symbol and blue stained DAB-negative tumour nuclei are shown circled, labeled with a '−' symbol.

Figures 1, 10A:
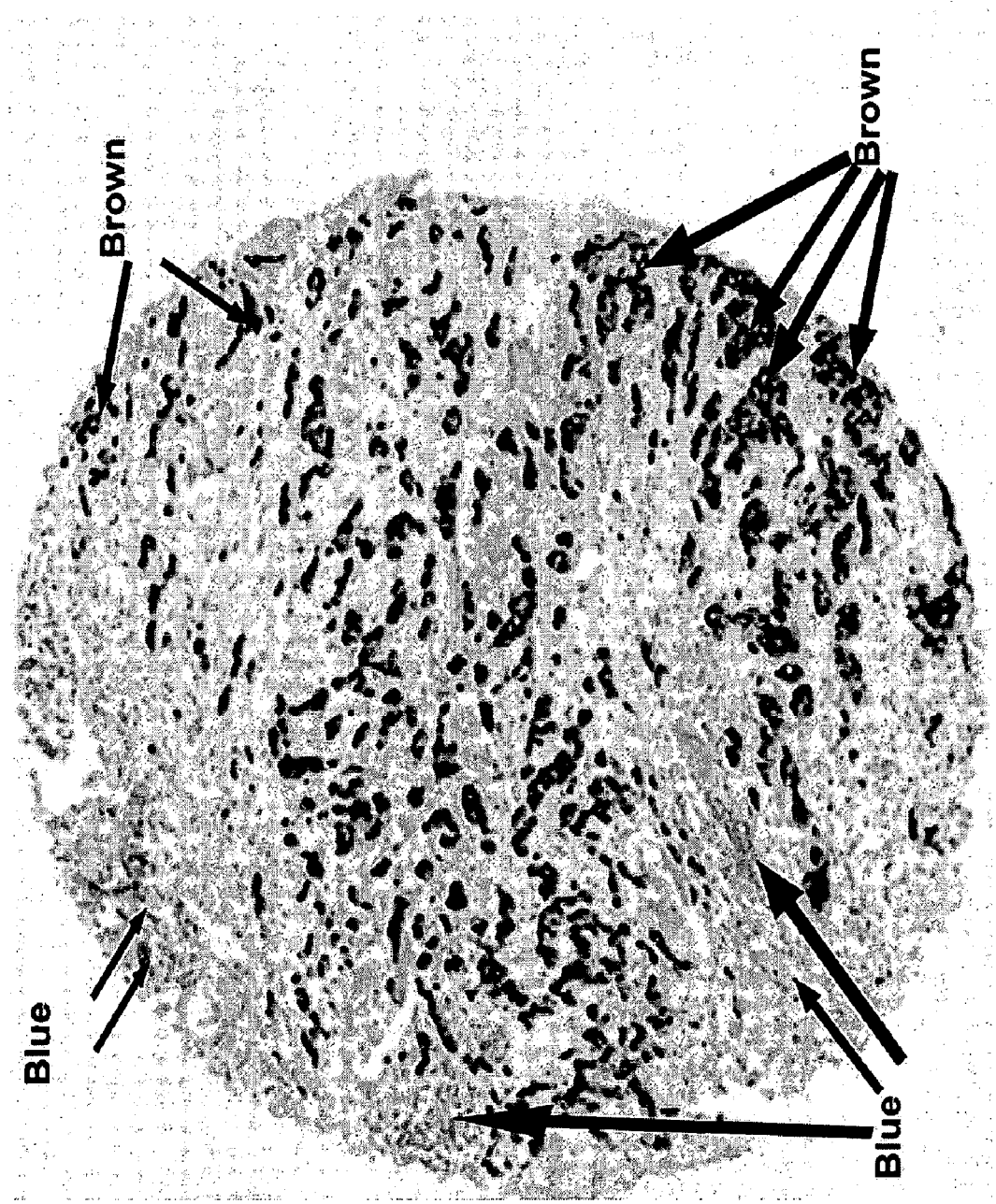
FIGS. 10A-1, 10A-2, 10B-1 and 10B-2 are 500×500 pixel digital images showing two stained tissue cores before and after pattern recognition processing.
Figures 2, 10A:
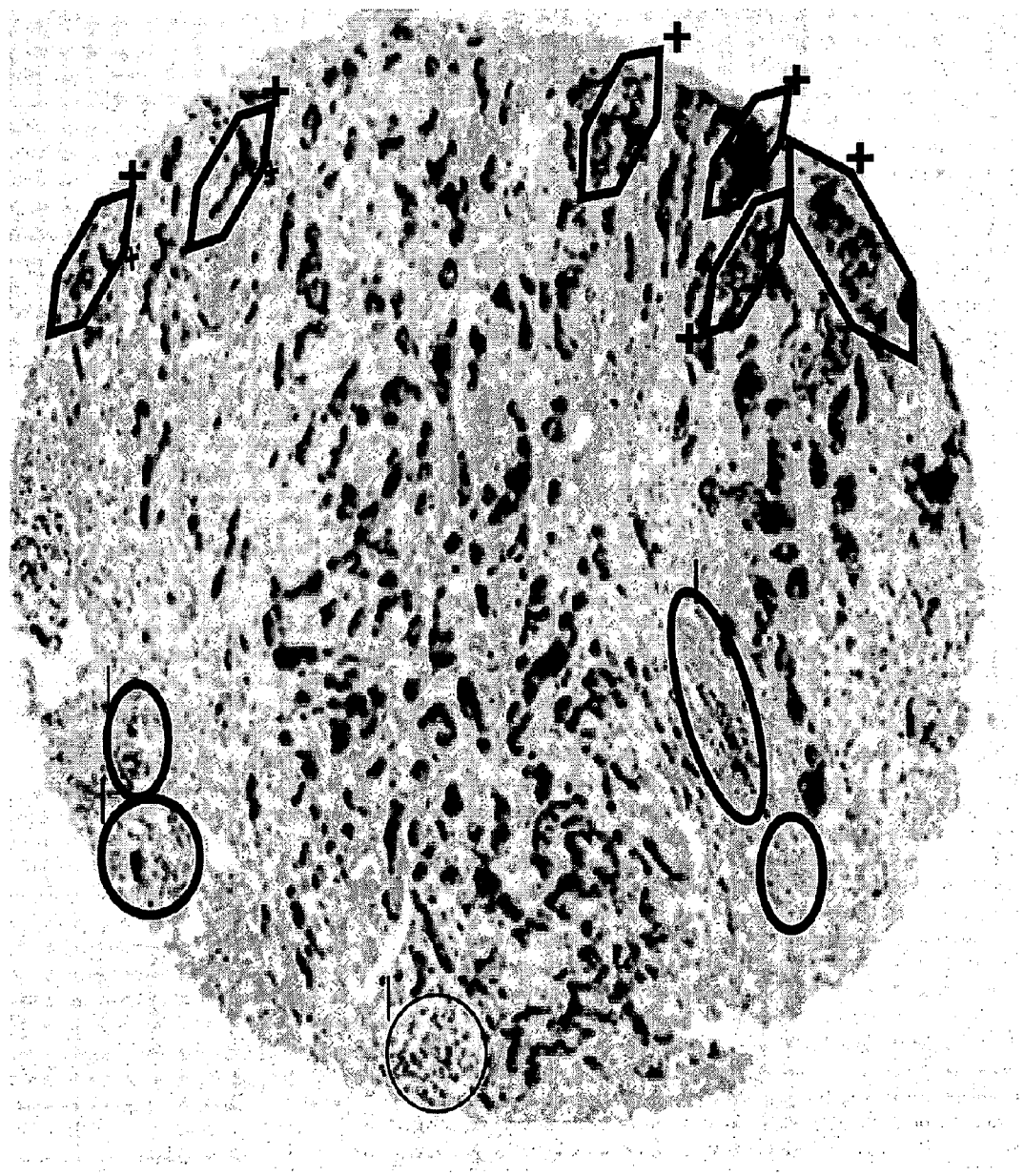
Figures 1, 10B:
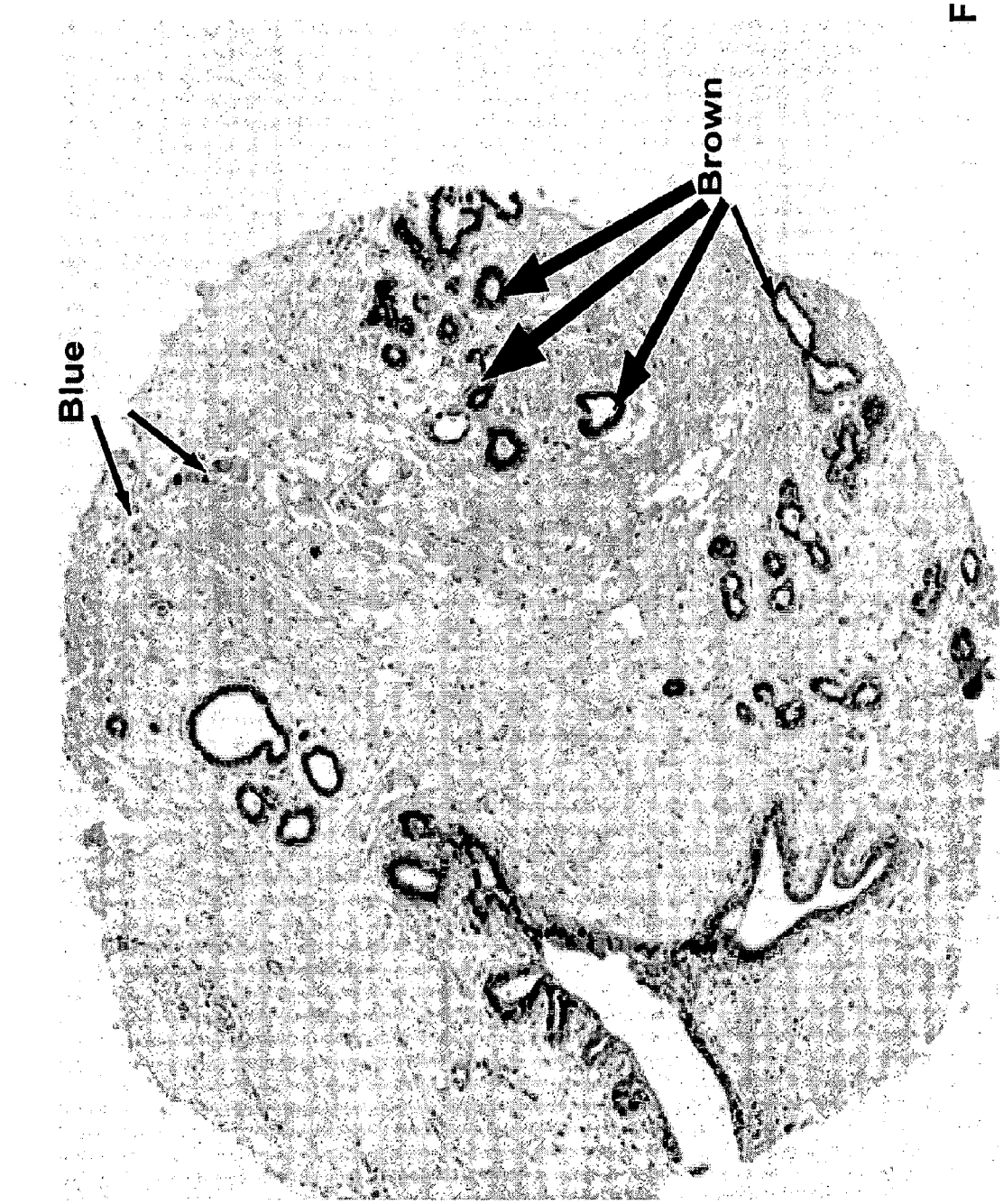
Figures 2, 10B:
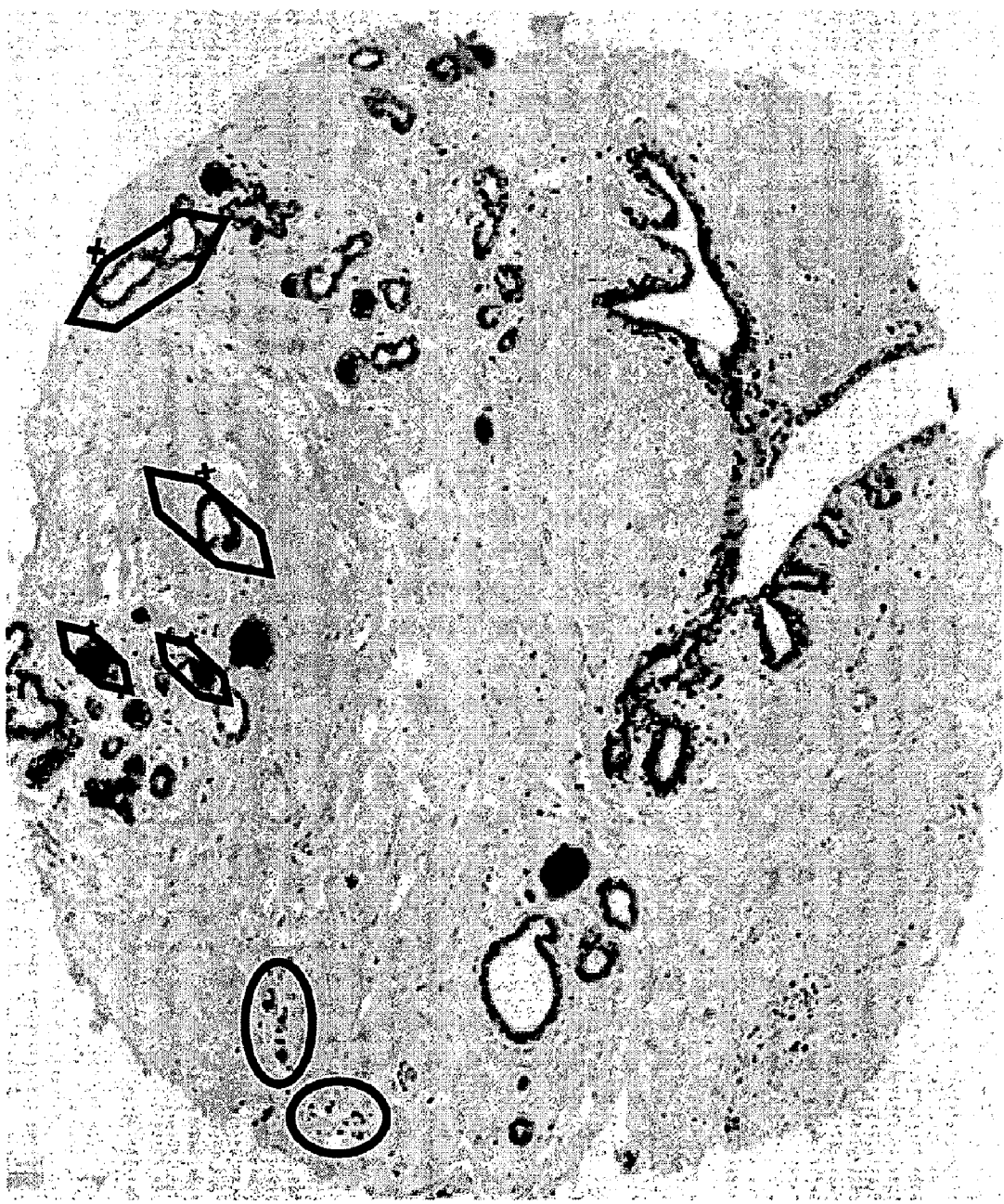

FIGS. 10A-1 and 10B-1 show images of two tissue cores stained to detect ER positive tumour nuclei. FIGS. 10A-2 and 10B-2 are the images shown in FIGS. 10A-1 and 10B-1 respectively after pattern recognition processing of DAB negative tumour nucleus (circled and labelled as blue) and DAB positive tumour nucleus (circled and labelled as brown).

1. Separating DAB from Haematoxylin.

FIG. 7A is a flow diagram showing how the image analysis method proceeds to separate DAB from haematoxylin. The main steps are:

1.1. Define the hue and colour for DAB positive status and haematoxylin staining. We select a random positive and negative core from the array to calibrate the following parameters. The colour RGB (RedGreenBlue) values for DAB and Haematoxylin. From the RGB values using an image processing system, for example, Matlab (Mathworks) we define the corresponding hue value for both DAB and Haematoxylin. This operation is done once to define the DAB hue (DAB_H) and RGB (DAB_RGB) and the corresponding Haematoxylin H_RGB and H_H thresholds for all the tissue core images.

1.2. Tissue core images are converted from RGB to HSV color space. DAB and Haematoxylin part are separated from the slide background and the connective tissue using the thresholds above, DAB_RGB, DAB_H and H_RGB, H_H. FIG. 6B shows the original stained image 0. The images resulting after the stain separation process are shown as images 1(a) and 1(b). Also shown is image 0(a) in FIG. 6B, which is the slide background following stain separation.

1.3. A binary (1 or 0) map is created for each single pixel to indicate whether is part (1) or not (0) of both DAB positive (DAB MASK) and Haematoxylin (H MASK).

2. Segmentation of all DAB Positive and DAB Negative Nuclear Patterns.

FIG. 7B shows schematically how the method proceeds to segment all nuclei present. Once DAB and haematoxylin are extracted, individual nuclei are demarked from the surrounding non-nuclear specific staining. The procedure is the same for segmenting DAB positive and DAB negative nuclei and the steps are set out as follows:

2.1. An appropriate mask is used to subtract from the original image the RGB values of either haematoxylin or DAB. There are numerous alternative colour representations (see, e.g. [1], [2]), which transform the RGB values linearly or non-linearly to different colour spaces. LAB and LUV are perceptually uniform colour spaces in which calculated distances between colours in colour space approximately reflect visually perceived colour differences. L is a lightness scale from 0 (black) to 100 (reference white), A and U are red-green scales and B and V are yellow-blue scales. DAB is extracted from the original image and converted from RGB to CIE LUV color space.

2.2. The L and U channels were added together and the result was transformed to grey level [black (0) to white (255)] color space. Preferably, image processing tools, such as, but not limited to the Image processing toolbox of Matlab (Mathworks®), is suitable for use in enhancing the contrast of the DAB pixels to the background.

2.3. Mean shift segmentation followed by image morphological operations are used to separate nuclear specific from surrounding non-specific DAB staining. This allows us also to better demark the nuclei to nuclei borders. The mean shift segmentation method is a powerful technique for image segmentation. The algorithm recursively moves the kernel smoothed centroid for every data point (see, e.g. [3],[4]). This separates the pixels in two clusters background (0) and nuclei (1) represented as a binary map.

Figure 8B:
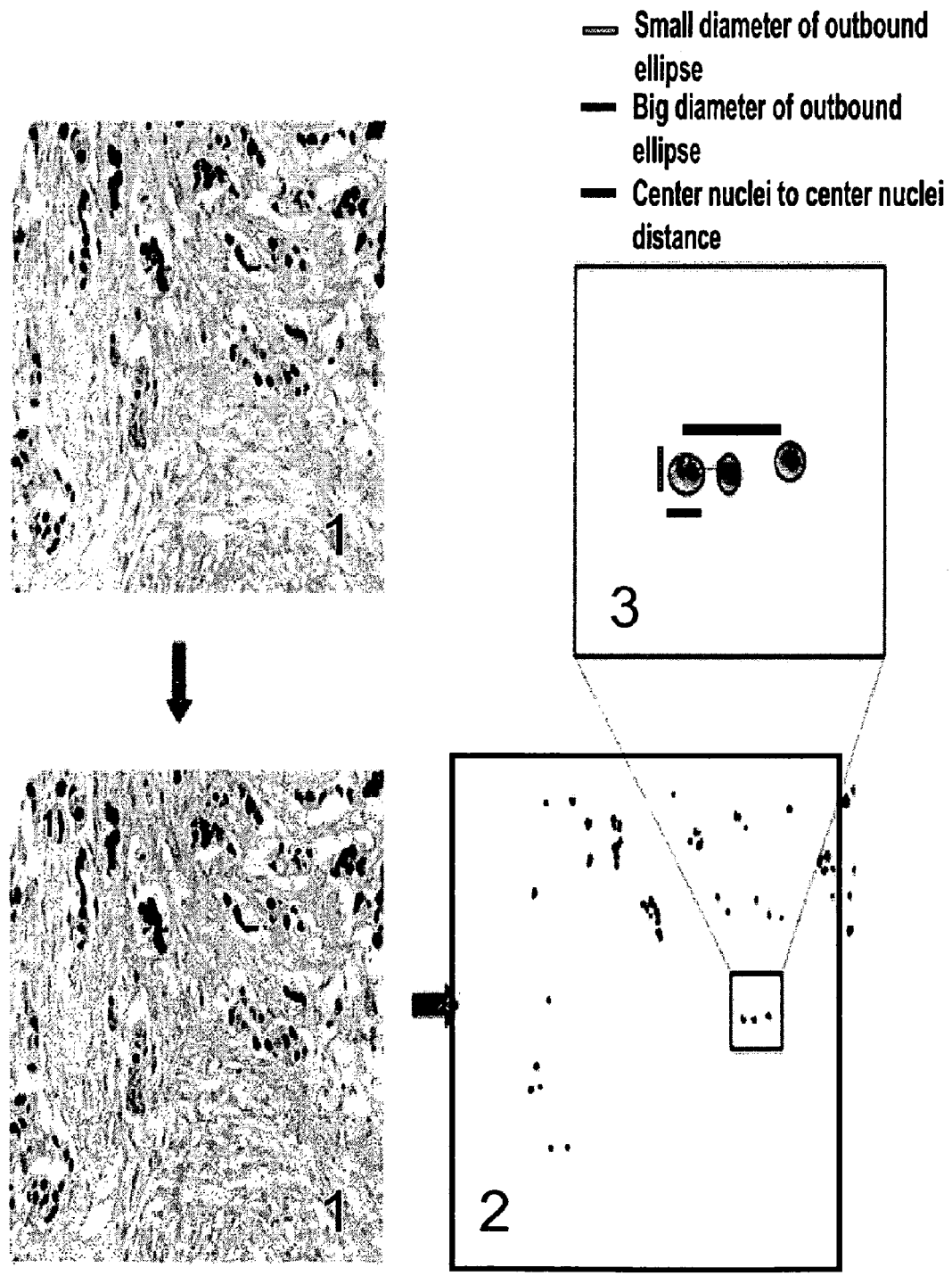
FIG. 8B shows 500×500 pixel digital images (labeled with reference numerals 1 to 3) of a section of tissue showing graphically, how the morphological analysis shown in FIG. 8A proceeds.

2.4. Using the binary map generated in 2.3 from the LUV representation only the pixels belonging to the nuclei are subtracted and converted to gray level colour space. The watershed segmentation is used to demark each single DAB positive nucleius. The images 1 in FIG. 8B show the result of the final demark of the DAB positive nuclei.

3. Learning of the Morphological and Spatial Descriptors of the DAB Positive Nuclear Patterns.

FIG. 8A is a flow diagram which details the steps used to describe mathematically the morphological features and/or morphological patterns of the one or more candidate objects following extraction of DAB positive nuclei.

The image processing toolbox is used to find the X, Y position of the nucleis' centres.

3.1 Each nucleus is being further described by its area, length of the minor and major axis of the smallest ellipse containing the nucleus and the distance to its neighbouring nuclei. The images 2 and 3 shown in FIG. 8B illustrate what each of these parameters means geometrically.

3.2 The next step is to mathematically represent the pattern of DAB positive nuclei. This is achieved by using the information extracted in step 3.1 to cluster the DAB positive nuclei in two clusters, cluster 1-nuclei close to each other and cluster 2 nuclei far from each other. The mean distance (DIST_THRESH) and the mean area (AREA_THRESH) of nuclei in cluster 1 are selected to describe mathematically the nuclear DAB positive pattern.

4. Segmentation of DAB Negative Nuclear Patterns.
Same as in step 3 above.

Figure 9A:
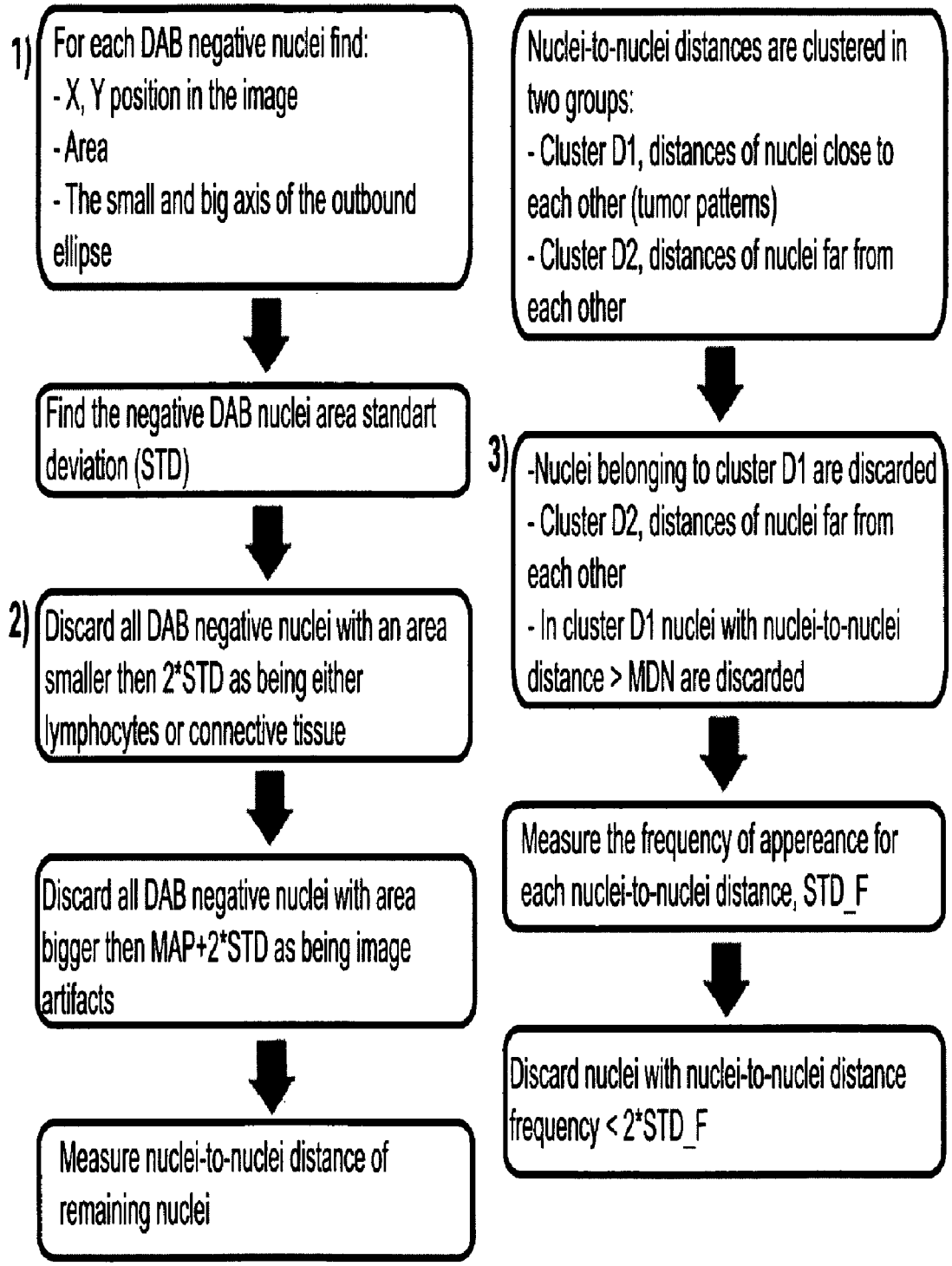
FIG. 9A is a flow diagram showing in further detail the fifth step, the extraction of DAB negative tumour nuclei, of the image analysis method shown in FIG. 6A
Figure 9B:
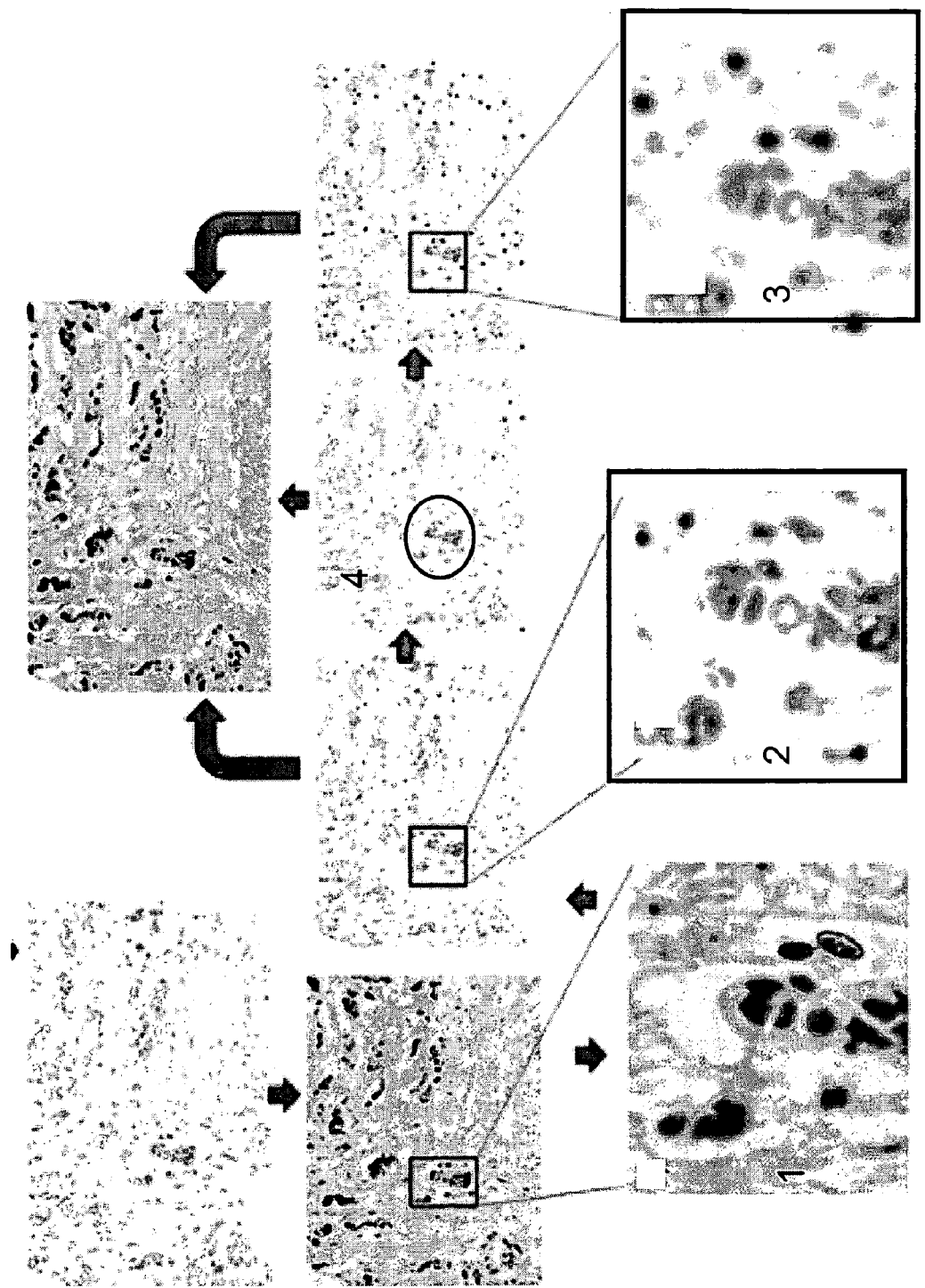
FIG. 9B shows 500×500 pixel digital images of a section of tissue, in which each image shows the output after performance of each stage of the fifth step detailed in FIG. 9A.

5. Selection of Tumour DAB Negative Nuclear Patterns.
Once the DAB negative nuclei are demarked then similar to the DAB positive nuclei we proceed first by describing them mathematically. The DAB negative nuclear pattern contains different types of nuclei and there is a decision to be make in terms of the approach adopted to find DAB negative nuclear patterns with the risk of being either too specific and missing some DAB negative tumour negative patterns or being less specific but counting non-relevant DAB negative nuclear patterns. The approach adopted proceeds by eliminating all non-relevant nuclei and leaving only DAB negative tumour nuclear patterns. FIG. 9A is a flow diagram detailing how the method proceeds to the elimination of non-relevant nuclear patterns. FIG. 9B shows the images (numbered 1 to 4) that are output after the main steps of the procedure detailed in FIG. 9A are performed.

5.1 For each DAB negative nucleus the following information is fetched, the X and Y position of the centre, its area, the length of the small and big diameter of the smallest ellipse containing the nucleus. This is illustrated in image 1 of FIG. 9B.

5.2 The standard deviation (AREA STD) of all nuclei area is computed. The standard deviation of all nuclei area (a random variable) is a measure of the spread of its values. If the data points are close to the mean, then the standard deviation is small. As well, if many data points are far from the mean, then the standard deviation is large. If all the data values are equal, then the standard deviation is zero. Using AREA_STD as a threshold all nuclei which area is smaller than AREA_STD are discarded as being too small. These can be part of a lymphocyte infiltration area, nuclei of connective tissue area or small image artifacts. Image 2 of FIG. 9B shows an example of some lymphocytes being detected.

5.3 The AREA_THRESH value found in step 3.2 from DAB positive nuclear patterns is used to discard the DAB negative big outliers which are artifacts due to either staining or glass slide digitalisation. A big outlier is all DAB negative entity which area is bigger than AREA_THRESH+2* AREA_STD.

5.4 The distance from each nucleus to its nearest neighbors is computed and all nuclei which shortest distance is bigger then DIST_THRESH are discarded. Image 3 of FIG. 9B shows an example of DAB negative nuclei that are discarded because they are far away from their neighbors.

5.5 Nuclei that pass the filtering step 5.4 but still are isolated, not part of a tumour gland are discarded as well. The nuclear neighbor connectivity (CONNNECT) is analysed. This is defined as the number of nuclei in the close neighborhood. A threshold of connectivity (CONNNECT_THRESH) is defined based on the deviation of nuclear overall connectivity as the 0.5 percentile of the connectivity distribution. All nuclei which CONNNECT is smaller then CONNNECT_THRESH are discarded. Image 4 of FIG. 9B shows an example of DAB negative nuclei, highlighted in blue and shown demarked, that are discarded because they are isolated.

Step 6: Final Assessment of Biomarker Expression.

REFERENCES FOR EXAMPLE 1

1. Sangwine, S. a. H., *The Colour Image Processing Handbook*. REN ed, ed. C.a. Hall. 1998, London.
2. Gonzalez, R., "*Digital Image Processing*. Reading, ed. Addison-Wesley. 1992, MA.
3. D. Comanicu, P. M., *Mean shift: A robust approach toward feature space analysis*. IEEE Trans. Pattern Anal. Machine Intell, 2002. 24: p. 603-619.
4. C. Yang, R. D., D. DeMenthon and L. Davis., *Mean-Shift Analysis Using Quasi-Newton Methods*. IEEE International Conference on Image Processing, 2003. 3: p. 447-450.

Example 2

Patients and Tumour Samples

Three different cohorts of patients were used during this study. The cohorts are described in Table 1. The studies were approved by the ethical committees at Lund and Linkoping and timed Universities. Cohort 1 consisted of a cohort of 564 pre-menopausal women with primary breast cancer in the South and Southeast regions of Sweden who enrolled in a multi-centre clinical trial between 1984 and 1991[23]. Patients were randomly assigned to either two years of adjuvant tamoxifen (n=276) or a control group (n=288) and has been described in detail previously. The aim of this study was to examine the effect of tamoxifen on recurrence-free survival (RFS) and the study has been described in detail elsewhere [24].

Cohort II consisted of 512 consecutive breast cancer cases diagnosed at the Department of Pathology, Malmo University Hospital, Malmo, Sweden, between 1988 and 1992 and has been described previously {O'Brien et al., 2007 infra} The median age was 65 years (range 27-96) and median follow up time regarding disease specific and overall survival was 11 years (range 0-17). Patients with recurrent disease and previous systemic therapies were excluded, as well as a number of mis-classified DCIS cases.

Cohort III consisted of 179 consecutive cases of invasive breast cancer diagnosed at the Department of Pathology, Malmo University Hospital, Malmo, Sweden. The median age at diagnosis was 65 (range 35-97) and the median follow-up for Overall Survival (OS).

General Methodology
Tissue Microarrays and Immunohistochemistry

Areas representative of invasive cancer were marked on haematoxylin and eosin-stained slides and TMAs were constructed using an automated tissue arrayer (ATA-27, Beecher Inc, WI) (Cohort I) or a manual arrayer (MTA-1, Beecher Inc) (Cohorts II and III). Two 0.6 mm cores (1.0 mm cores for cohort III) were extracted from each donor block and assembled in a recipient block. Recipient blocks were limited to approximately 200 cores each. In general, cores were taken from the peripheral part of the tumour in cases where the tumour had well-defined borders. In more diffusely growing tumours, areas with the highest tumour cell density were primarily targeted. Necrotic tissue was avoided. For immunohistochemistical analysis, sections (4 µm) were dried, deparaffinized, rehydrated and through descending concentrations of ethanol. Heat-mediated antigen retrieval was performed using microwave treatment for 2×5 min in a citrate buffer before being processed in the Ventana Benchmark system (Ventana Medical Systems Inc, AZ) using pre-diluted antibodies to ER (Anti-ER, clone 6F11), PR (Anti-PgR, clone 16).

Image Acquisition and Management

The Aperio ScanScope CS Slide Scanner (Aperio Technologies, Vista, Calif.) system was used to capture digital images. Images were captured at 20× objective and stored as multilayered tagged image format files (TIFF). Digital slides were viewed using ImageScope (Aperio). Single core images were extracted for analysis using TMALab (Aperio).

Image Analysis Development and Statistical Analysis

The image analysis method was developed using MatLab 7 (MathWorks, Apple Hill Drive, Mass.) and the Image processing toolbox. Statistical analysis was carried out using MatLab 7 (MathWorks) and SPSS version 11.0 (SPSS Inc, Chicago, Ill.). Spearman's Rho correlation was used to estimate the relationship between automated and manual analysis. Mann Whitney U test was used to evaluate differences between mean intensity values and grade. The $\chi^2$ test and Fishers exact test were used to evaluate differences in distribution of clinical data and tumour characteristics between samples using various different markers. Kaplan-Meier analysis and the log rank test were used to illustrate differences between recurrence free survival (RFS), overall survival (OS) and breast cancer-specific survival (BCSS) according to the expression of different markers. P value <0.05 was considered statistically significant.

Image Analysis

This study was based on the development of an image analysis method and a system to implement the method in order to quantify nuclear ER and PR in breast cancer. FIG. 6A is a flow diagram showing the steps of the method. The method is composed of a series of steps where the output of one is the input of the next. All of the steps are linked together in a cascade fashion, an overview for which is set out in Example 1 and illustrated in FIGS. 6-10.

What follows is a brief description of the image analysis method. The initial step of the entire process is the separation of stained tissue from unstained background. The DAB and haematoxylin fractions are further analysed independently to identify all nuclei and eliminate non-specific staining. A non-supervised learning approach is then applied to DAB positive nuclei to assimilate the morphological features of the positive nuclei present. The morphological features assimilated from the DAB positive nuclei are applied to DAB negative nuclei in order to eliminate non-tumour nuclei (such as, for example, lymphocytic infiltration).

Finally, the percentage of DAB tumour positive nuclei and the mean intensity of DAB positive nuclei is calculated and stored as the final output for the core. In this example, the degree of staining (ie the intensity of the staining) was not included in the final quantitation step.

Results 2

The three cohorts comprised of 1255 patients in total. ER expression data were available for 1139 patients (91%), and PR expression data were available for 1009 patients (81%). A number of cores were not suitable for image analysis due to large image artifacts and thus automated analysis was restricted to 1064 patients (85%) for whom ER data were available and 951 (76%) for whom PR data were available. Table 2 outlines the breakdown of patients available for image analysis according to the three individual cohorts.

Results 2(A)
Quantitative Assessment of ER and PR Status by Image Analysis—Correlation of Manual and Automated Approaches Quantitative nuclear ER and PR expression levels were quantified using the automated image analysis method as described above. The accuracy of the image analysis method and the system for implementing the method was initially confirmed by a histopathologist (PH), who validated the output in 18 representative images (500×500 pixels). The image analysis method was run on the 18 sample images and compared the manual count of a pathologist. There was an excellent correlation between percentage positive tumour nuclei as determined by the image analysis method when compared to a manual analysis carried out by a pathologist (Spearman's Rho=0.9, p<0.001 (FIG. 2A), thus confirming (i) the ability of the image analysis method to identify and differentiate tumour from stroma and (ii) also confirming the accuracy of the image analysis in quantifying ER and PR expression.

Figure 2A:
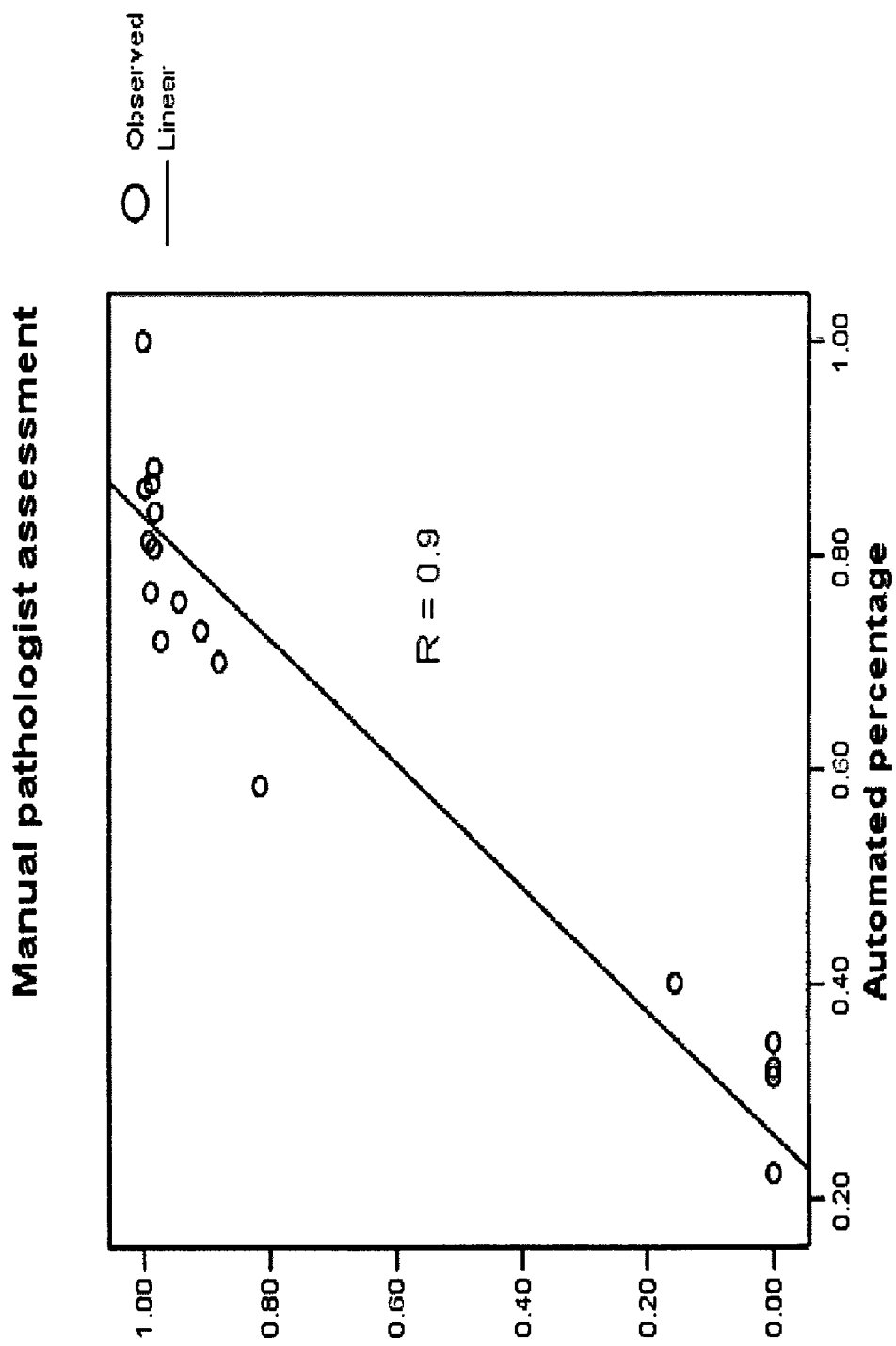
FIGS. 2A to 2E are graphs showing the correlation between manual and automated scoring.
Figure 2B:
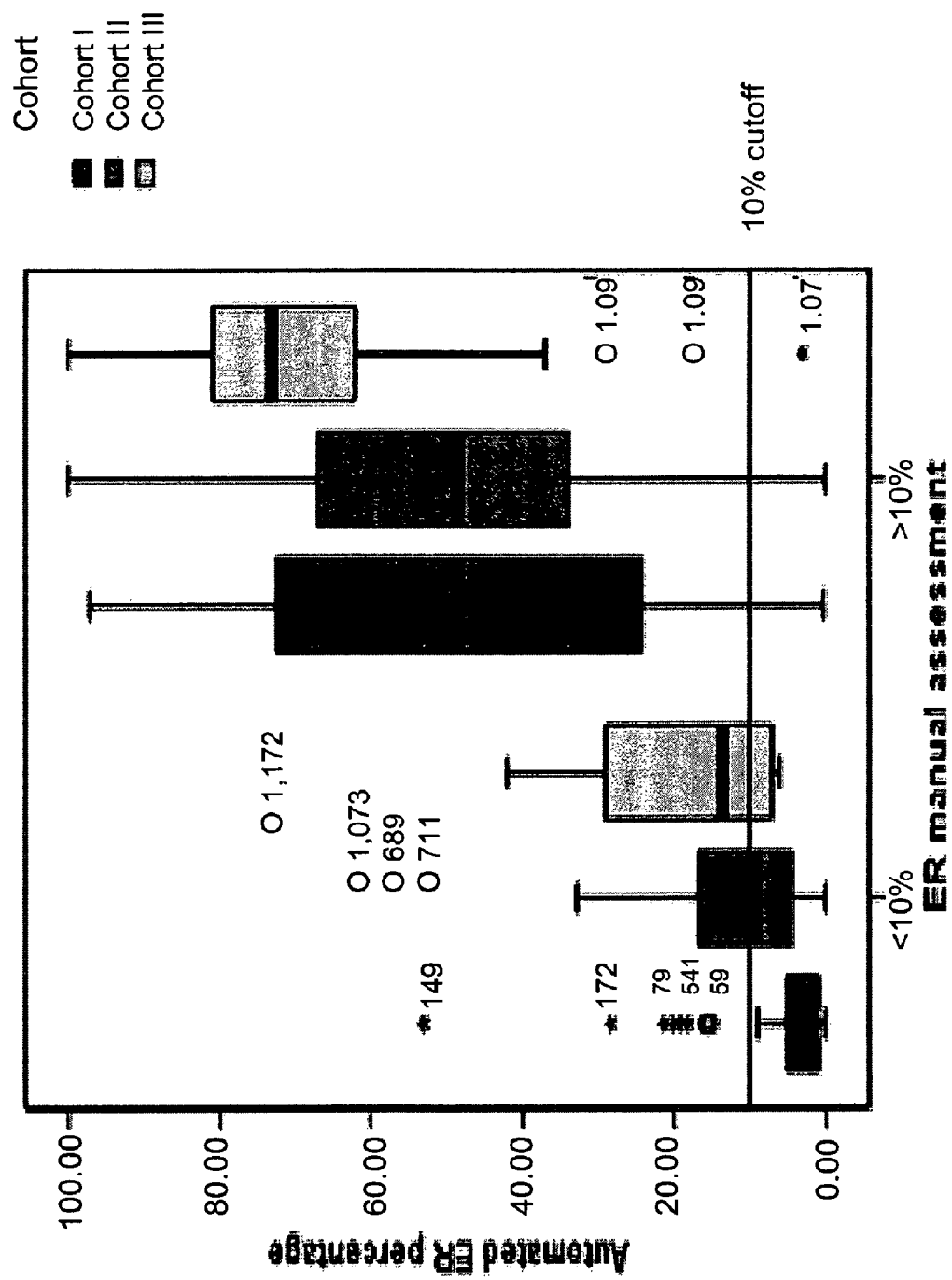
Figure 2C:
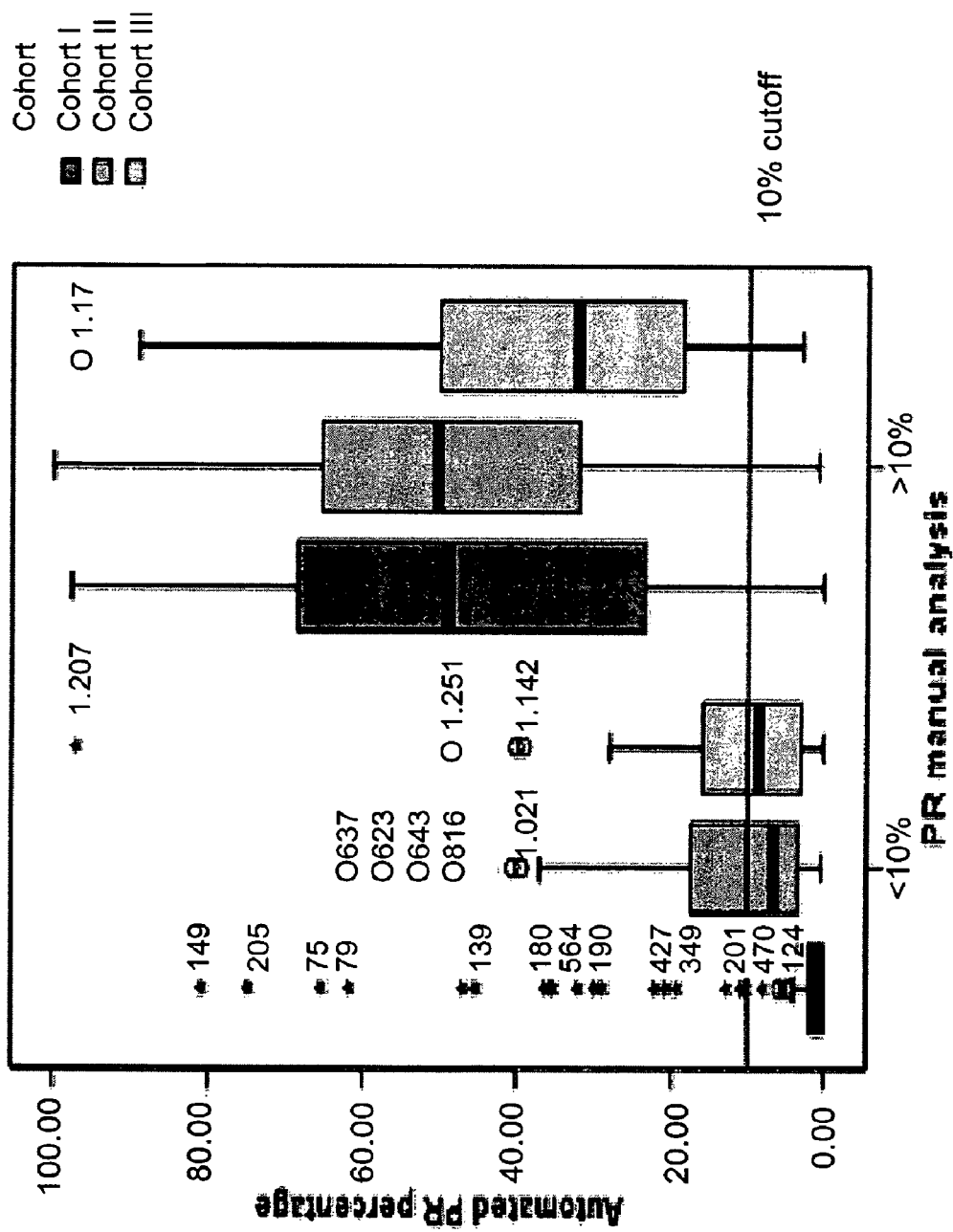
Figure 2D:
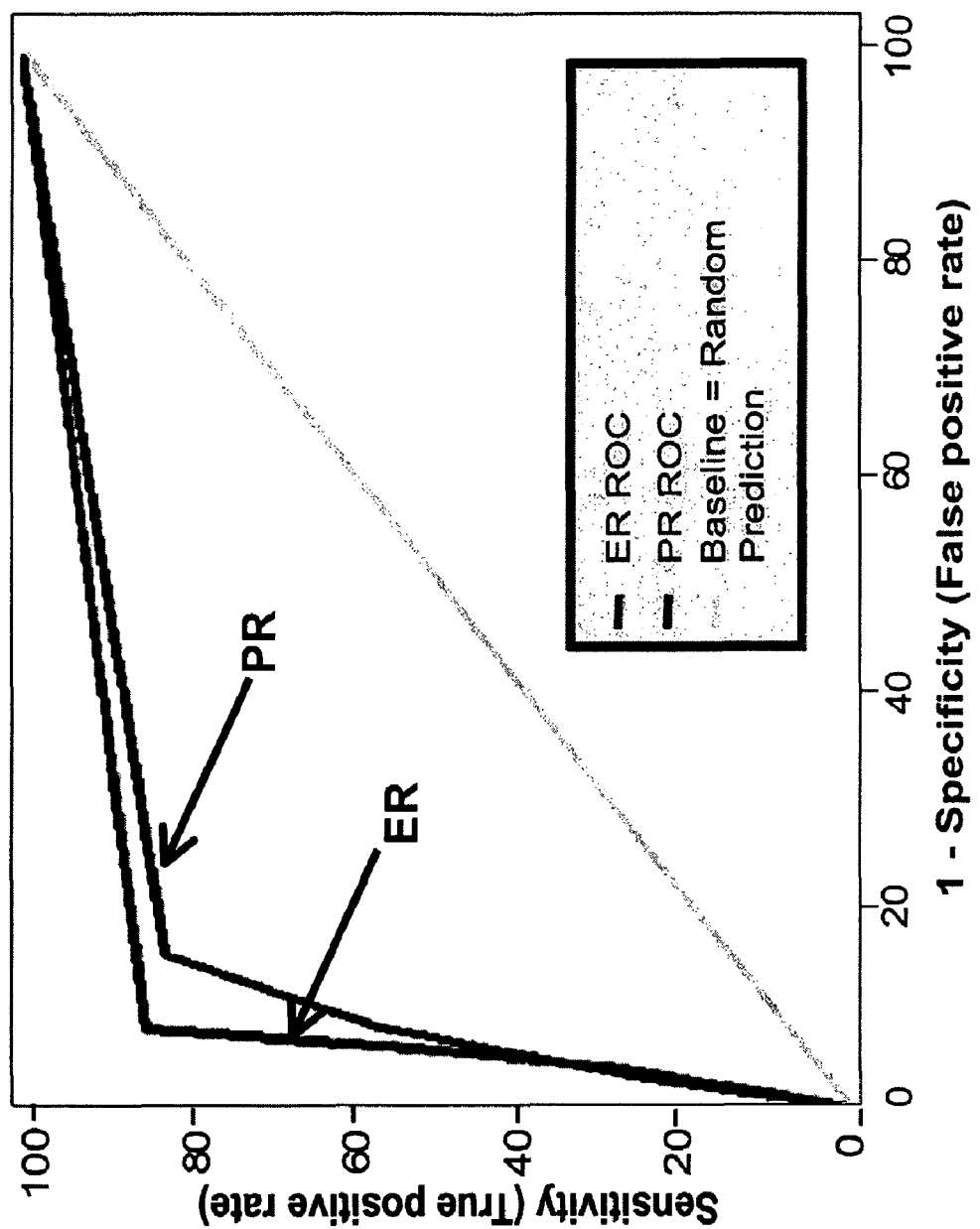
Figure 2E:
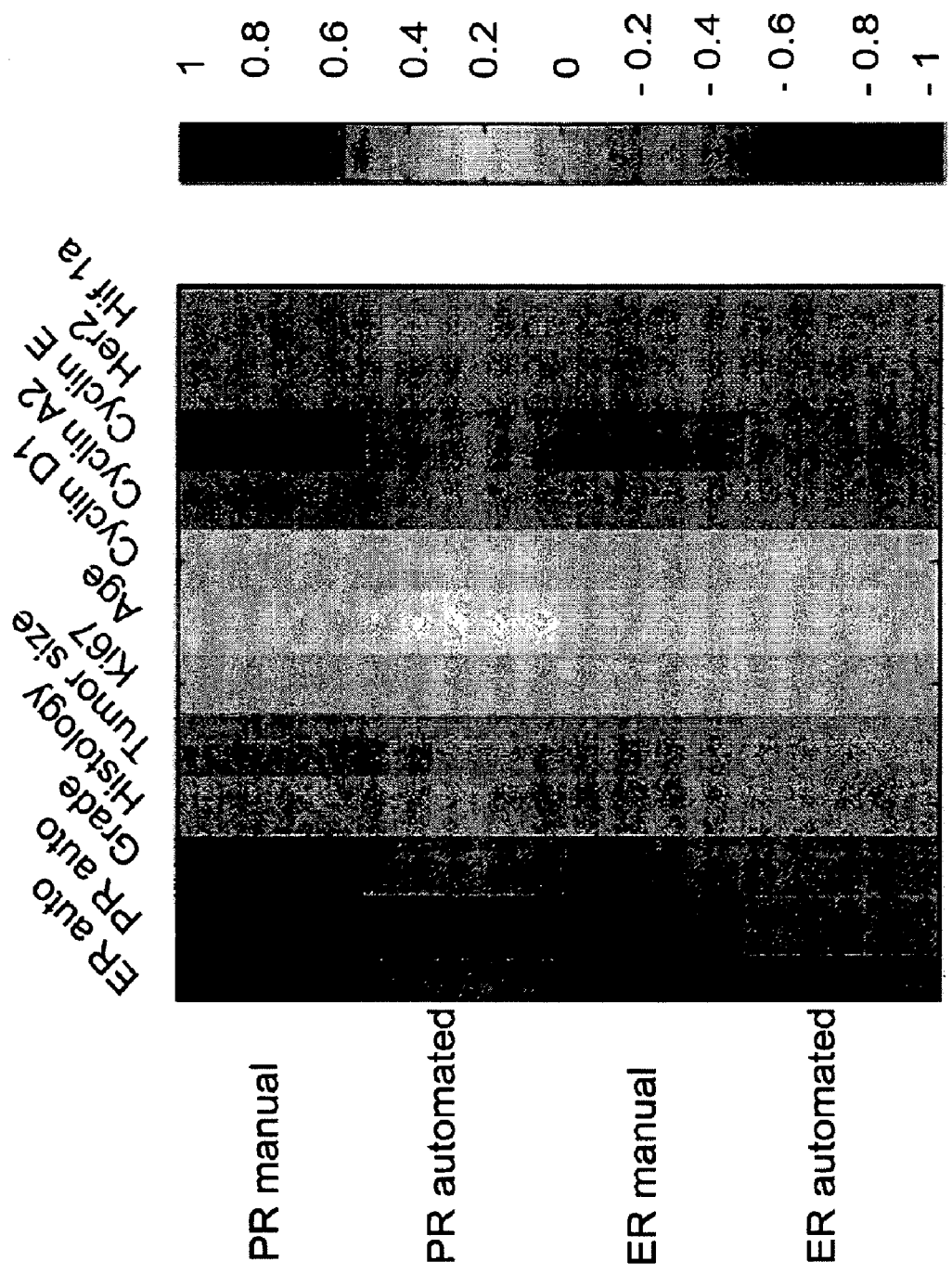

Following this initial validation, ER and PR expression levels as determined by image analysis were compared with the manual assessment as defined by the pathologist in the three cohorts outlined above. FIG. 2A shows the correlation of the automated scores with the scores of a trained pathologist on the same cores. FIG. 2B shows the ER automated scores distribution within the ER negative and ER positive patient group. FIG. 2C illustrates the PR automated scores distribution within the PR negative and PR positive patient group. FIG. 2D show receiver-operator curves (ROCs) for the estrogen receptor (ER) and the progesterone receptor (PR), with the number of false positives plotted along the abscissa and the number of true positives plotted along the ordinate. It will be understood that with such a graphing technique that a curve more to the upper-left corner implies better performance. FIG. 2E is a heat map showing the correlation between ER and PR expression determined by both automated and manual analysis and a number of clinicopathological parameters. FIG. 2A thus illustrates the distribution of ER and PR expression levels as determined by image analysis performed manually by a pathologist. A distinct separation between the negative and positive groups in cohort I, II and III is shown in FIGS. 2B and 2C. By employing cut off of 15% for ER from 1064, 99 (9%) and for PR from 951,155 (16%) number of cores were misclassified.

In an effort to further validate the image analysis method, we compared the prognostic ability of ER and PR expression as determined by image analysis to that as determined by pathological assessment. A cutoff of 10% was used to dichotomize the automated score in cohort I, II and III into ER−/+ and PR−/+. Once again an excellent correlation was seen between dichotomized ER and PR as determined by image analysis and manual assessment (0-10% v 11-100%) Spearman's rho was 0.7 for ER (p-value<0.01) and 0.6 for PR (p-value<0.01).

Cox univariate regression analysis was then carried out to compare hazard ratios of OS based on the manual method versus the automated image analysis method. Once again, a continuous automated assessment of ER and PR expression was dichotomized using a threshold of 10%. A Cox regression univariate analysis was carried on each cohort to assess the difference in Hazard Ration (HR) between ER−, PR− (<10%) and ER+, PR+ (>10%) using both a manual pathologist based assessment and a automated image analysis method assessment. Table 3 summarises our findings in terms of univariate analysis of OS based on manual and automated analysis. It is clear that there was no significant difference in the HRs calculated using either the manual method or the automated image analysis method.

Results 2(B)
ER and PR Core Heterogeneity

Figure 3A:
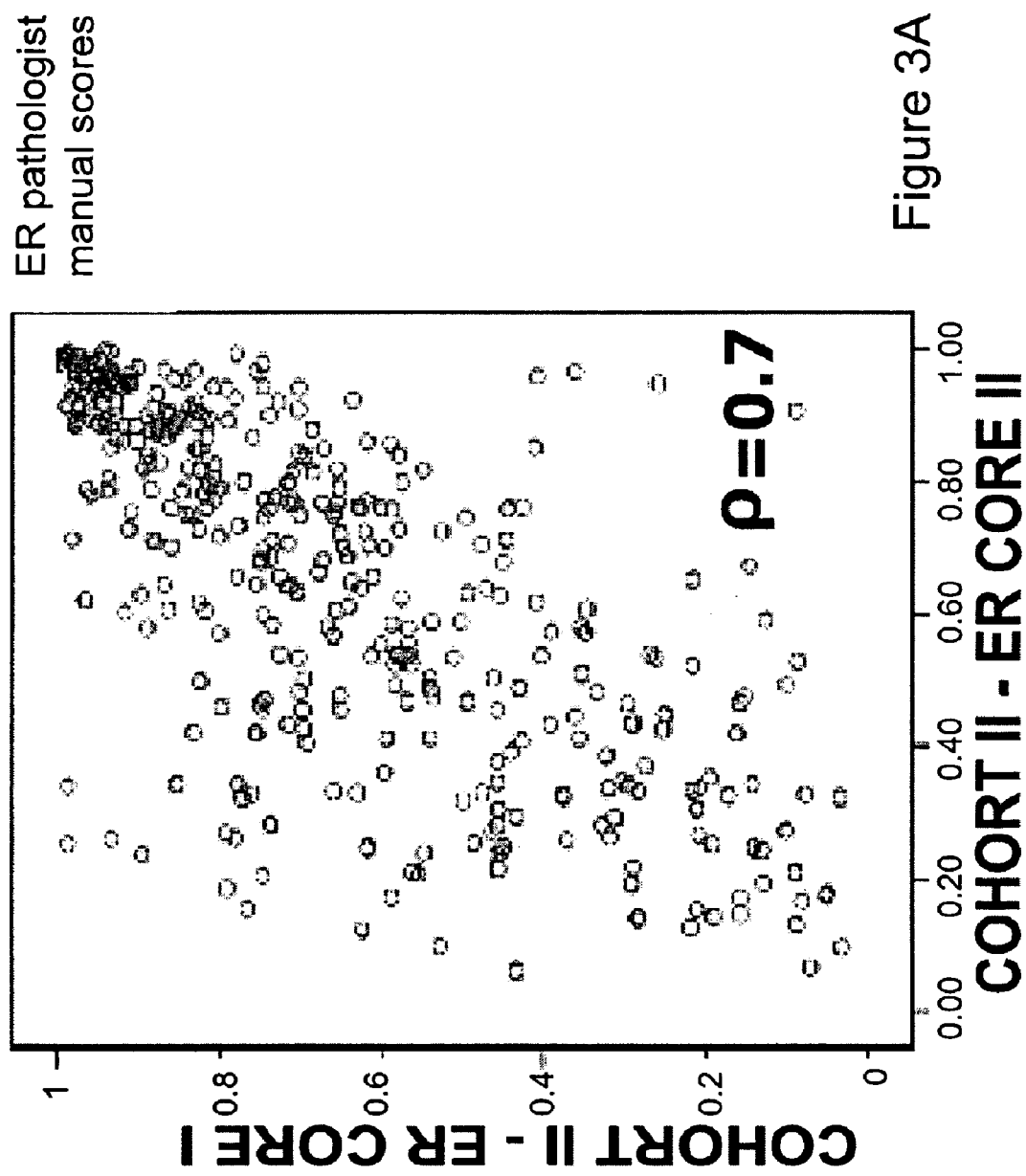
Figure 3B:
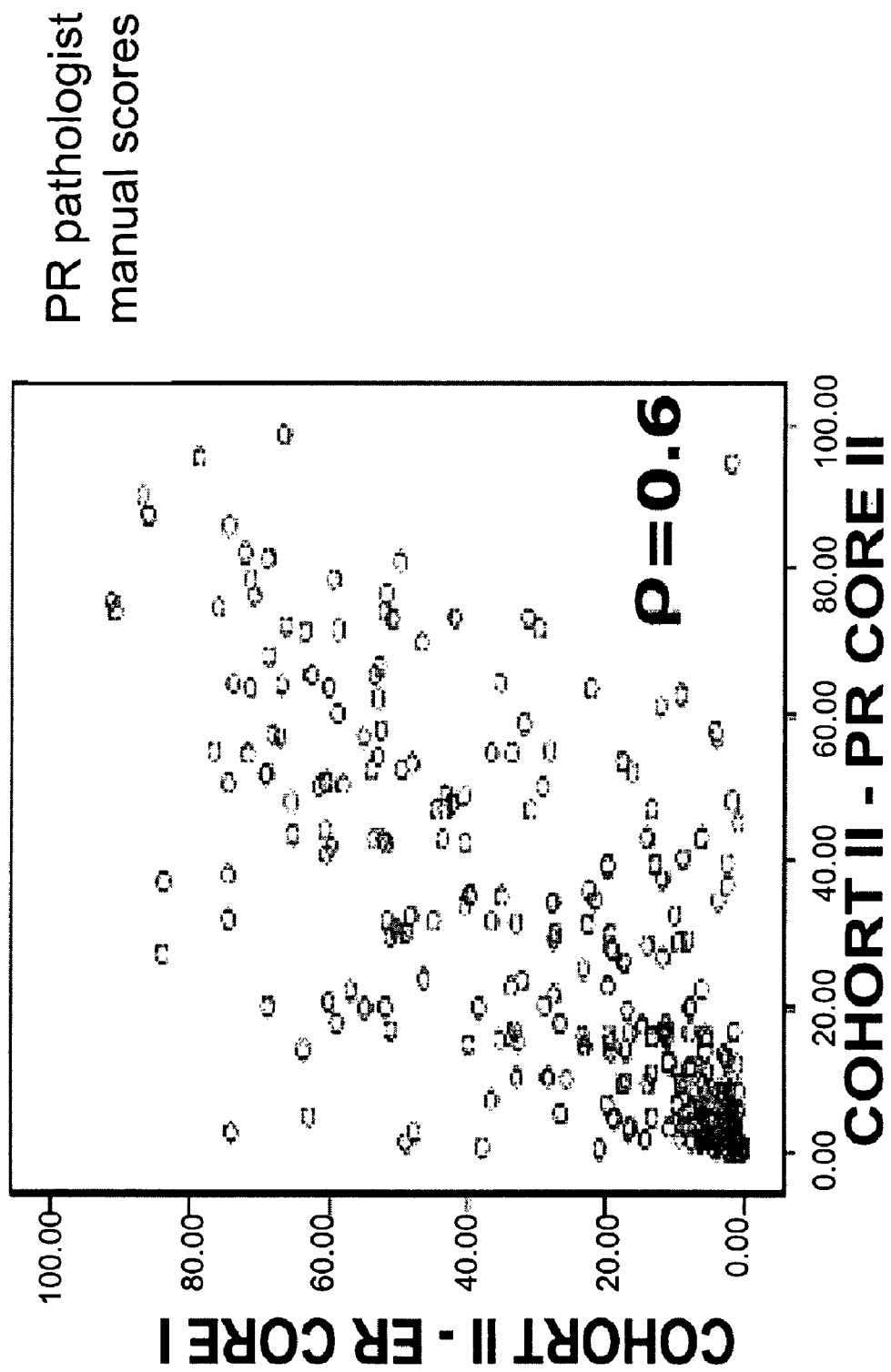
Figure 3C:
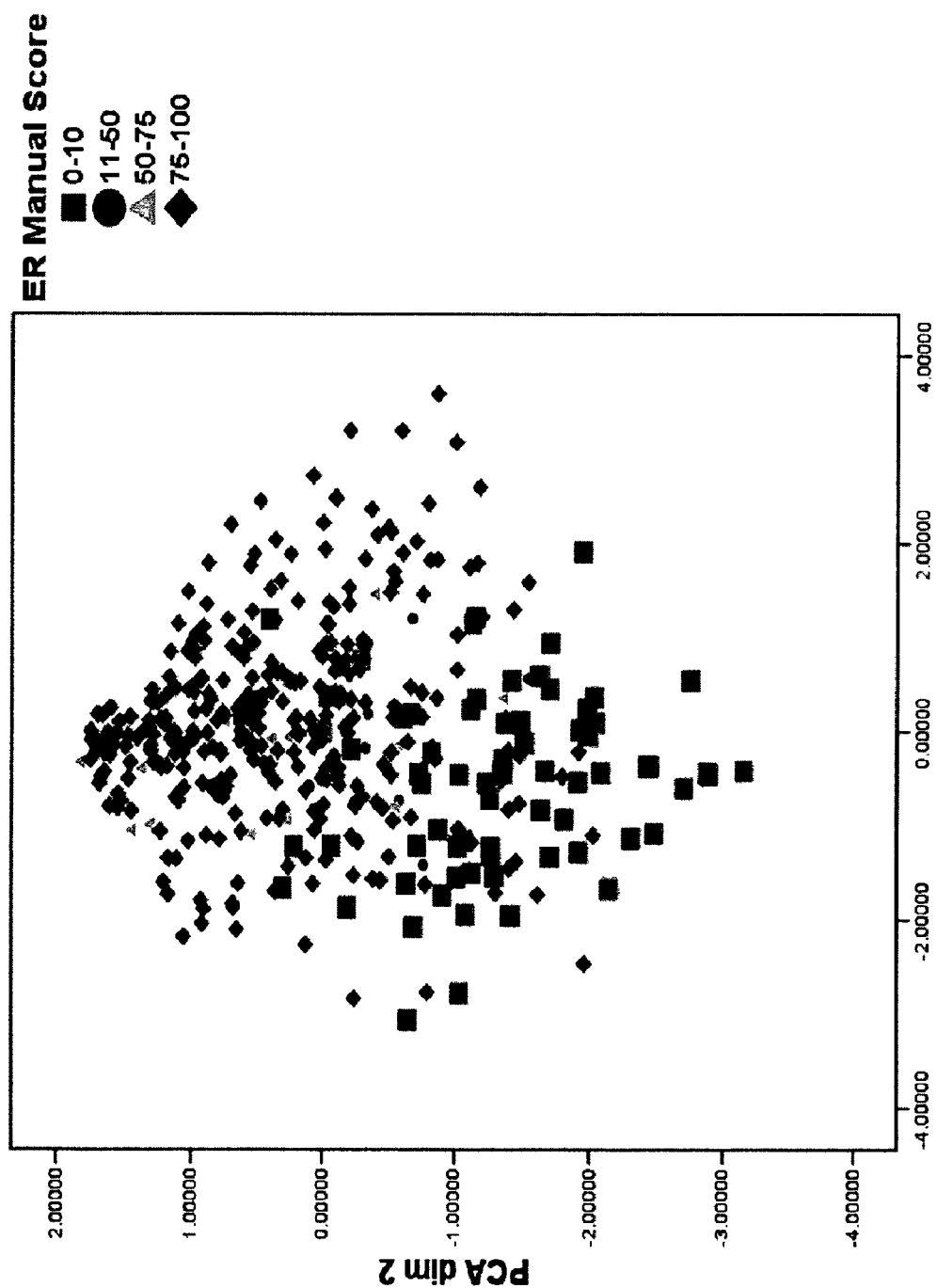
Figure 3D:
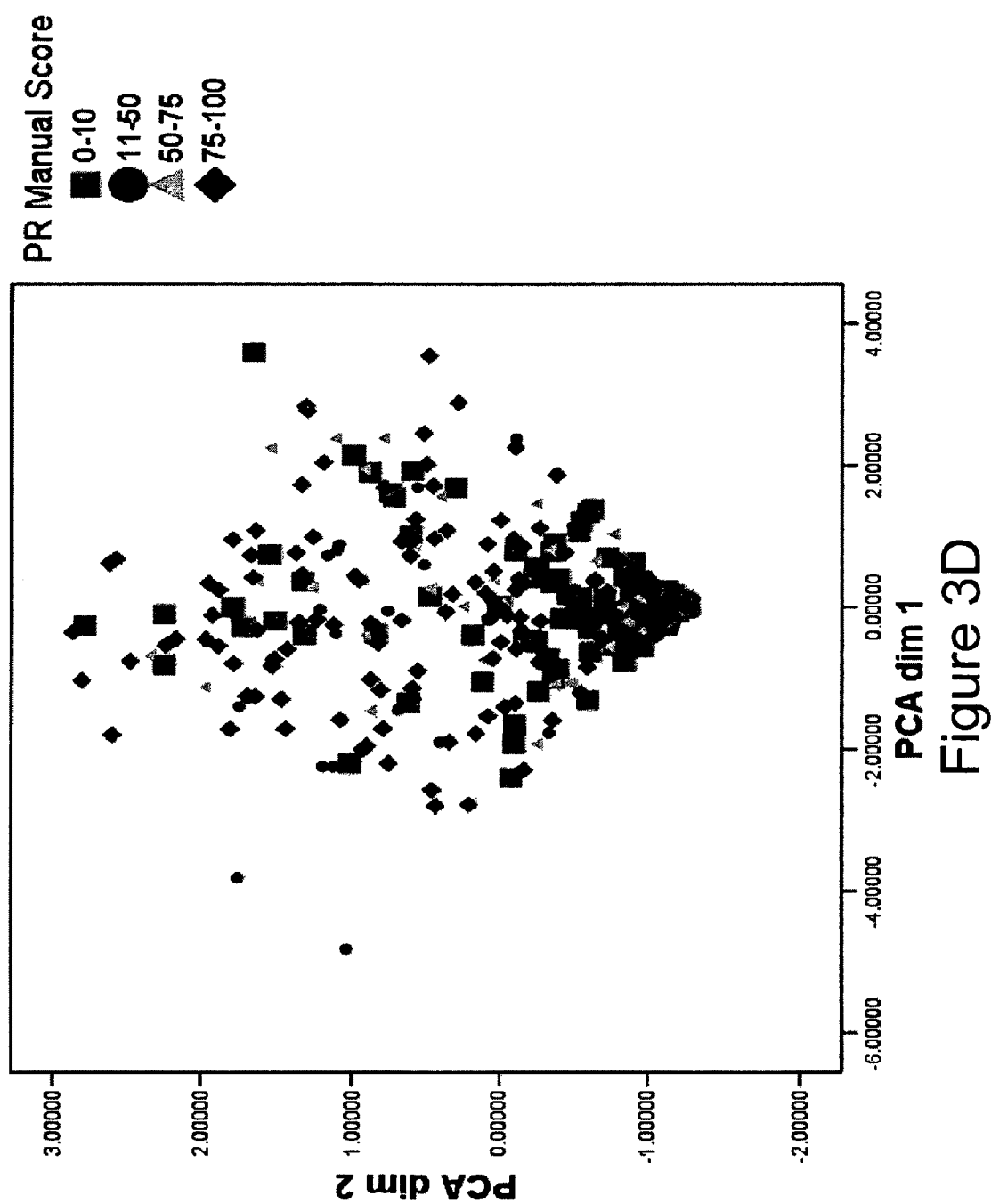
Figure 3E:
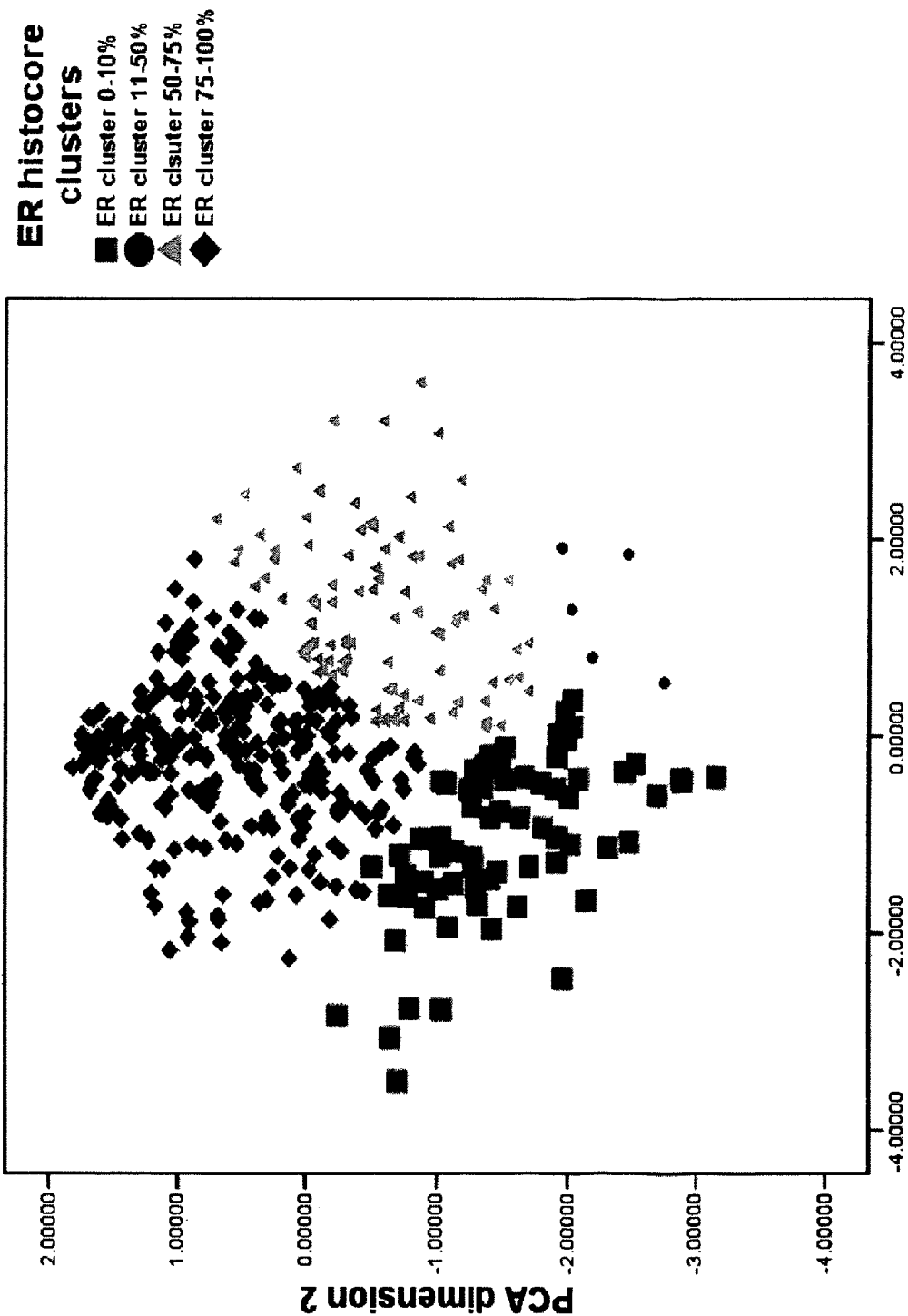
Figure 3F:
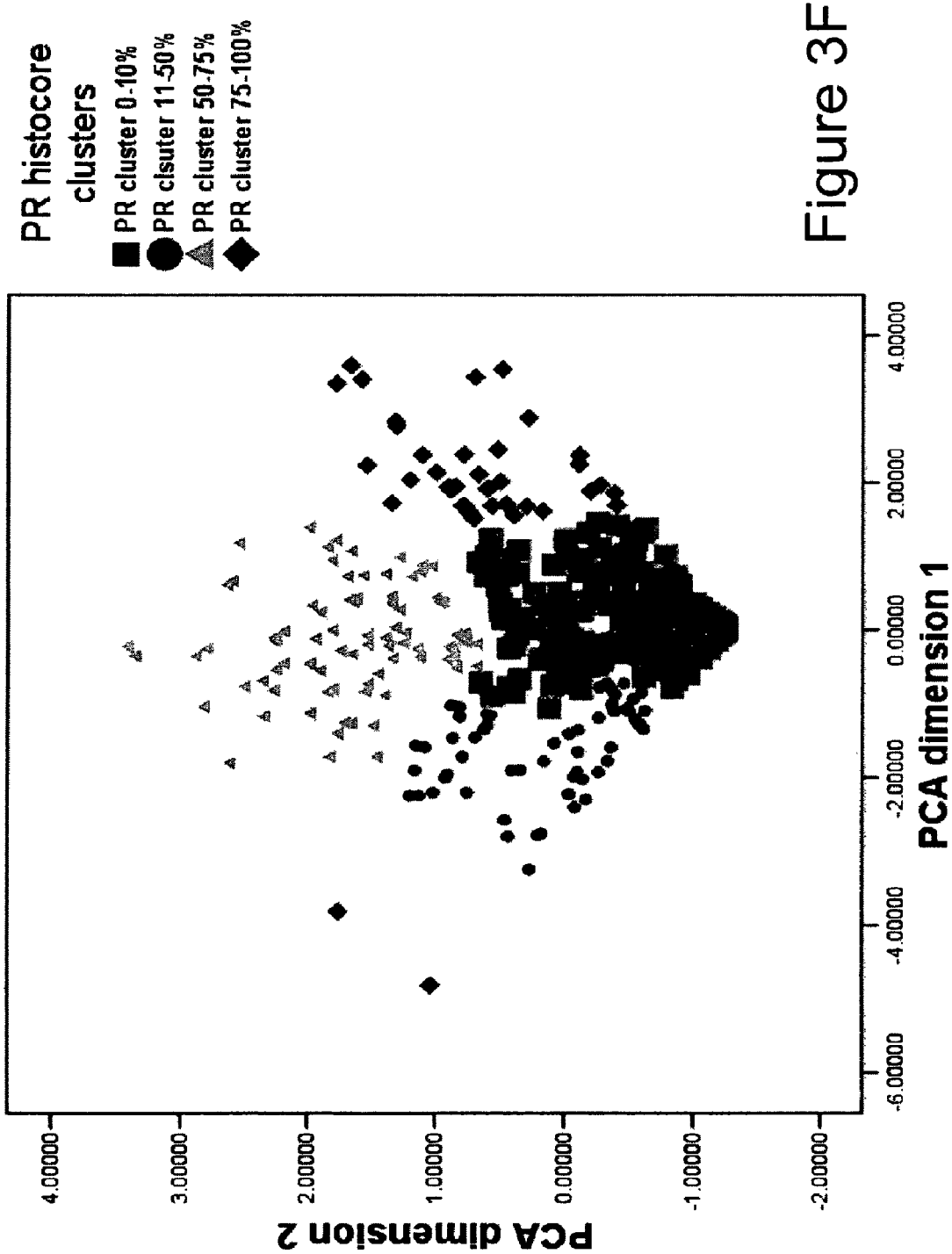
Figure 3H:
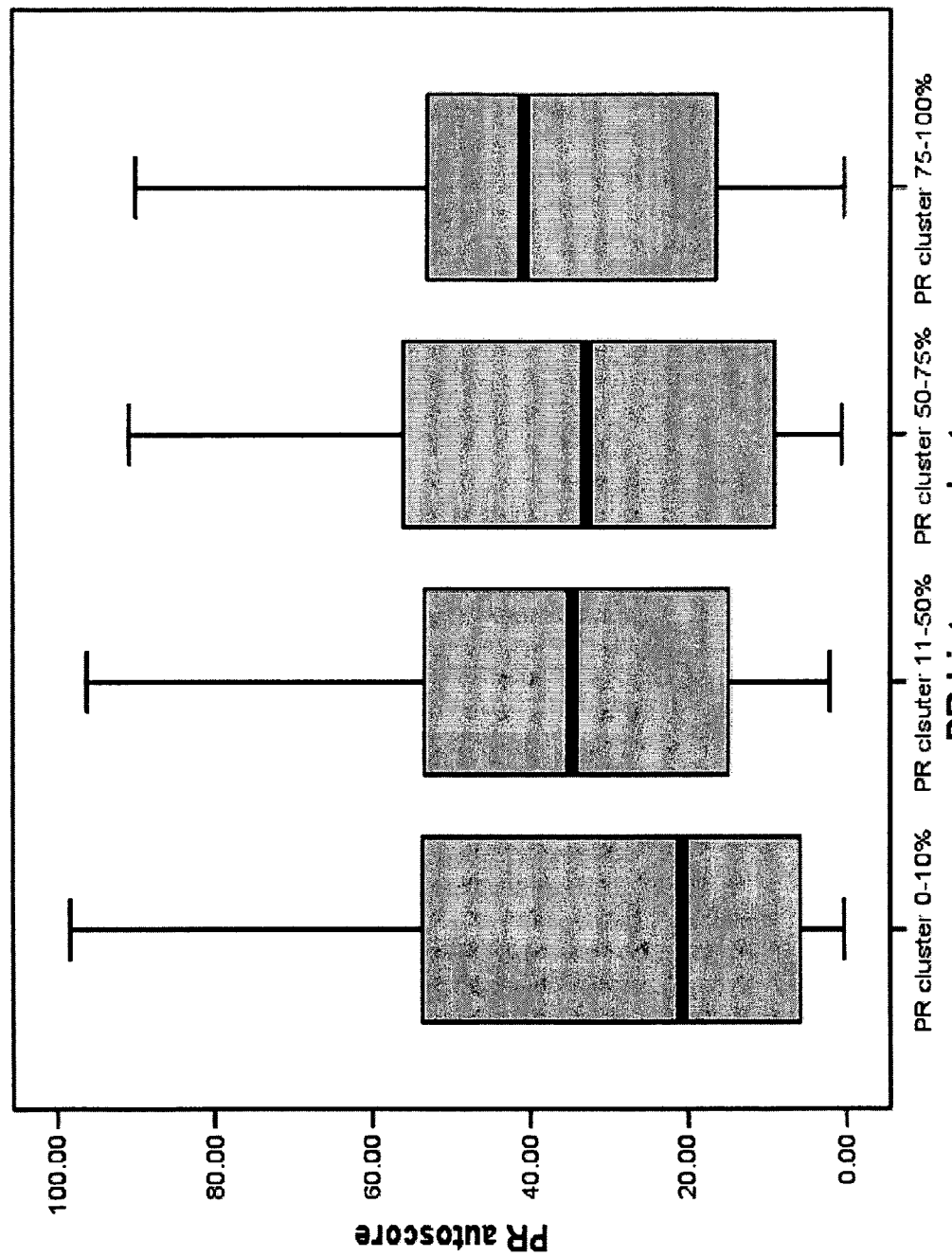

FIGS. 3A and 3B show the correlation of cores one and two using PCA (Principle Component Analysis). FIGS. 3C and 3D show the distribution of the manual scores of ER and PR on the PCA components. FIGS. 3E and 3F show the ER and PR clusters on the PCA components. FIGS. 3G and 3H show the ER and PR automated score distribution within each cluster.

TMAs are often criticized as they often don't address tumour heterogeneity, automated analysis allows for an in-depth evaluation of tumour heterogeneity between individual cores. To assess the level of intra-tumour heterogeneity of ER and PR as defined by image analysis, data were initially analysed using simple scatter plots. Initial evaluation revealed a strong correlation for duplicate cores for both ER (Spearman's Rho=0.7, p<0.01) and PR (Spearman's Rho=0.6, p<0.01). However inspection of the scatter plots does reveal a broader dispersion of PR data as compare to ER data (shown in FIGS. 3A and 3B). Although FIGS. 3A and 3B illustrate ER and PR data from cohort II, a similar pattern was evident in the other cohorts (data not shown)

To investigate this in more detail, Principal Component Analysis (PCA) was used to detect any structure in the relationship between duplicate ER and PR cores (shown in FIGS. 3C and 3D). Using PCA, ER and PR were independently compressed to the two most discriminative dimensions. The two most discriminative functions were then clustered using a two step clustering procedure to identify the four most predominant clusters within these data (shown in FIGS. 3E and 3F). The distribution of ER and PR expression within these clusters was then plotted in a box plot. FIG. 3E illustrates that there was an incremental rise in the mean ER expression as determined by the image analysis method. This would suggest that duplicate cores from the same tumour displayed similar levels of ER expression as determined by the image analysis method, thus indicating the homogenous nature of ER staining. There were 66 tumours in cluster I, 5 in cluster II, 89 in cluster III and 289 in cluster IV for ER. A similar pattern was not evident in the PR clusters, thus indicating a more heterogenous pattern of staining for PR. Similar results were observed in cohort I and III (data not shown).

Results 2(C)
Automatic Determination of the Optimal Cutoff for Survival Analysis based on ER/PR Expression As mentioned previously 10% positive tumour cells based on manual analysis is currently considered to be the optimal threshold for determining ER/PR positively. We therefore proceeded to use random forest clustering (RFC) in an attempt to identify new prognostic subgroups following quantitative assessment of ER and PR via image analysis. Random forest clustering is an unsupervised strategy that has been used to profile tumours based on TMA data [26, 27] and our group has previously used RFC to identify new prognostic subgroups based on automated analysis of IHC data (Brennan et al). Given the fact that Cohort 1 could be used to analyse both prognostic (in the untreated arm) and predictive variables (in the treated arm), our analysis was restricted to this cohort.

Figure 4A:
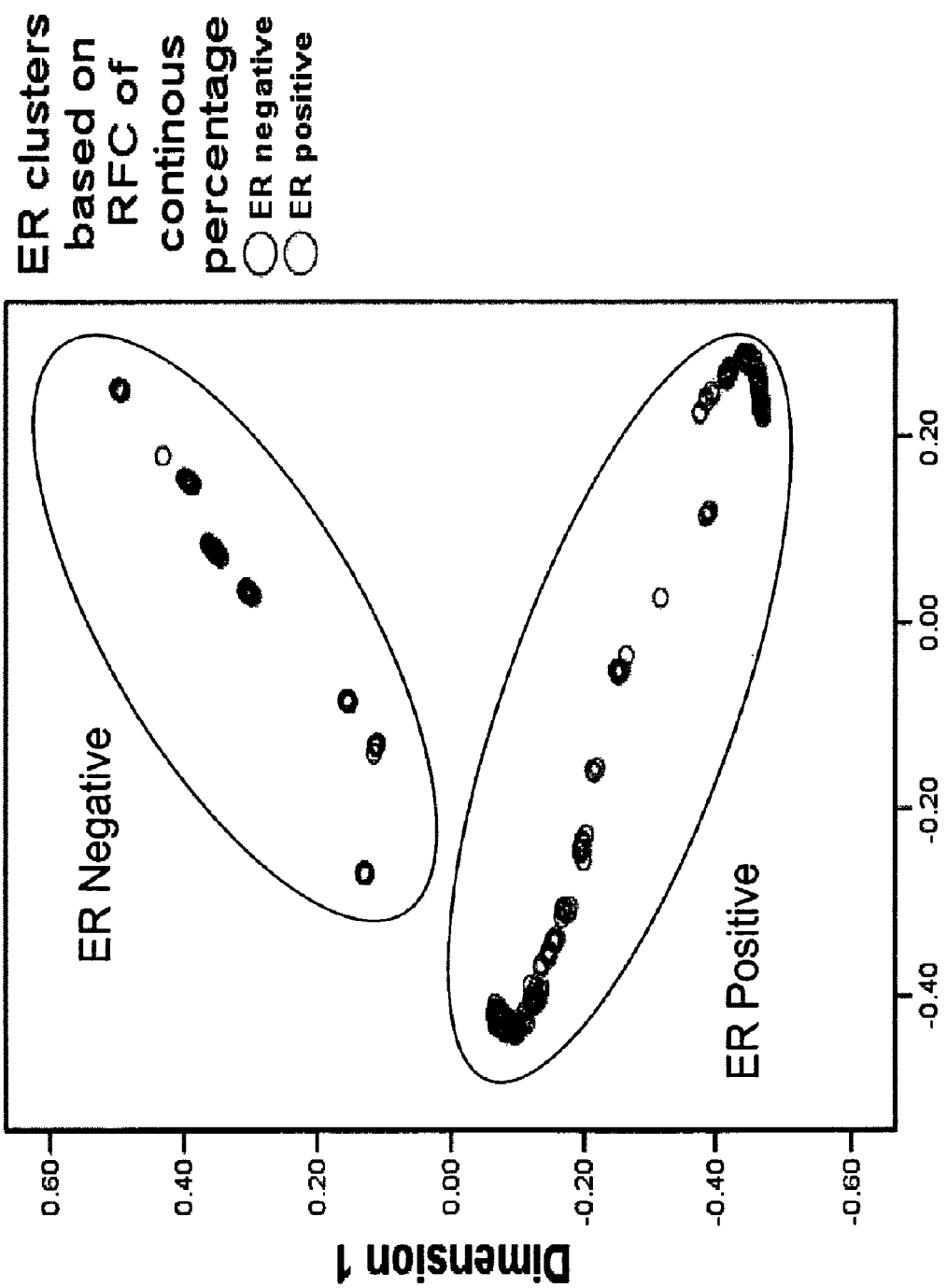
FIGS. 4A to 4F are graphs showing the ER and PR automated cut-off finding using RFC (Random Forest Clustering)
Figure 4B:
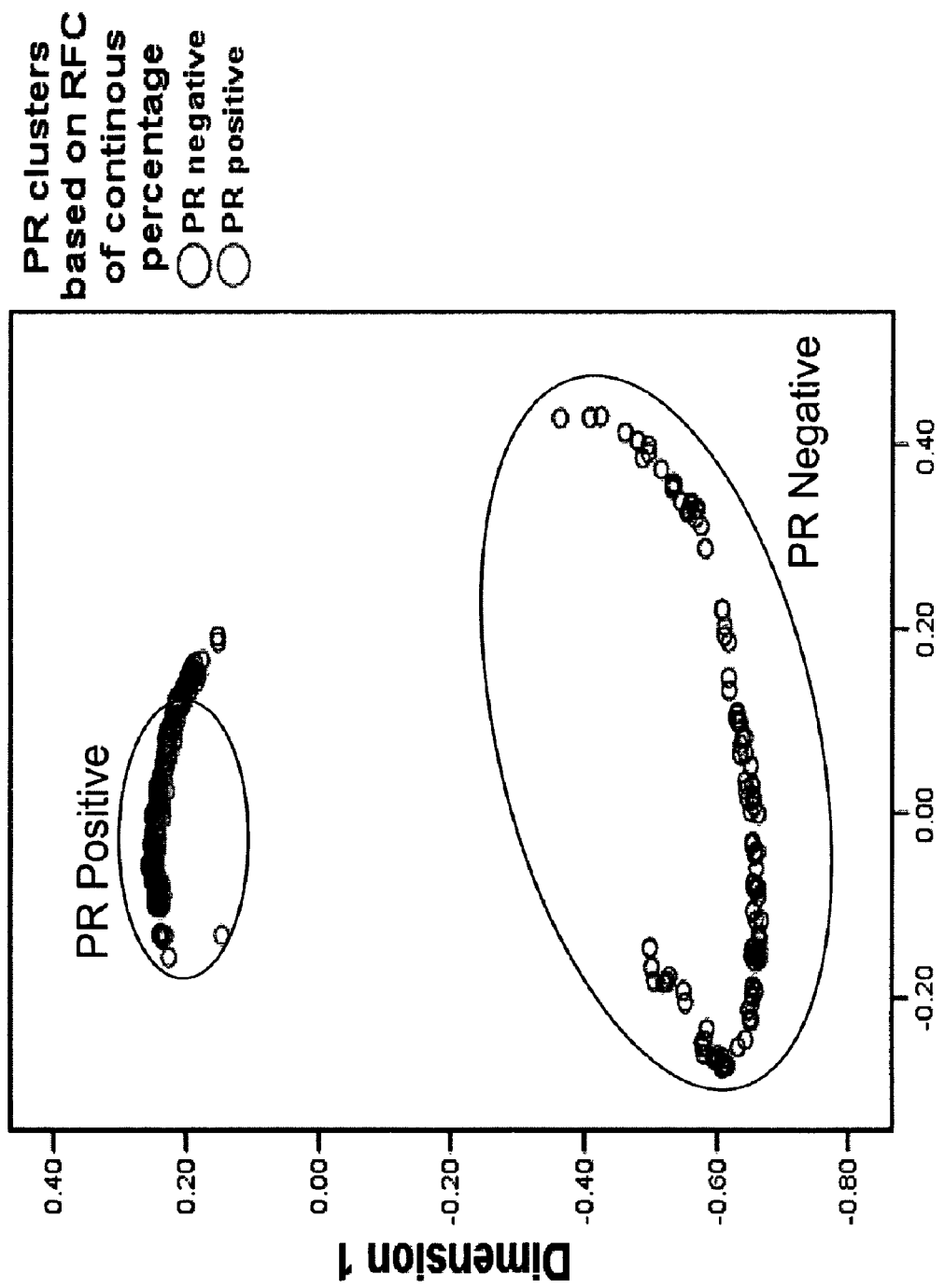
Figure 4C:
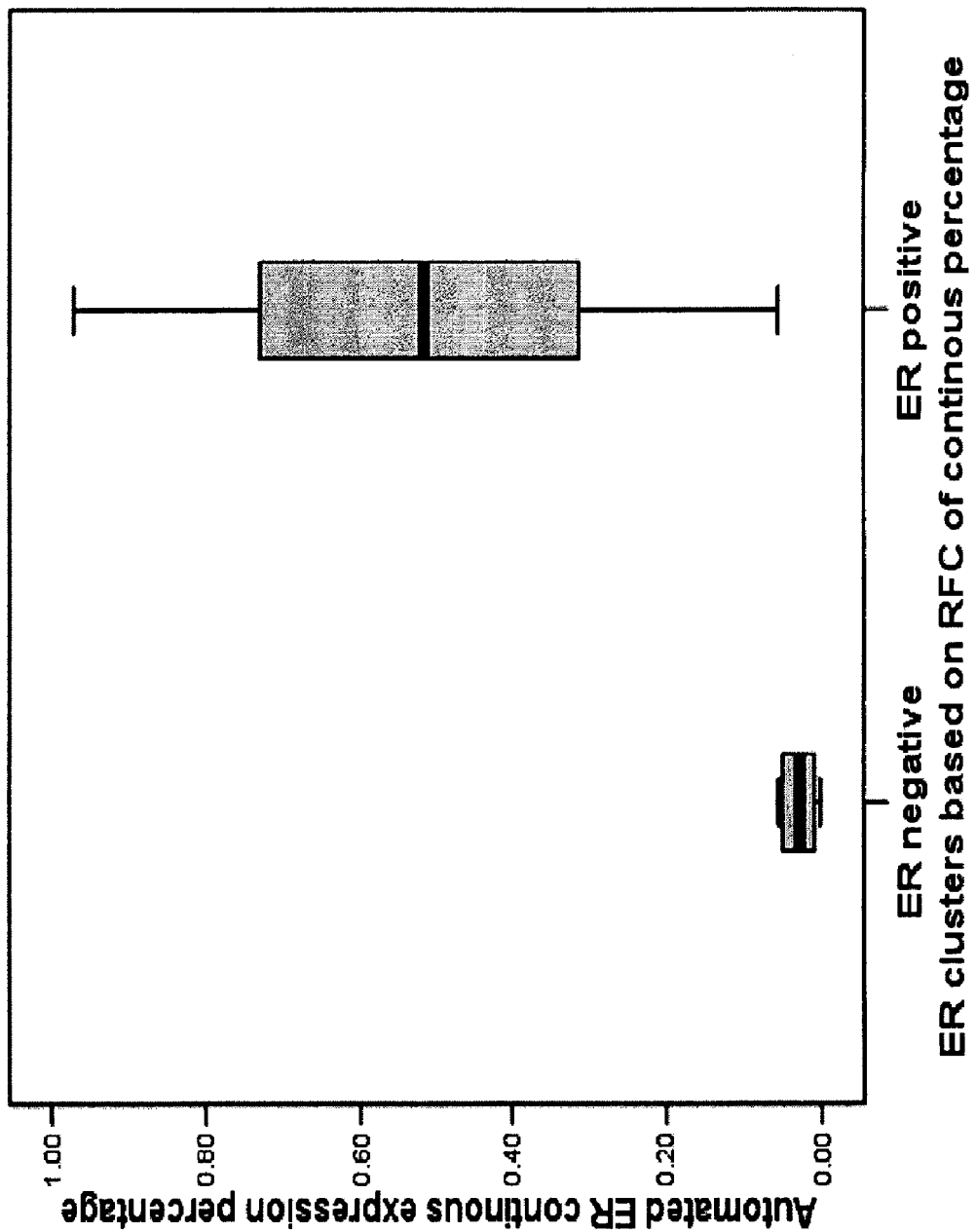
Figure 4D:
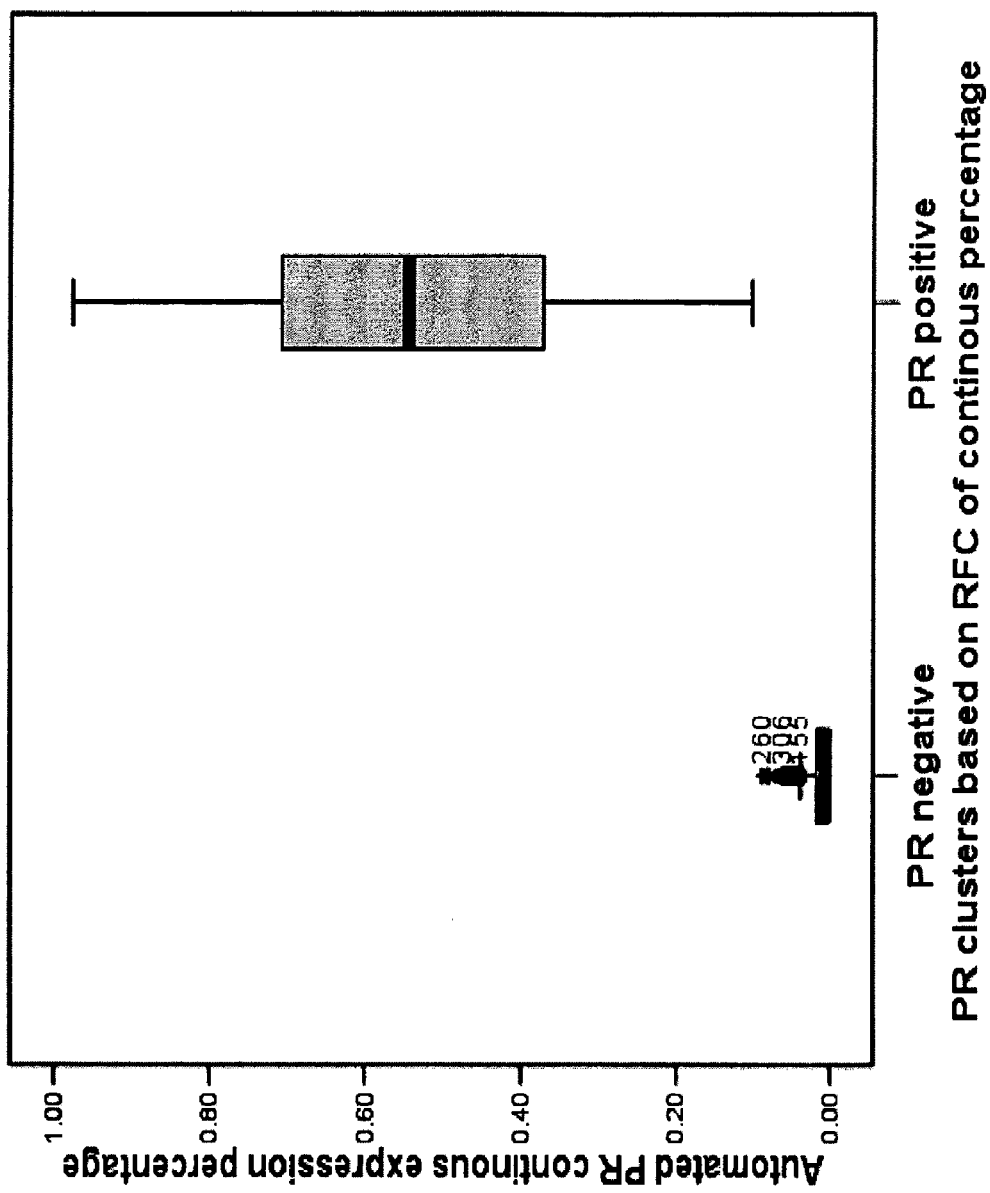
Figure 4E:
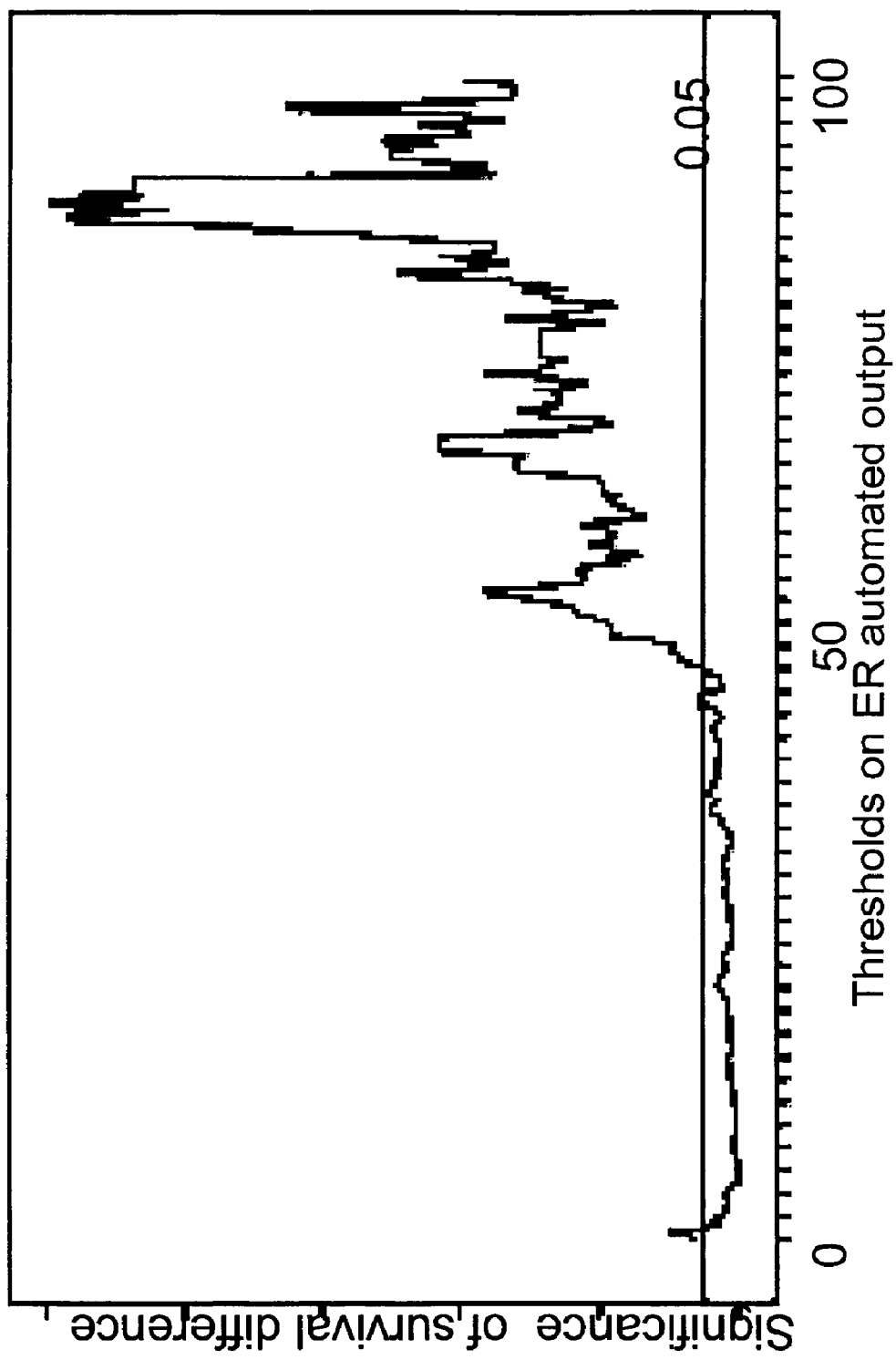
Figure 4F:
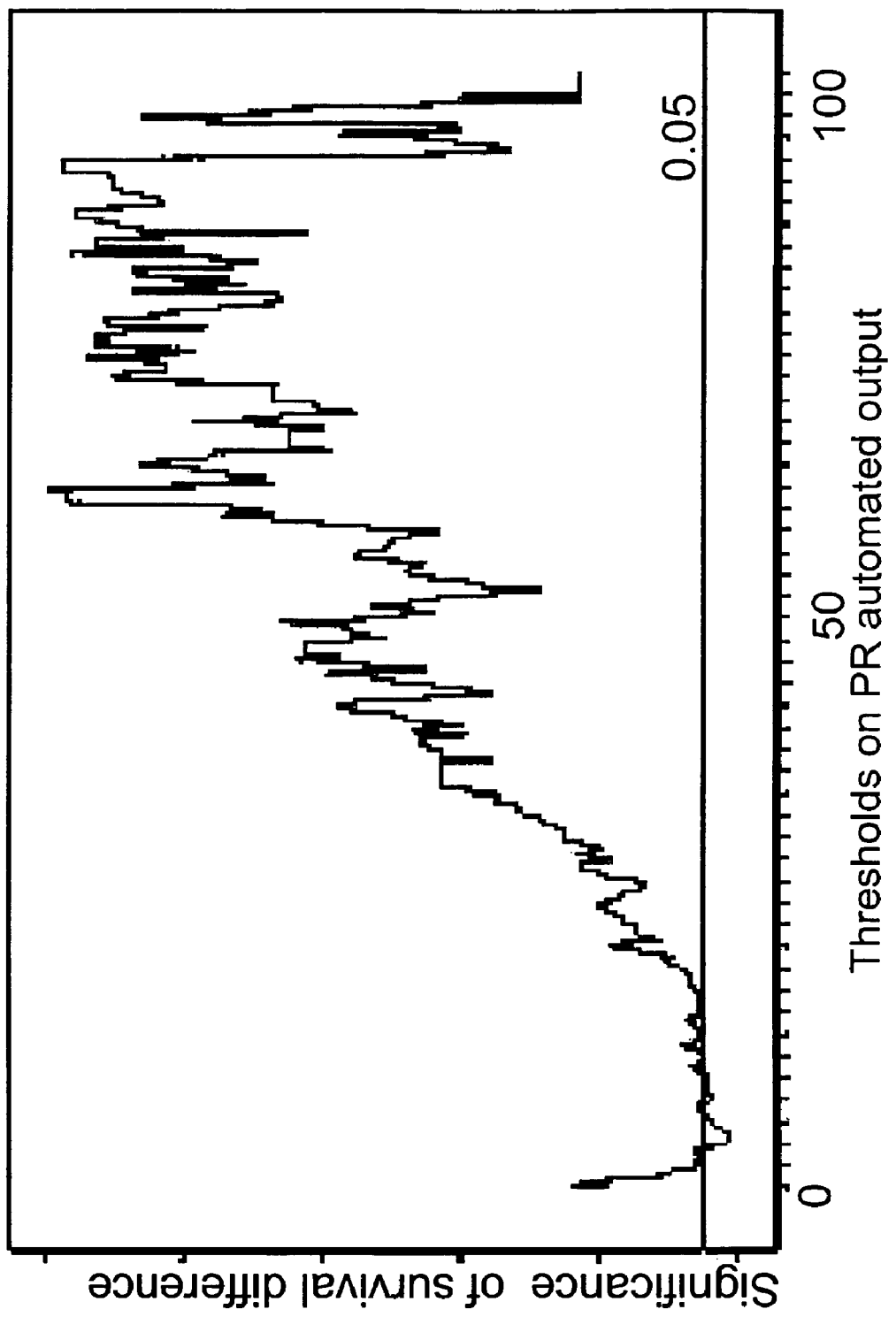

RFC was initially performed on the continuous ER or PR expression as determined by image analysis. This revealed two distinct clusters for both ER and PR expression data. FIG. 4A shows negative and positive ER clusters using automated scores. FIG. 4B shows negative and positive PR clusters using automated scores. FIGS. 4C and 4D show the ER and PR scores distribution within the negative and positive clusters. FIGS. 4E and 4F show the automated ER and PR cut-off selection using the significance of difference from Kaplan-Meier survival analysis. Data shown is for Cohort I however a similar pattern was seen in all three cohorts. The distribution of ER and PR expression as determined by image anaysis within each cluster is illustrated in FIG. 4B, which demonstrates that cluster A consisted of a group of patients (n=158) with low levels of ER (mean=3%, SEM=2%) and cluster B (n=287) had high levels of ER expression (mean=51%, SEM=26%). A similar pattern was seen for PR. The ER and PR status, as determined by manual analysis, was then examined within the clusters (Table 4). This revealed that 17(4%) tumours which would have been considered to be ER positive following manual analysis clustered with the ER negative tumours, and 31 (7%) tumours which would have been considered to be PR positive following manual analysis clustered with the PR negative tumours.

In an effort to validate our findings following RFC, we analysed the continuous ER and PR data and examined 300 different cut-offs for survival analysis. This revealed that 7% positive nuclei was the optimum cut-off for ER and 5% positive nuclei was the optimum cut-off for PR, which corresponded exactly with our initial findings. Data were thus dichotomized based on the clusters outlined above, using a cut-off of 7% for ER and 5% for PR. BCSS, OS and RFS survival difference between each cluster was investigated for ER and PR in each cohort. In all three cohorts a 7% cut-off as determined by RFC for ER was associated with a lower HR as compared to 10% cut-off based on either automated or manual analysis (Table 5). A 5% cut off for PR was associated with similar HRs as manual analysis. However, a 10% cut-off as determined by image analysis was not associated with a significant outcome. We proceeded to utilise the untreated arm of Cohort I to investigate the true prognostic potential of a 7% cut-off for ER and a 5% cut off for PR (Table 6). This revealed that manual analysis using a 10% cut-off was associated with a HR of 0.64 (95% CI 0.46-0.81, p<0.01), however a 5% cut off as determined following RFC was associated with a lower HR and narrower confidence intervals (HR=0.59, 95% CI 0.44-0.77, p<0.01) indicating a 7% cut off may be a stronger prognostic indicator in premenopausal women. The 7% cut-off for PR was not associated with an improved HR as compared to manual analysis, which could be attributed to the heterogenous pattern of staining as described above.

Results 2(D)

Automated Analysis of ER/PR Expression and Predicting Tamoxifen Response

Figure 5A:
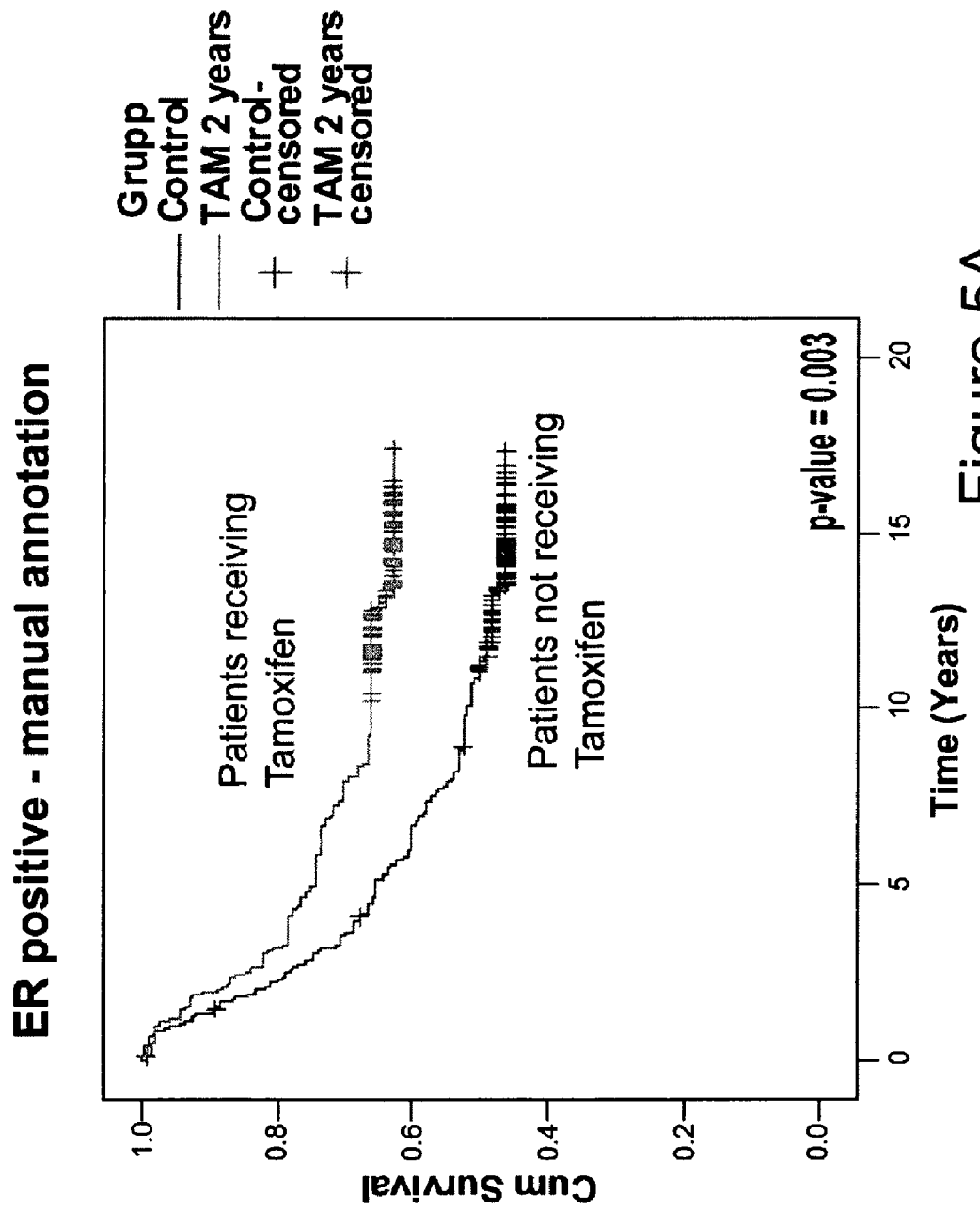
Figure 5B:
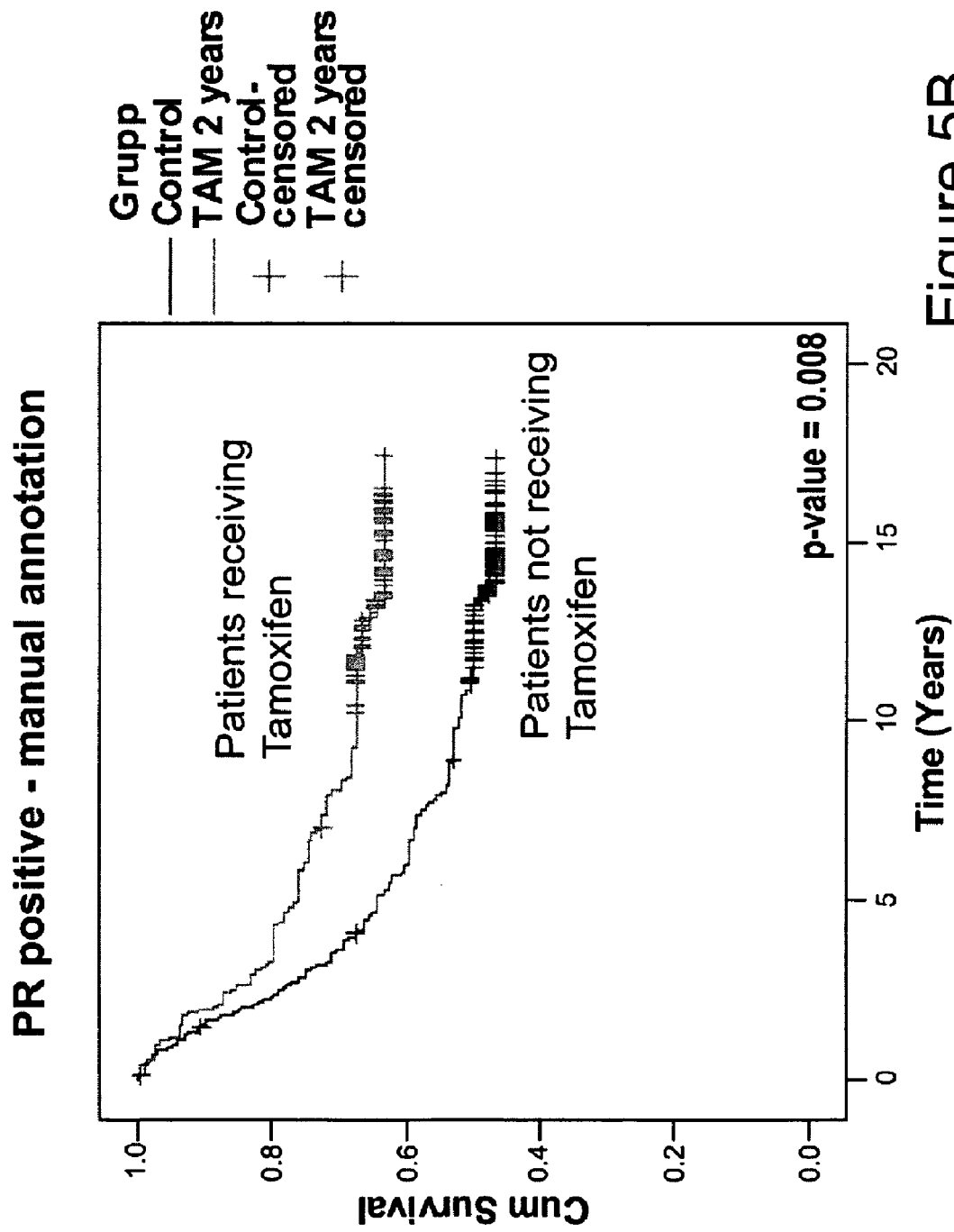
Figure 5D:
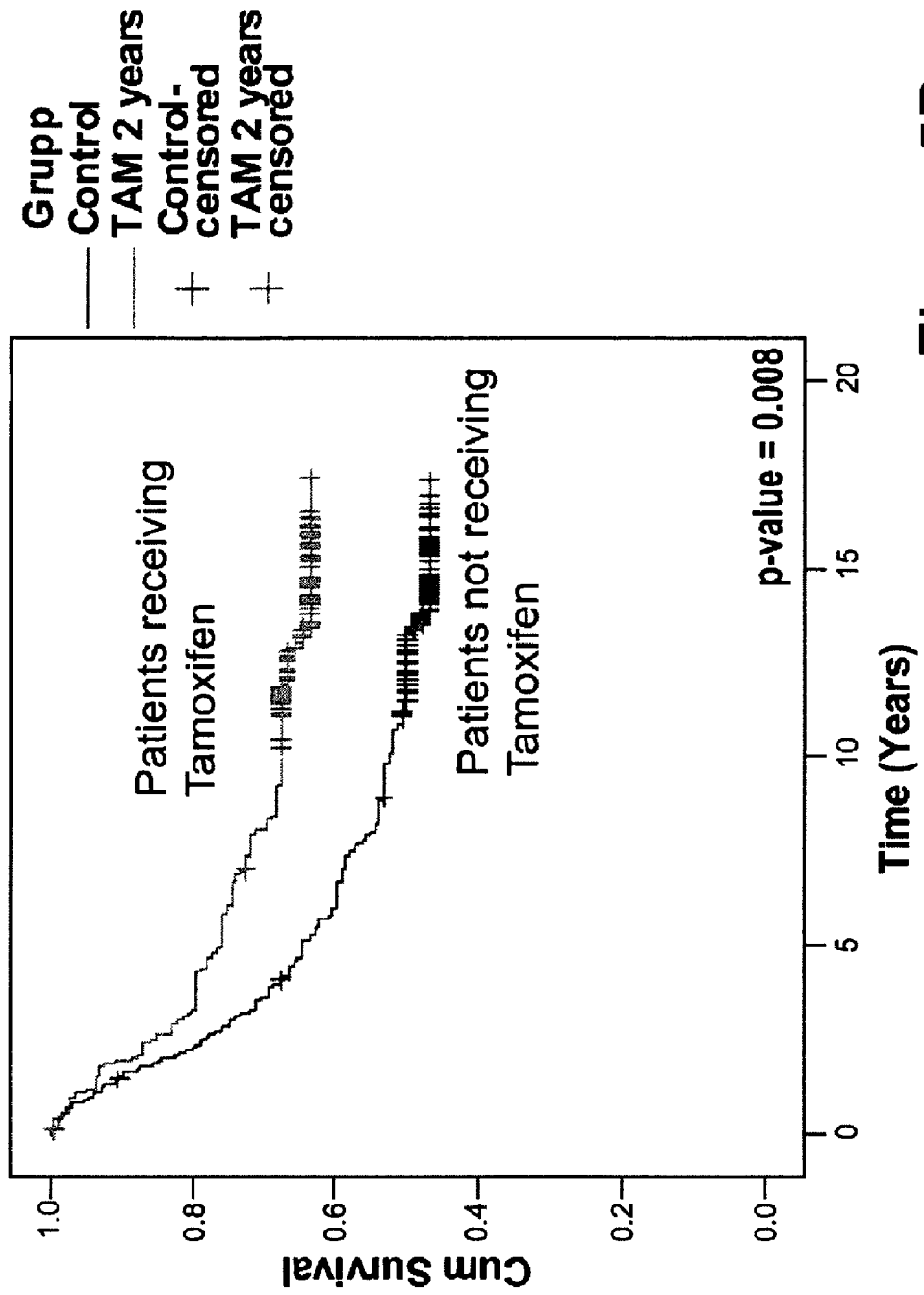

Having demonstrated the prognostic benefit of a 5% cut-off for ER in the untreated arm of cohort I, we proceeded to investigate any relationship between RFC based analysis of automated ER/PR IHC expression data as determined by image analysis and tamoxifen response in premenopausal breast cancer patients. To do this we examined the predictive relevance of a 5% cut-off for ER and a 7% cut-off for PR in the treated arm of cohort I. FIGS. 5A and 5B are survival curves of treated and untreated patients within the ER+ and PR+ arm of the cohort as defined by RFC. FIGS. 5C and 5D are survival curves of treated and untreated patients within the ER+ and PR+ arm of the cohort as manually annotated by the pathologist. As illustrated in FIGS. 5C and 5D, there was a significant effect of 2 years tamoxifen treatment on the ER+ and PR+ cohort of patients as determined by RFC. As expected no treatment effect was evident in ER−, PR− patients as determined by RFC, thus indicating that the cut-offs are suitable for predicting tamoxifen response.

Discussion

Despite the development of numerous small molecule inhibitors and monoclonal antibodies as targeted therapy for breast cancer, there is an ongoing debate as to whether any of these new therapies will be as effective as anti-estrogens.

The concept of endocrine manipulation as a treatment of breast cancer initially arose in the 19$^{th}$ century with the first demonstration of disease regression following oopherectomy in pre-menopausal women with metastatic breast cancer by George Beatson [3]. Endocrine therapies act by antagonizing the ER or by reducing estrogen concentrations within or around tumour cells. In pre-menopausal women, serum and tissue estradiol concentrations are reduced by ovarian ablation or medical suppression by LHRH agonists. Adjuvant chemotherapy also induces ammenorhea in pre-menopausal women, supporting a beneficial endocrine effect in addition to the known cytotoxic effects [4, 5]. Both pre- and post-menopausal women benefit from 5 years treatment with tamoxifen [6]. Tamoxifen, currently the most frequently prescribed drug for the treatment of breast cancer of all stages, is a first generation non-steroidal selective estrogen receptor modulator (SERM). In the breast, tamoxifen acts as an estrogen antagonist via competitive inhibition of binding of the AF-2 domain of ER and the recruitment of corepressors rather than co-activators [7].

Current treatment guidelines for pre-menopausal women with hormone-responsive breast cancer advocate a combination of ovarian ablation/suppression or chemotherapy, followed by five years of tamoxifen [8-10]. In hormone responsive post-menopausal women, ovarian ablation/suppression has no place, as the primary source of estrogen is not from ovarian synthesis but from the conversion of androstenedione to estrone and estradiol in peripheral tissues including the breast. Data from recent large prospective randomised controlled trials involving aromatase inhibitors are now emerging and herald new standards in adjuvant endocrine treatment [11, 12]. The International Expert Consensus on the Primary Therapy of Early Breast Cancer states that tamoxifen may be an acceptable option, but that aromatase inhibitors have shown superiority over tamoxifen in early breast cancer [13]. These guidelines advocate using an aromatase inhibitor for the treatment of post-menopausal women with endocrine-responsive early-stage breast cancer.

Irrespective of their menopausal status, possibly the single most important issue for any breast cancer patient is the assessment of her tumour hormone receptor status. Hormone receptor status is routinely evaluated in all resected primary tumours to assess the levels of ER and PR. The ER and PR, like other steroid hormone receptors, play a role in developmental processes and maintenance of hormone responsiveness in target cells. From the molecular viewpoint, ER and PR interaction with target genes is of paramount importance in maintenance of normal cell function and is also involved in the regulation of mammary tumour cell function. The ER was initially identified in the 1960's and remains the only reliable predictor of endocrine responsiveness in breast cancer, and is arguably the single most important predictive biomarker in clinical oncology that exists today. Additionally one of the most studied ER-regulated genes is PR, which mediates the steroid hormone progesterone's effects on mammary gland development and tumorogenesis [1]. PR is also a member of the nuclear steroid receptor superfamily. Approximately 70-80% of all invasive breast cancers are ER-positive and thus considered likely to respond to endocrine therapy (discussed below). PR, which is positive in approximately 60% of cases, may be even more important in predicting tamoxifen response [2]. PR-positive/ER-negative tumours make up only a small percentage of tumours, but appear to respond to conventional endocrine therapy [2].

Immunohistochemistry (IHC) performed on formalin fixed tissue sections is the most commonly used assay and has replaced other biochemical-based methods using cell suspensions, which consisted of a mixture of normal and malignant tissues. IHC based hormone receptor analysis enable assessment of the tissue architecture and is also applicable on small tumours, which were often not suitable for biochemistry based assays Currently, hormone receptor status is manually assessed by a pathologist and a cut off of 10% positive cells (regardless of intensity) is used to decide whether a patient should have adjuvant hormonal therapy. Such a cut off can lead to significant intra-observer variability. Scoring systems have been introduced in order to overcome these variations, particularly for markers that are used to make therapeutic decisions (Table 1). The histochemical score (H-score) [14] was initially developed for assessment of ER, as it includes a quantitative assessment of both the intensity (0-3) of staining and the percentage of positive cells (0-100%) with a range of 0-300. It can be time consuming and tedious, and so modified scoring systems have been introduced. The quick score [15] was based on percentage range of cells staining from 1 to 4 and overall intensity as 1-3, which were added. This has generally been replaced for ER by the Alfred score which has expanded the lower range of the scale giving a range of 1-5. In practice all the scoring models have been shown to correlate with clinical outcome when used by experienced pathologists (Barnes et al. 1996; Fisher et al. 2005).

In a move away from the semi-quantitative manual scoring models currently employed, the present invention provides an automated image analysis method and system for implementing the image analysis method based on non-supervised learning steps to accurately assess the expression levels of the one or more candidate objects of interest in a large number of biological samples. Given their importance as both prognostic and predictive biomarkers in breast cancer, ER and PR were chosen as the markers of choice for this study.

Here we present data on the automated quantification of over 1,000 primary breast tumours using the newly developed unsupervised image analysis method of the present invention. Our method differs from other commercially available methods in that it doesn't require prior data for training purposes, and it uses a novel step to isolate candidate objects of interest (such as, for example, tumour cells) from objects which are not of interest, such as background stroma cells.

We performed some direct comparisons of our method to other commercially available methods (data not shown) and found that it out-performed these methods, particularly in the identification of negatively stained candidate objects of interest, such as negatively stained tumour nuclei. Many commercially available methods appear to have difficulty in distinguishing negative tumour nuclei from background non-tumour cells, such as stromal tissue and lymphocytic infiltrate. One approach to overcome this particular problem is to use a fluorescent based system such as the AQUA system, whereby stroma and tumour are labeled using different cytokeratins (Camp et al, 2002 infra). However, this approach has the drawback that it requires specific hardware and additional tissue sections, whereas a bright-field approach opens up the opportunity of using previously stained sections, thus allowing for the conservation of precious tissue resources.

To date most of the work on image analysis of IHC has concentrated on TMAs. In this study we have used three different TMAs. This study has allowed us to examine a number of important issues pertaining to TMAs. The TMAs used in this study were constructed using either 0.6 mm (Cohort I and II) or 1.0 mm cores (Cohort III). We saw the least number of misclassified cores in Cohort III (FIGS. 2A and 2B), which would suggest that a 1.0 mm core may be more suitable for image analysis purposes.

In addition, a novel step is presented as a post-image analysis processing step to address target marker heterogeneity. This post-image analysis approach used a two-step approach based on initial PCA analysis and then a hierarchical clustering to investigate the expression patterns between duplicate cores. This post image analysis approach revealed that ER displayed a much more homogenous pattern of expression than PR (FIG. 3), which has quite a heterogenous pattern of expression. Our data are in agreement with other studies. In a review of 5,993 cases Nadjii et at demonstrated that ER displayed a homogenous pattern of expression in 92% of cases, whilst PR displayed a heterogeneous pattern of expression in 21% of cases (ref PMID 15762276).

Another aim of this study was to identify new cut-offs and validate currently used cut-offs for ER and PR using an unsupervised clustering approach. There has been much debate in the literature regarding optimal cut-offs for ER and/or PR when deciding whether patients should be commenced on anti-endocrine therapy. Currently a cut off of 10% positive cells is used to decide whether a patient should have adjuvant hormonal therapy. Such a cut off can lead to significant intra-observer variability.

The novel approach was to combine a known step, that is a known post image analysis method step using Random Forest Clustering (RFC) step, with the image analysis method of the present invention. This revealed an optimal cut-off for survival analysis of 7.0% for ER and 5.0% for PR. Interestingly the 7.0% cut-off for ER was associated with an improved hazard ratio (HR) when compared to a manual 10% cut-off in cohorts I and III and a similar hazard ratio in cohort II (Table 5). This effect was not evident for PR, which would suggest that the heterogenic pattern of expression of PR may have affected the image analysis output. The true prognostic power of the new cut-offs was investigated in the untreated arm of cohort I and this confirmed our findings regarding both markers (Table 6).

In summary, in the cancer field, the implementation of the image analysis method of the present invention has already been finalized. We have demonstrated herein that the image analysis method of the present invention and the system implementing the image analysis method of the present invention can be successfully applied it to a cohort of 1,400 breast cancer patients tissue samples stained with both anti-ER and anti-PR antibodies. For all these patients, a cross-comparison between manually assessed data and automated data was carried out. The results showed that:

(i) the automated data are as good as the manual data; and
(ii) the continuous output from the automated analysis can be used to find new thresholds to determine if a patient is ER/PR positive or negative (the current threshold used by pathologists for both ER and PR being 10% and tumours are scored as being either positive or negative based on the 10% threshold).

More specifically:
(i) the image analysis method of the present invention demonstrates an excellent correlation between percentage positive tumour nuclei as determined by this image analysis method when compared to manual analysis by a pathologist;
(ii) using more than 1000 patients, an excellent correlation was seen between dichotomized Estrogen Receptor (ER) and Progesterone Receptor (PR) as determined by the image analysis method and a manual assessment (0-10% v 11-100%);
(iii) a Cox-univariate regression analysis of OS showed no significant difference in the Hazard Ratios (HRs) when calculated using either the manual or the automated image analysis method;
(iv) the image analysis method of the present invention is useful for analyzing ER and PR heterogeneity in Tissue Mircoassays (TMAs) as the results show that PR is more heterogeneous than ER;
(v) the image analysis data may be processed using post image analysis methodology, such as RFC which has utility in investigating new prognostic subgroups of patients not detectable using manual scoring systems; and
(vi) using the automated image analysis method of the present invention in combination with Random Forest Clustering (RFC) which, as a post-image analysis step, the threshold for defining the ER and PR status of a patient may be defined automatically as a good correlation between the manual and automated methods for predicting tamoxifen response was obtained.

In the past, patients with >/=10% positive cells would typically be considered for adjuvant hormonal therapy. Now, by applying our improved image analysis method, a variety of different thresholds and their effect on patient outcome may be assessed using this improved automated method. We found that the threshold of 10% in the continuous data correlated well to the clinical outcome of the same threshold in the manual data. Moreover, surprisingly, we found that a threshold of 7.0% in ER and 5% in PR continuous data is as good as 10%. This would suggest that more optimal thresholds can be identified using the continuous data produced by the image analysis method of the present invention.

In a clinical context, the image analysis method and the system for implementing the image analysis method of the present invention may be used as a diagnostic aid for quantifying the level of expression of one or more candidate objects of interest on full-face section sections. Using other technologies in the market for slide scanning, a selection of an area of interest may be made on the digital slide of a full-face section. Afterwards, a pathologist could either confirm the continuous output of the image analysis method or reject it on the present area of interest and estimate it by eye.

In a research context, the image analysis method and system for implementing the image analysis method of the present invention may be used to screen a cohort of patient samples for tissue samples that are either negatively stained for the one or more candidate objects of interest or that are clearly positively stained for the one or more candidate objects of interest. When applied to TMAs, the image analysis method may be used to predict the level of expression of each candidate object of interest and a pathologist may validate the output as continuous variable on those cores. In particular, the image analysis method can easily be utilised to examine expression levels of a range of candidate objects of interest which are biomarkers for different disease states.

TABLE 1

Clinicopathological Characteristics of Patients in three cohorts used in this study

|  | Cohort 1 (n = 564) | Cohort II (n = 512) | Cohort III (n = 179) |
|---|---|---|---|
| Age |  |  |  |
| Median (Range) | 45 (25-57) | 65 (27-96) | 65 (35-97) |
| Tumour Size |  |  |  |
| ≤20 mm | 208 (37) | 312 (63) | 105 (59) |
| >20 mm | 356 (63) | 191 (37) | 74 (41) |
| Missing |  |  |  |
| Grade |  |  |  |
| I | 58 (10) | 127 (25) | 38 (21) |
| II | 222 (40) | 213 (42) | 79 (44) |
| III | 234 (42) | 170 (33) | 62 (35) |
| Missing | 50 (8.9) | 2 |  |
| Histological Type |  |  |  |
| Indeterminate | 7 (2) | 34 (7) | 3 (2) |
| IDC | 411 (73) | 338 (66) | 125 (70) |
| ILC | 43 (7.6) | 73 (14) | 31 (17.3) |
| Tubular | 5 (1) | 34 (7) | 16 (8.9) |
| Medullary | 25 (4) | 15 (3) | 4 (2.2) |
| Mucinous | 3 (1) | 17 (3) |  |
| Missing | 70 (12) | 1 |  |
| Nodal status |  |  |  |
| Node −ve | 160 (28) | 291 (57) | 87 (49) |
| Node +ve | 402 (71) | 166 (32) | 65 (36) |
| Missing | 2 | 55 (11) | 27 (15) |
| ER status |  |  |  |
| ER +ve | 324 (57) | 407 (80) | 157 (88) |
| ER −ve | 151 (27) | 72 (14) | 22 (12) |
| Missing | 89 | 33 (6) |  |

TABLE 1-continued

Clinicopathological Characteristics of Patients in three cohorts used in this study

|  | Cohort 1 (n = 564) | Cohort II (n = 512) | Cohort III (n = 179) |
|---|---|---|---|
| PR status |  |  |  |
| PR +ve | 147 (26) | 141 (28) | 52 (29) |
| PR −ve | 312 (55) | 229 (45) | 127 (71) |
| Missing | 105 | 142 (28) |  |

TABLE 2

|  | MARKER | |
|---|---|---|
|  | ER | PR |
| COHORT I | 445 (94%) | 429 (90%) |
| COHORT II | 330 (89%) | 327 (88%) |
| COHORT III | 176 (98%) | 174 (97%) |

TABLE 3

Univariate significance of 10% cutoff of Overall Survival for ER and PR in each cohort.

|  | MC | | | AC | | |
|---|---|---|---|---|---|---|
|  | HR | 95% CI | p value | HR | 95% CI | p value |
| Cohort I |  |  |  |  |  |  |
| ER |  |  |  |  |  |  |
| OS | 0.62 | 0.465-0.826 | <0.01 | 0.646 | 0.509-0.907 | <0.01 |
| PR |  |  |  |  |  |  |
| OS | 0.636 | 0.474-0.853 | <0.01 | 0.719 | 0.538-0.961 | 0.03 |
| Cohort II |  |  |  |  |  |  |
| ER |  |  |  |  |  |  |
| OS | 0.729 | 0.523-1.015 | 0.06 | 0.847 | 0.584-1.229 | 0.38 |
| PR |  |  |  |  |  |  |
| OS | 0.607 | 0.458-0.806 | <0.01 | 0.849 | 0.673-1.188 | 0.43 |
| Cohort III |  |  |  |  |  |  |
| ER |  |  |  |  |  |  |
| OS | 0.259 | 0.127-0.530 | <0.01 | 0.154 | 0.067-0.355 | <0.01 |
| PR |  |  |  |  |  |  |
| OS | 0.307 | 0.158-0.597 | <0.01 | 0.361 | 0.183-0.712 | <0.01 |

OS: Overall survival;
MC: Survival analysis using manual (<10%, >10%) pathologist based assessment;
AC: Survival analysis using automated continous (threshold at 10% i.e <10%, >10%) based Assessment;
NA: clinical data not available;
HR: Hazard ratio of survival analysis using Cox regression analysis.
CI: Confidence interval for the hazard ratio.
c: Higher confidence interval for the hazard ratio.

TABLE 4

Number of tumours within ER−/+ and PR−/+ in cohort I as defined by the manually pathologist based annotation and the automated clustering.

| | MANUAL | | | CLUSTER AUTOMATED | | |
|---|---|---|---|---|---|---|
| | Total tumours | Mean percent | STD of mean | Total tumours | Mean percent | STD of mean |
| ER | | | | | | |
| − | 141 | 4% | 5 | 158 | 3% | 2 |
| + | 304 | 48% | 29 | 287 | 51% | 26 |
| PR | | | | | | |
| − | 142 | 6% | 15 | 171 | 1% | 2 |
| + | 282 | 46% | 28 | 253 | 53% | 22 |

TABLE 5

Prognostic effect of the automatically found thresholds for ER and PR comparing to both manual and 10% cutoff.

| | OS | | | | | | | | |
|---|---|---|---|---|---|---|---|---|---|
| | Clusters | | | Automated 10% | | | Manual 10% | | |
| | HR | 95% CI | p value | HR | 95% CI | p value | HR | 95% CI | p value |
| Cohort I | | | | | | | | | |
| ER | | | | | | | | | |
| OS | 0.631 | 0.480-0.830 | 0.001 | 0.646 | 0.509-0.907 | <0.01 | 0.62 | 0.465-0.826 | <0.01 |
| BCSS | 0.592 | 0.445-0.787 | <0.01 | 0.664 | 0.492-0.898 | <0.01 | 0.677 | 0.494-0.928 | 0.01 |
| RFS | 0.701 | 0.538-0.914 | 0.009 | 0.797 | 0.603-1.054 | 0.11 | 0.714 | 0.540-0.943 | 0.009 |
| PR | | | | | | | | | |
| OS | 0.705 | 0.524-0.947 | 0.02 | 0.719 | 0.538-0.961 | 0.03 | 0.636 | 0.474-0.853 | <0.01 |
| BCSS | 0.673 | 0.495-0.916 | 0.012 | 0.7 | 0.518-0.947 | 0.02 | 0.602 | 0.445-0.814 | <0.01 |
| RFS | 0.791 | 0.593-1.054 | 0.109 | 0.797 | 0.603-1.053 | 0.79 | 0.73 | 0.549-0.972 | 0.03 |
| Cohort II | | | | | | | | | |
| ER | | | | | | | | | |
| OS | 0.857 | 0.639-1.149 | 0.285 | 0.847 | 0.584-1.229 | 0.38 | 0.729 | 0.523-1.015 | 0.06 |
| BCSS | 0.775 | 0.476-1.264 | 0.3 | 0.536 | 0.310-0.925 | 0.02 | 0.496 | 0.297-0.827 | <0.01 |
| RFS | 0.637 | 0.411-0.988 | 0.044 | 0.625 | 0.377-1.052 | 0.077 | 0.706 | 0.447-1.209 | 0.22611 |
| PR | | | | | | | | | |
| OS | 0.853 | 0.638-1.142 | 0.285 | 0.849 | 0.673-1.188 | 0.43 | 0.607 | 0.458-0.806 | <0.01 |
| BCSS | 0.555 | 0.340-0.905 | 0.018 | 0.701 | 0.438-1.122 | 0.13 | 0.333 | 0.205-0.541 | <0.01 |
| RFS | 0.788 | 0.479-1.167 | 0.2 | 1.045 | 0.670-1.628 | 0.48 | 0.470 | 0.3031-0.729 | 0.001 |
| Cohort III | | | | | | | | | |
| ER | | | | | | | | | |
| OS | 0.235 | 0.116-0.473 | <0.01 | 0.154 | 0.067-0.355 | <0.01 | 0.259 | 0.127-0.530 | <0.01 |
| PR | | | | | | | | | |
| OS | 0.386 | 0.197-0.756 | <0.01 | 0.361 | 0.183-0.712 | <0.01 | 0.307 | 0.158-0.597 | <0.01 |

OS: Overall survival;
BCSS: Breast cancer specific survival; and
RFS: Recurrence free survival.

TABLE 6

Prognostic effect of the automatically determined thresholds for ER and PR using the untreated arm of cohort I.

| | RFS | | | | | |
|---|---|---|---|---|---|---|
| | − | | | + | | |
| | HR | 95% CI | p value | HR | 95% CI | p value |
| Cohort I ER | | | | | | |
| MC | 0.906 | 0.583-1.409 | 0.662 | 0.604 | 0.429-0.849 | 0.004 |
| CC | 0.787 | 0.530-1.168 | 0.234 | 0.637 | 0.442-0.918 | 0.015 |
| PR | | | | | | |
| MC | 0.975 | 0.614-1.548 | 0.914 | 0.598 | 0.422-0.847 | 0.004 |
| CC | 0.766 | 0.494-1.190 | 0.236 | 0.652 | 0.445-0.956 | 0.028 |

OS: Overall survival;
BCSS: Breast cancer specific survival;
RFS: Recurrence free survival;
AC: Survival analysis using automated continous (threshold at 10% i.e <10%, >10%) based Assessment;
MC: Survival analysis using manual pathologist based assessment of ER and PR status;
CC: Survival analysis using automated continous clustered into ER−/+ and PR−/+ using RFC.

Example 3

This example demonstrates the utility of the present invention in another cancer type, namely bladder cancer, and using another biomarker, namely the p53 biomarker.

Bladder Arrays:

All FFPE blocks were sectioned and stained with H&E and graded by two pathologists to confirm the pathologic stage and grade of the bladder tumours. The relevant normal and tumour areas were marked and used as the donor cores for TMA construction. TMAs were constructed from FFPE tissue blocks using the Beecher Instruments® Tissue arrays. 2 mm cores were sampled in quadruplicate for each case where tissue allowed it. Two locator cores, consisting of a liver core and a normal ureter core were placed in each array. All sections were counterstained with haematoxylin.

The Aperio ScanScope instrument allows high throughput digital Image acquisition. It is an open ended system and any algorithm can be applied to images acquired using this Instrument. By using line scanning technology it provides the highest quality digital images available. Samples from forty eight bladder tumours were used for tissue microarray construction. Each patient was represented by 4 tissue cores. A total of 5 TMAs were constructed, with 48 cases and 196 2 mm cores. The mean intensity, median intensity and percent of DAB positive tumour nuclei were recorded for each tissue core. Automated output of tissue cores from the same patient were averaged together.

Autoscore was computed for each tissue core as the product of mean intensity of DAB positive tumour cells with the percent of positive stained tumor cells. Patients were grouped according to the manual score. The box plot of both the autoscore and the intensity shows an increase of the autoscore as the tumor get more aggressive, that correlate with manual analysis.

Figure 11B:
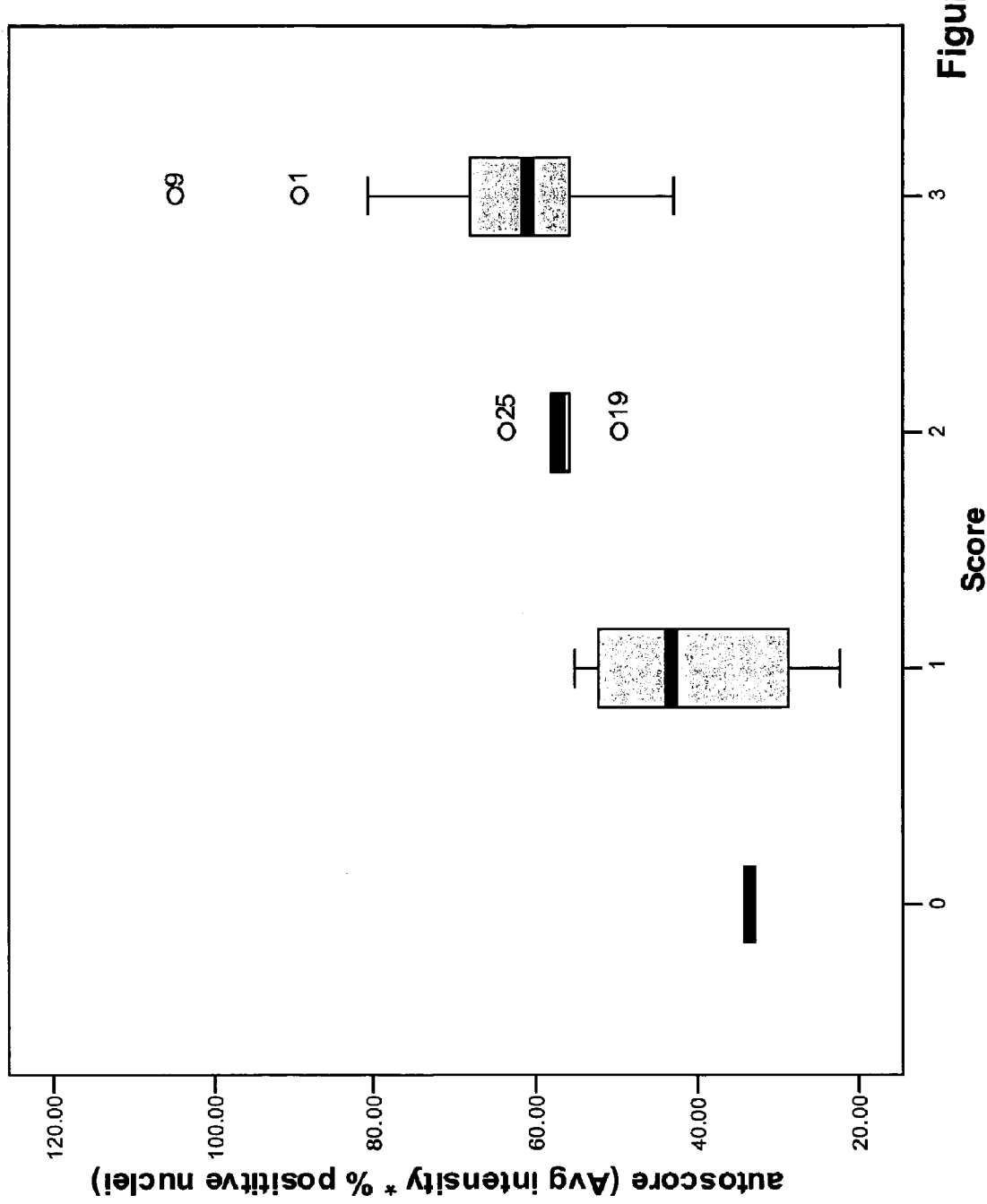

The results of our analyses are shown in FIGS. 11 and 12. FIG. 11A shows the distribution of the automated scores within the tumour grade groups following the TNM grading system. FIG. 11B shows the distribution of the automated scores within the manual scores as defined by the pathologist. FIG. 11C illustrates the distribution of the patients involved in the study within each grade group.

Figure 12A:
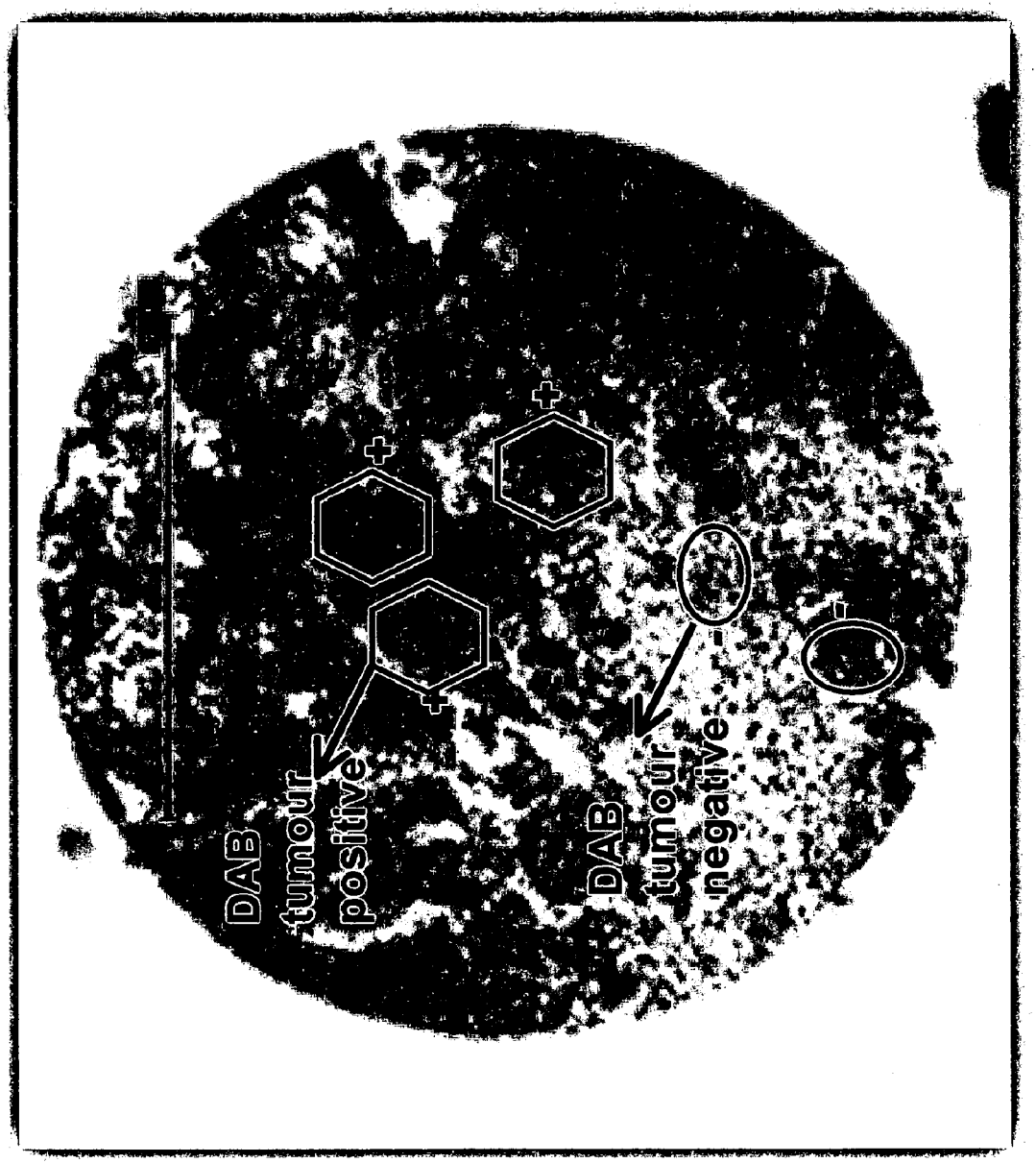
FIGS. 12A to 12D illustrate with examples the process of finding DAB positive and DAB negative tumour patterns in bladder tumour tissue.
Figure 12B:
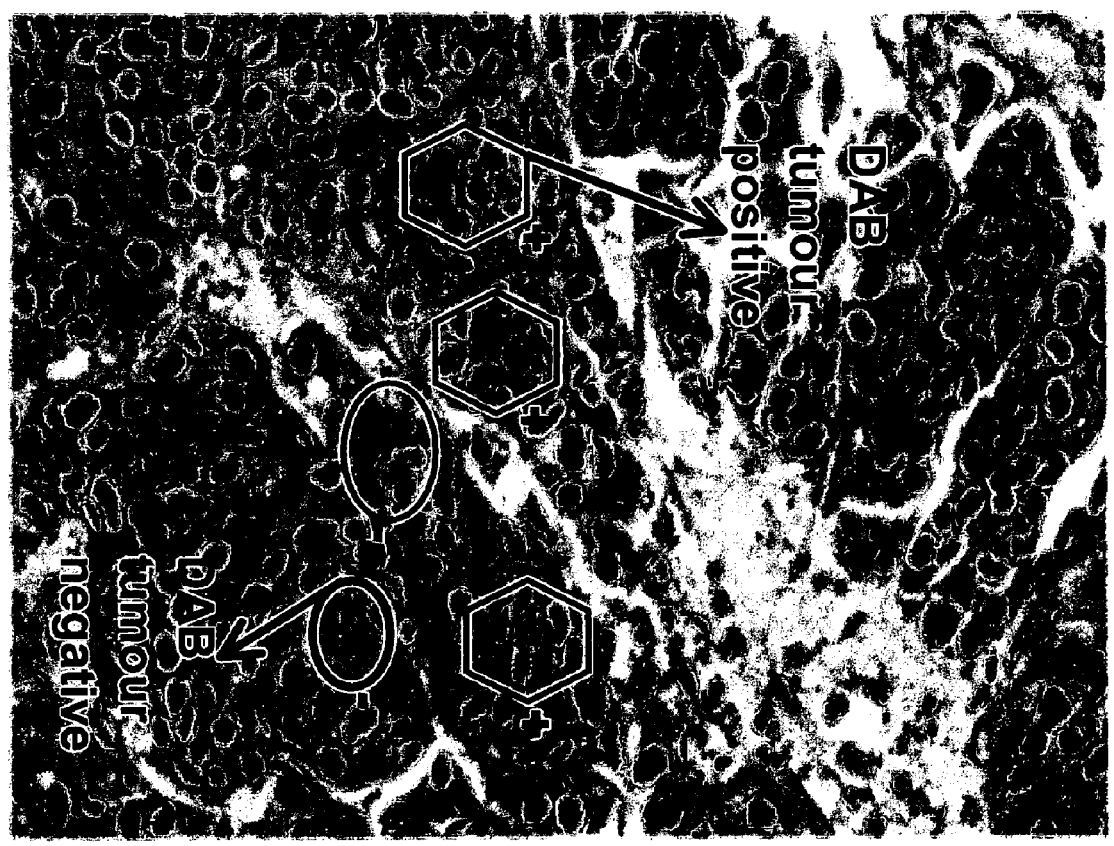
Figure 12C:
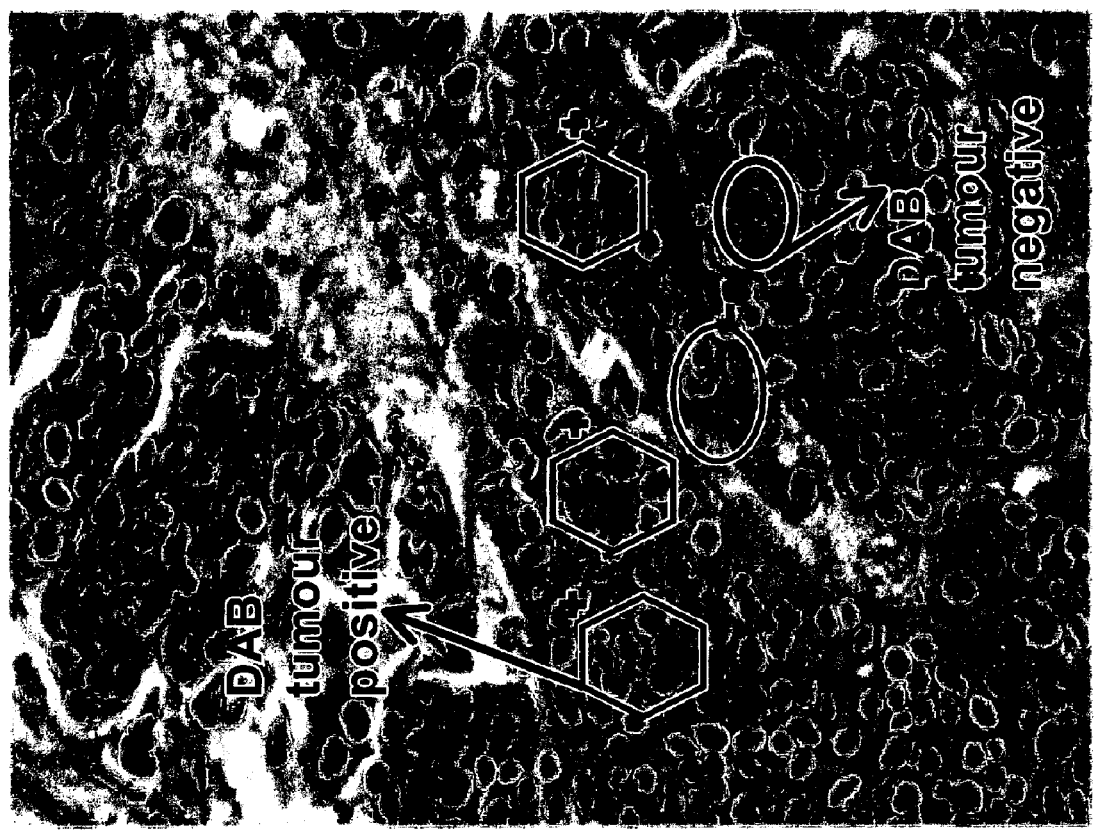
Figure 12D:
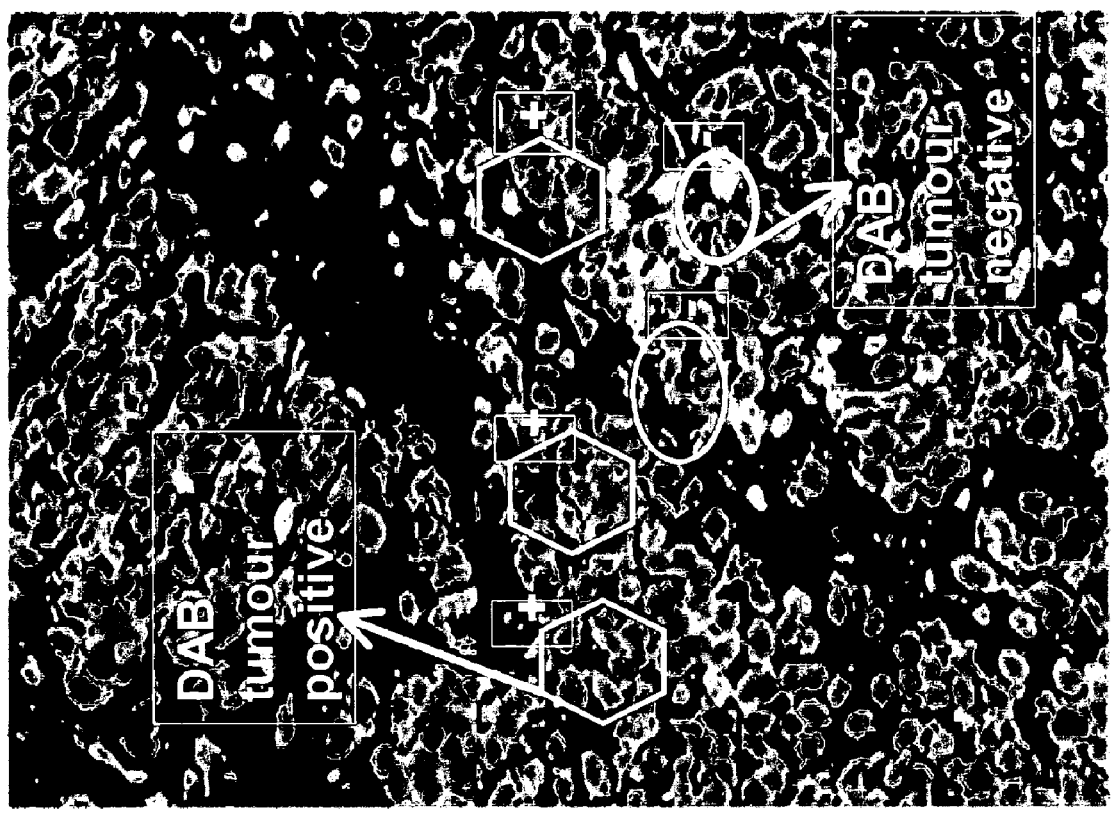
Figure 13A:
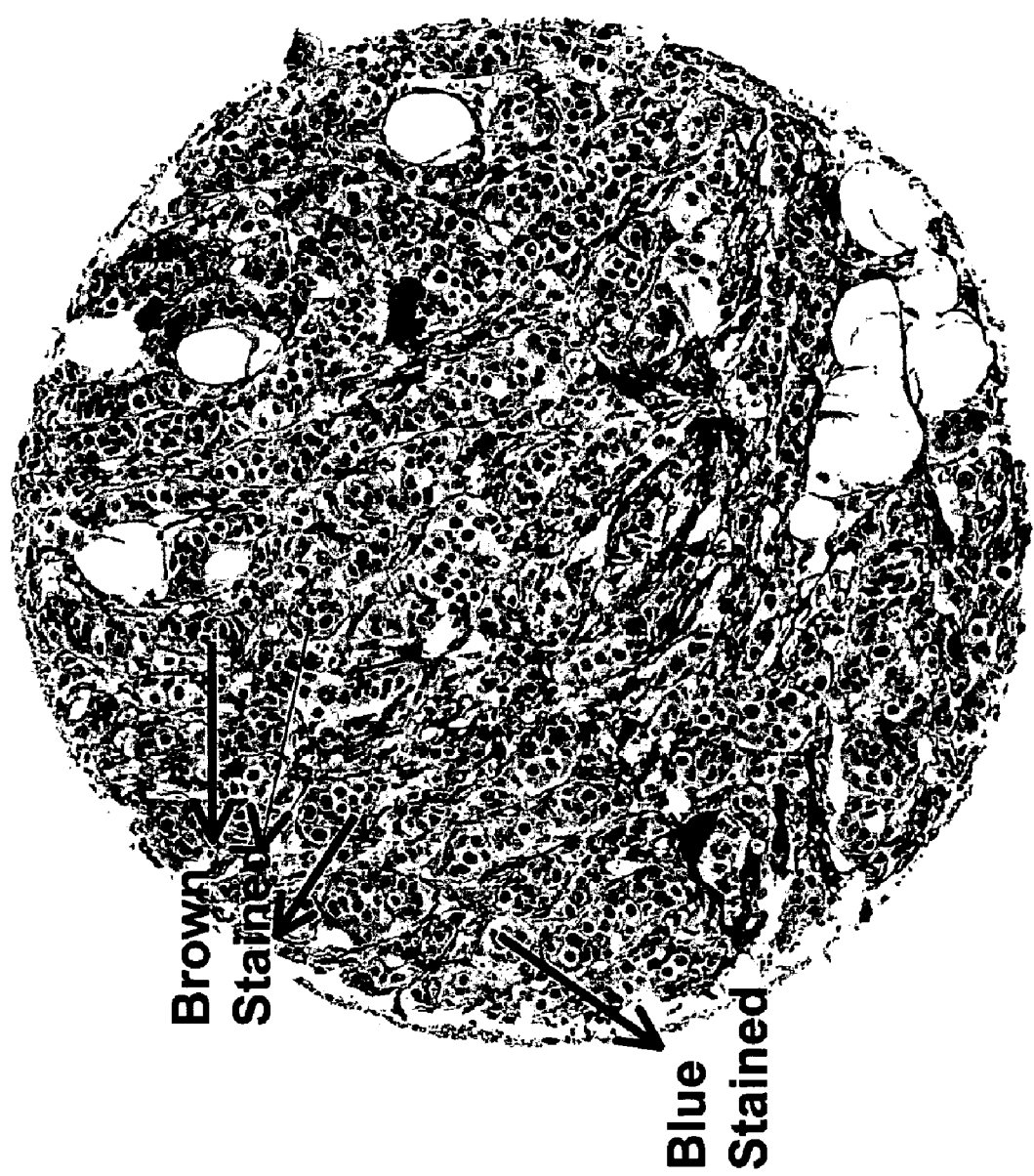
FIGS. 13A to 13F illustrate with examples the process of finding DAB positive and DAB negative tumour patterns in breast tumour tissue marked with biomarker p53 and DAB stained.
Figure 13B:
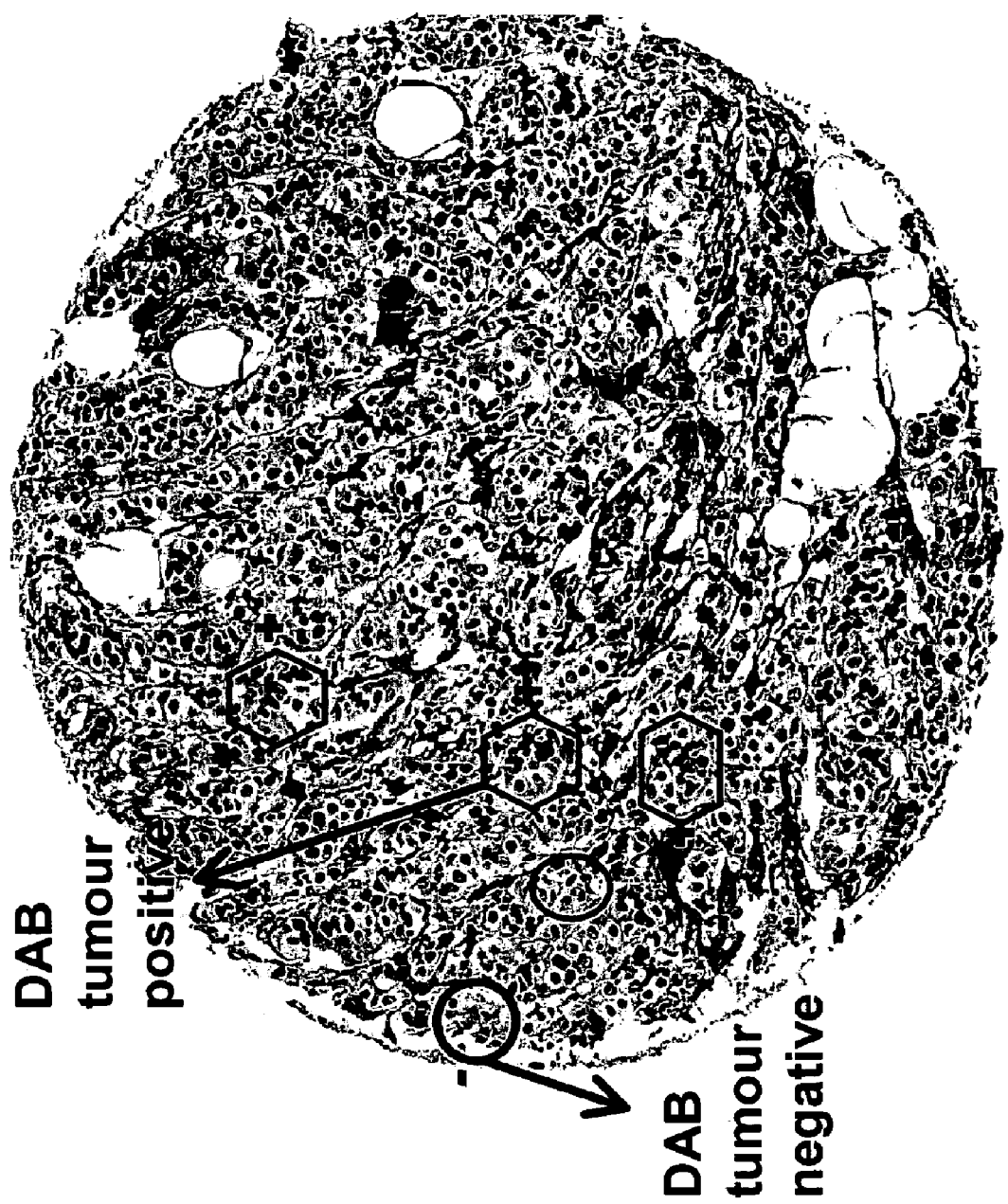
Figure 13C:
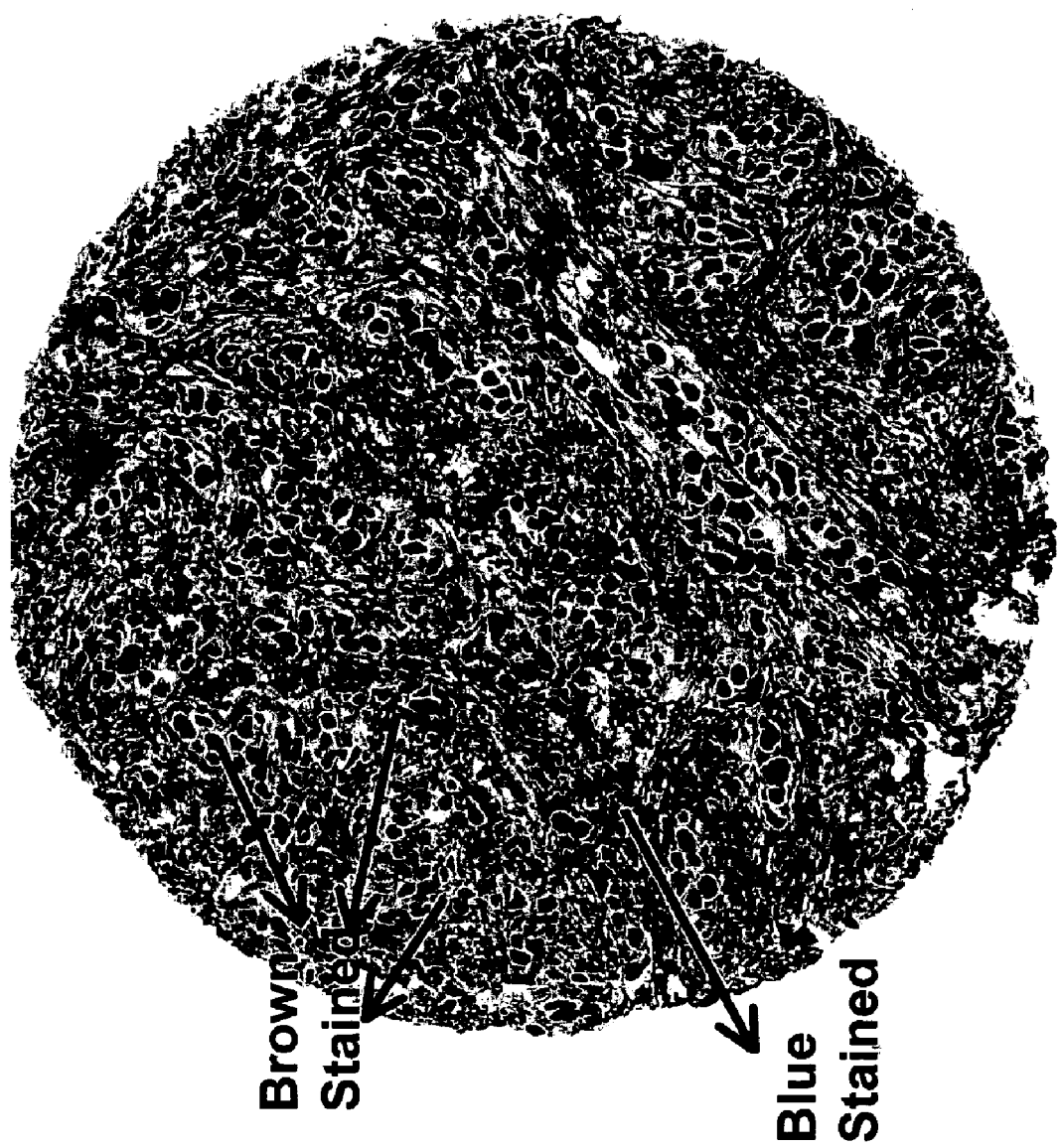
Figure 13D:
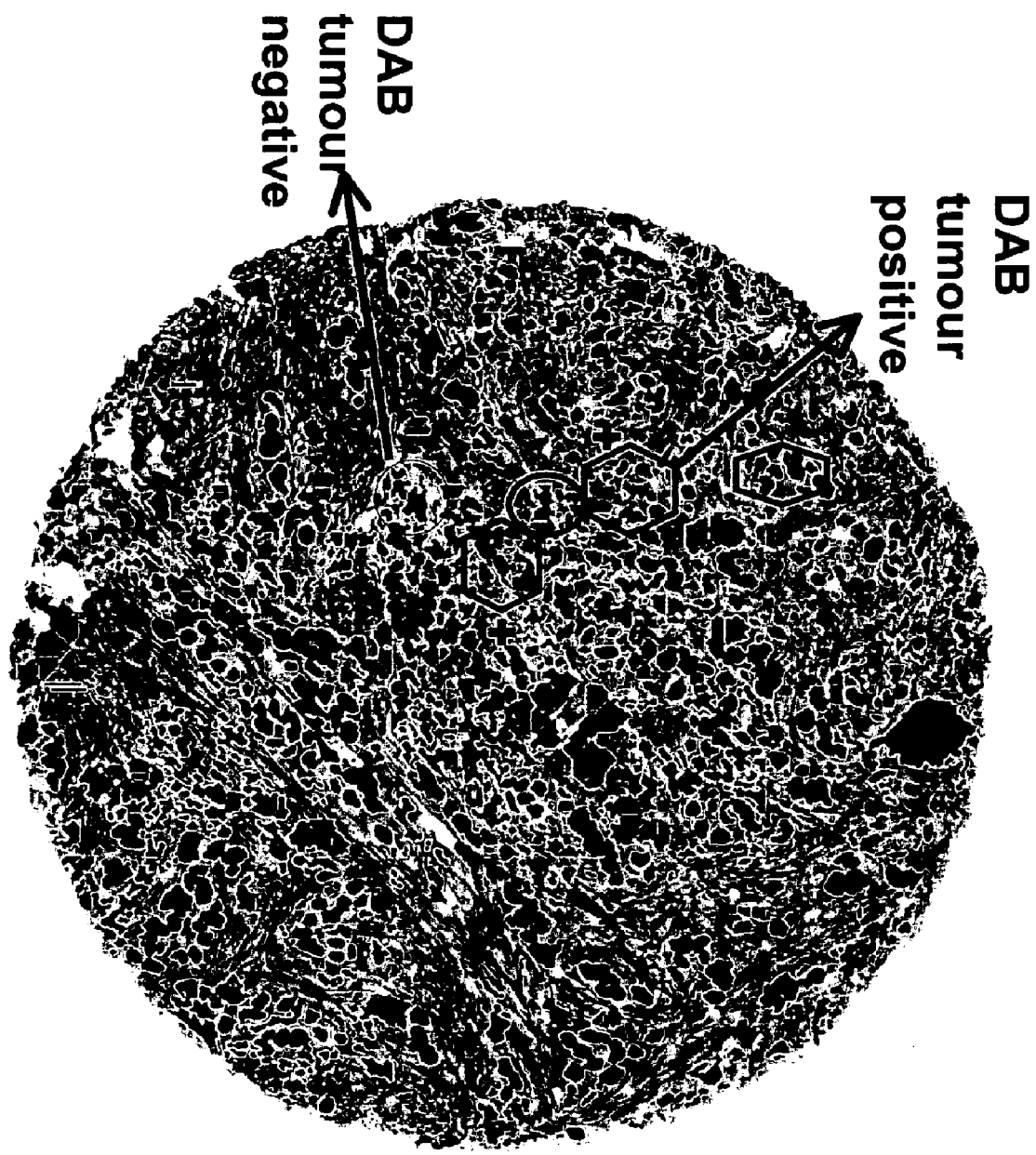
Figure 13E:
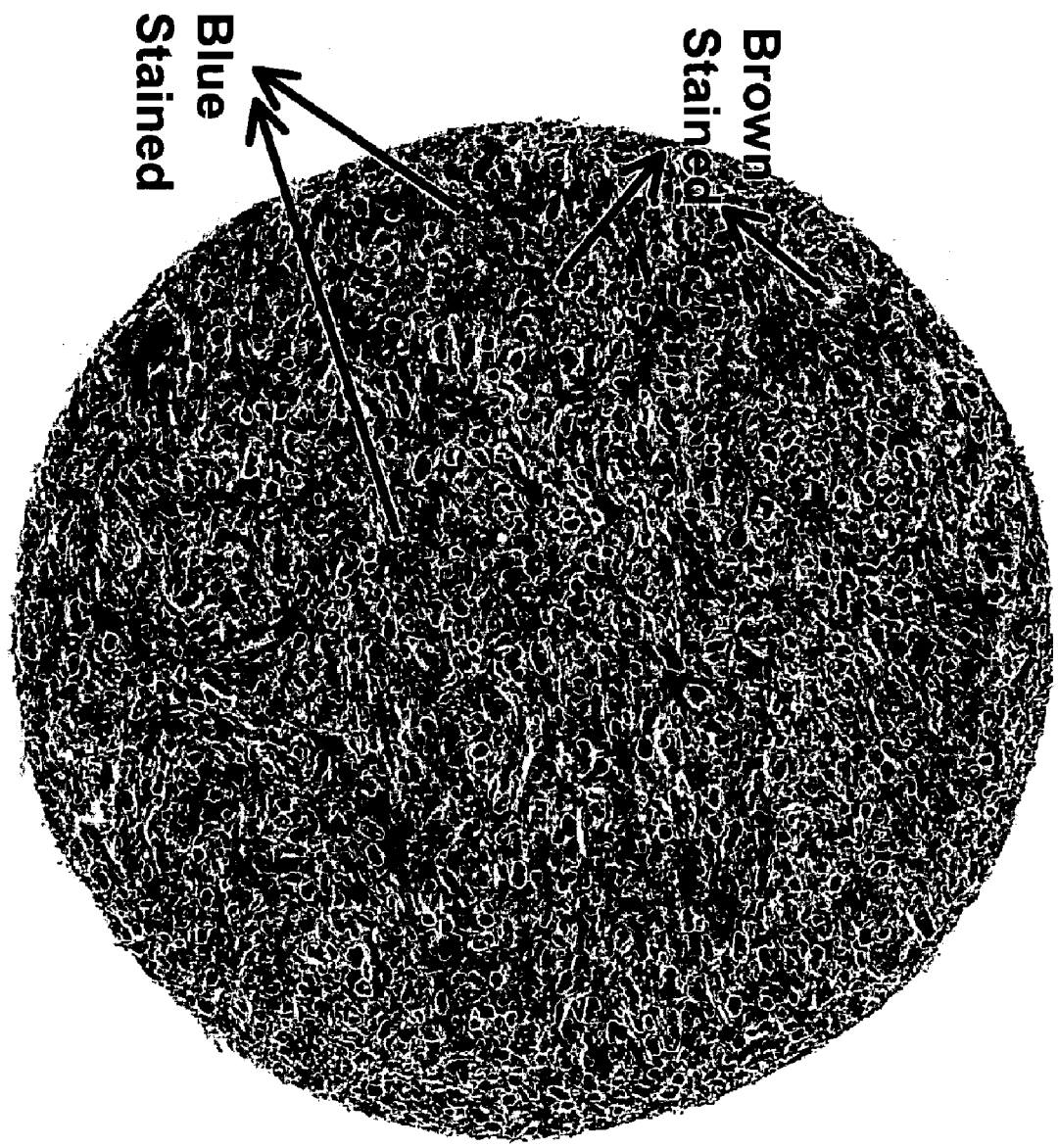
Figure 13F:
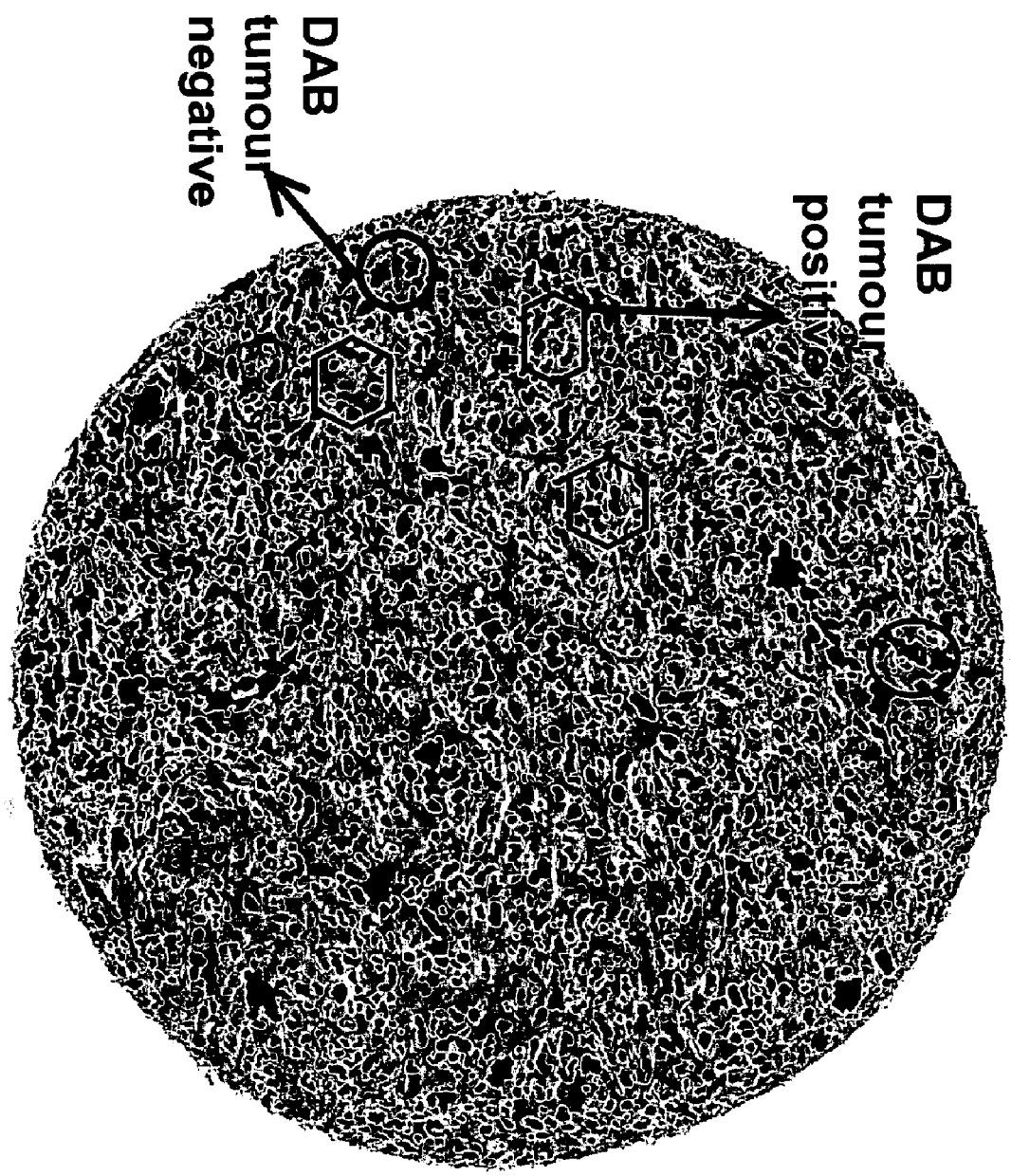

FIG. 12A shows an image of a bladder tissue core marked for the p53 biomarker and DAB stained, showing annotated areas of DAB negative and DAB positive tumour patterns. FIG. 12B/C shows a high resolution image from a section of a bladder tissue core marked for p53 with DAB positive and negative tumour areas annotated. FIG. 12D illustrates the section in FIG. 12B with tumour patterns highlighted in different shades of gray as a function of the intensity of p53 staining going from black (no staining) to white (strong staining).

Example 4

In this example, the use of biomarkers p53 and Ki67 in breast cancer is demonstrated.

Breast Cancer Arrays Ki67

This study included 498 patients with primary invasive breast cancer treated and diagnosed at the Malmo University Hospital between 1 Jan. 1988 and 31 Dec. 1992. The cases belonged to an original cohort of 512 patients. The median age at diagnosis was 65 years (range 27 to 96 years) and median follow-up time to first breast cancer event was 128 months (range 0 to 207 months). Information regarding the date of death was obtained from the regional cause-of-death registries for all patients. Complete treatment data were available for 379 (76%) patients, 160 of whom had received adjuvant tamoxifen. Information on adjuvant systemic chemotherapy was available for 382 patients, of which only 23 patients had received treatment. Two hundred patients received no adjuvant systemic treatment. Ethical permission was obtained from the Local Ethics Committee at Lund University (Dnr 613/02), whereby informed consent was deemed not to be required, but opting out was an option.

Tissue Microarray Construction

For the present study, new tissue microarrays (TMAs) were constructed as described above in Example 2. In brief, two 1.0 mm cores were taken from areas representative of invasive cancer and mounted in a recipient block using a manual arraying device (MTA-1, Beecher Inc, WI, USA).

Immunohistochemistry

As described previously, sections 4 μm in diameter were dried, deparaffinized, rehydrated and treated in a microwave for two rounds of five minutes in citrate buffer before being stained in a Techmate 500 (DAKO, Copenhagen, Denmark) with a polyclonal anti-Ki67 antibody.

For all other antibodies, heat-mediated antigen retrieval was performed using microwave treatment for two rounds of five minutes in a citrate buffer before being processed. Nuclear staining of Ki67 was assessed both as the fraction of positive cells (0 to 10%, 11 to 50% and 51 to 100%) and the staining intensity in the cytoplasm (negative=0, weak=1, moderate=2, strong=3).

Results

Autoscore was computed for each tissue core as the product of mean intensity of DAB positive tumour cells with the percent of positive stained tumor cells. Patients were grouped according to the manual score. The box plot of both the autoscore and the intensity shows an increase of the autoscore as the tumor get more aggressive (more proliferative), that correlate with manual analysis.

The results of the analyses are shown in FIGS. 14 and 15.

Figure 14A:
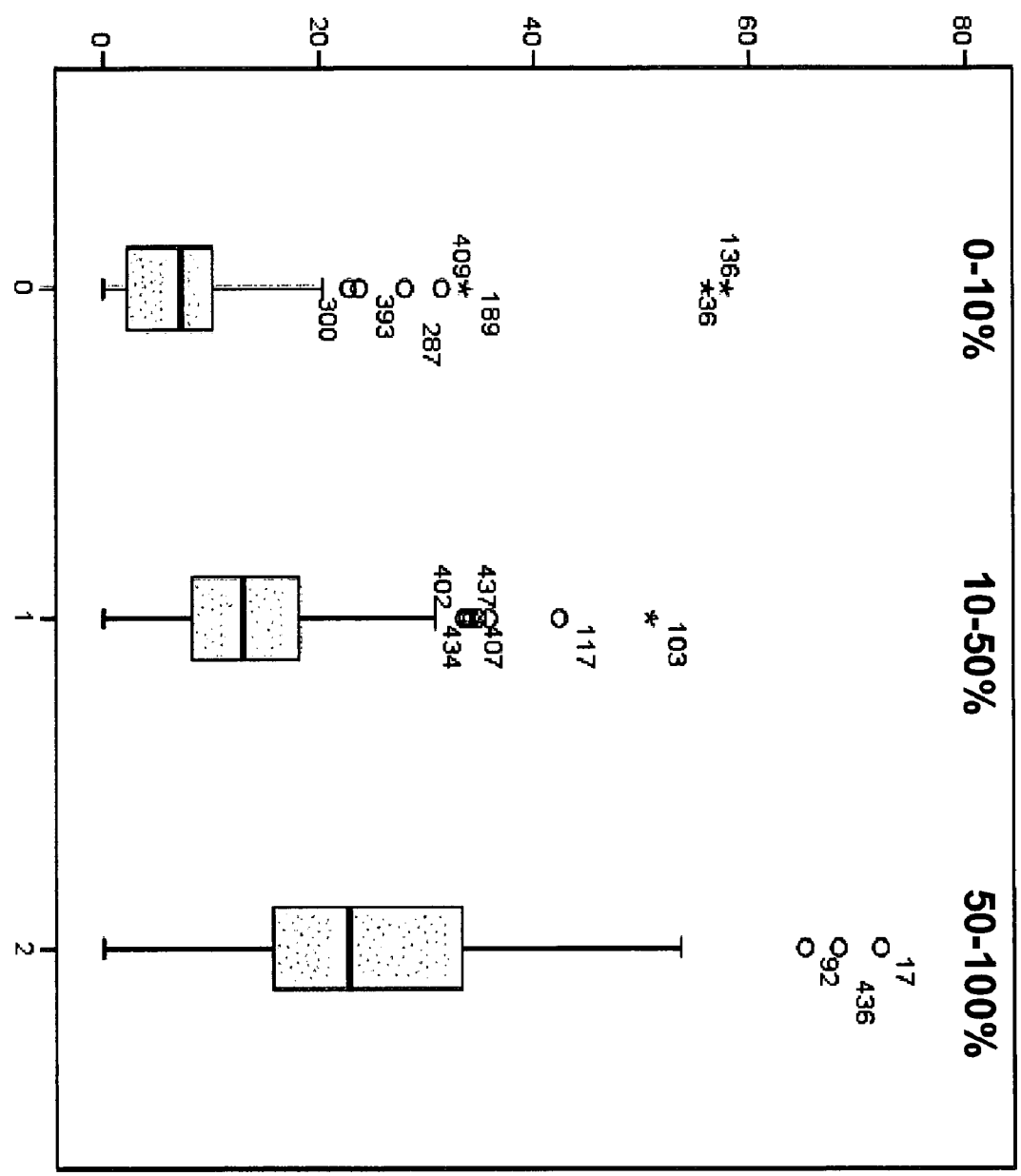
FIGS. 14A to 14F show the ccorrelation between manual and automated scoring for biomarker Ki67 in breast tumour tissue.
Figure 14B:
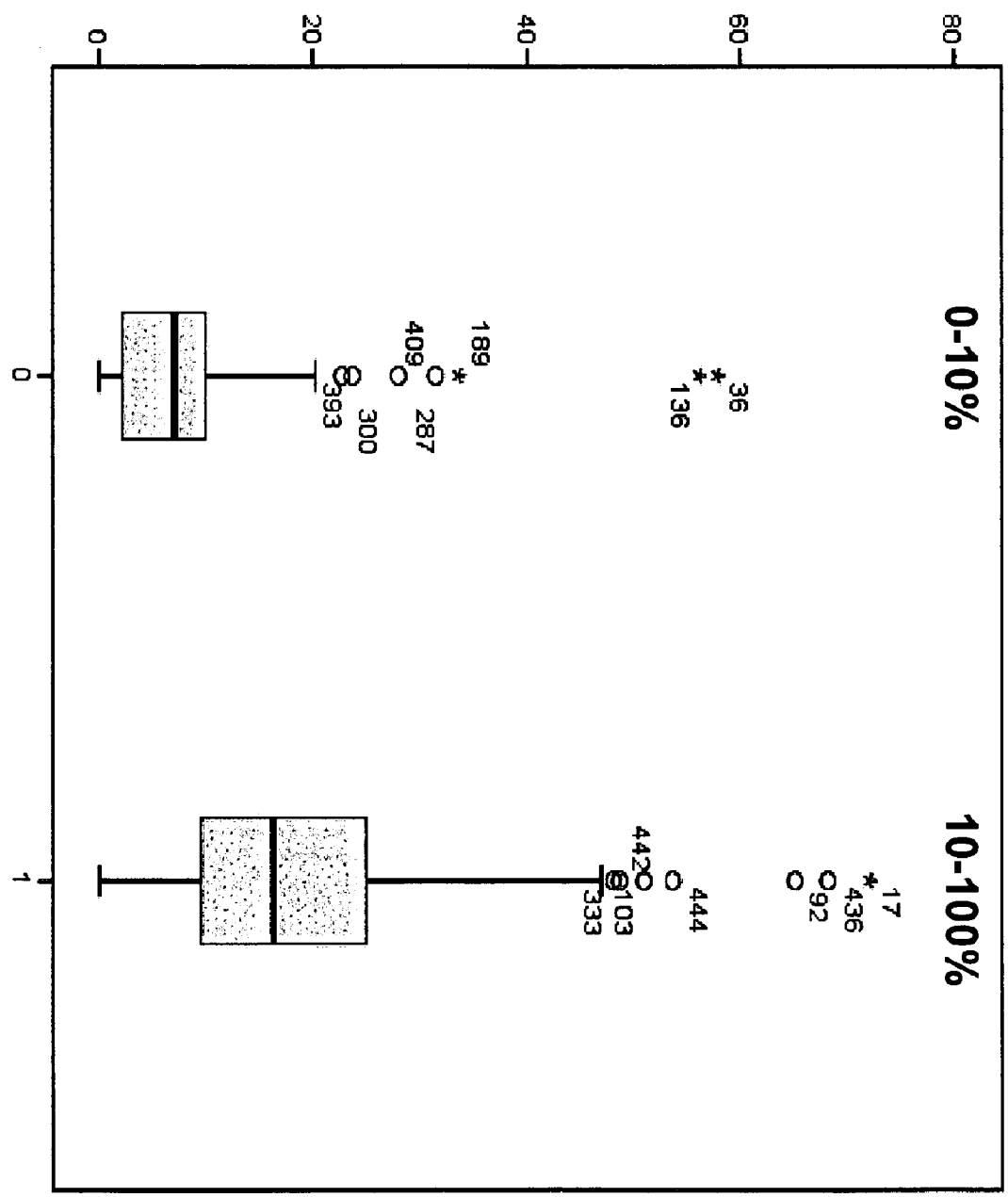
Figure 14C:
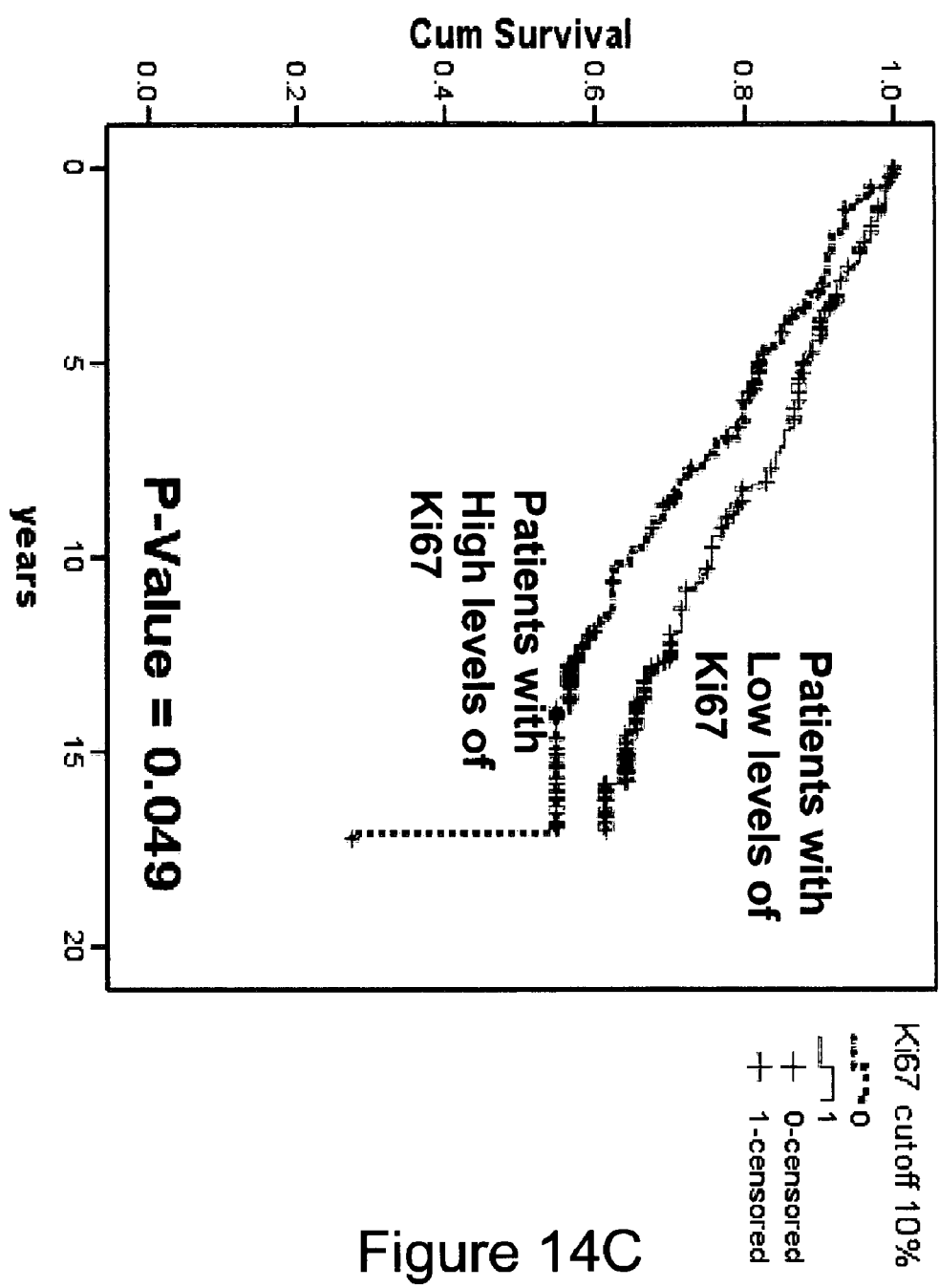
Figure 14D:
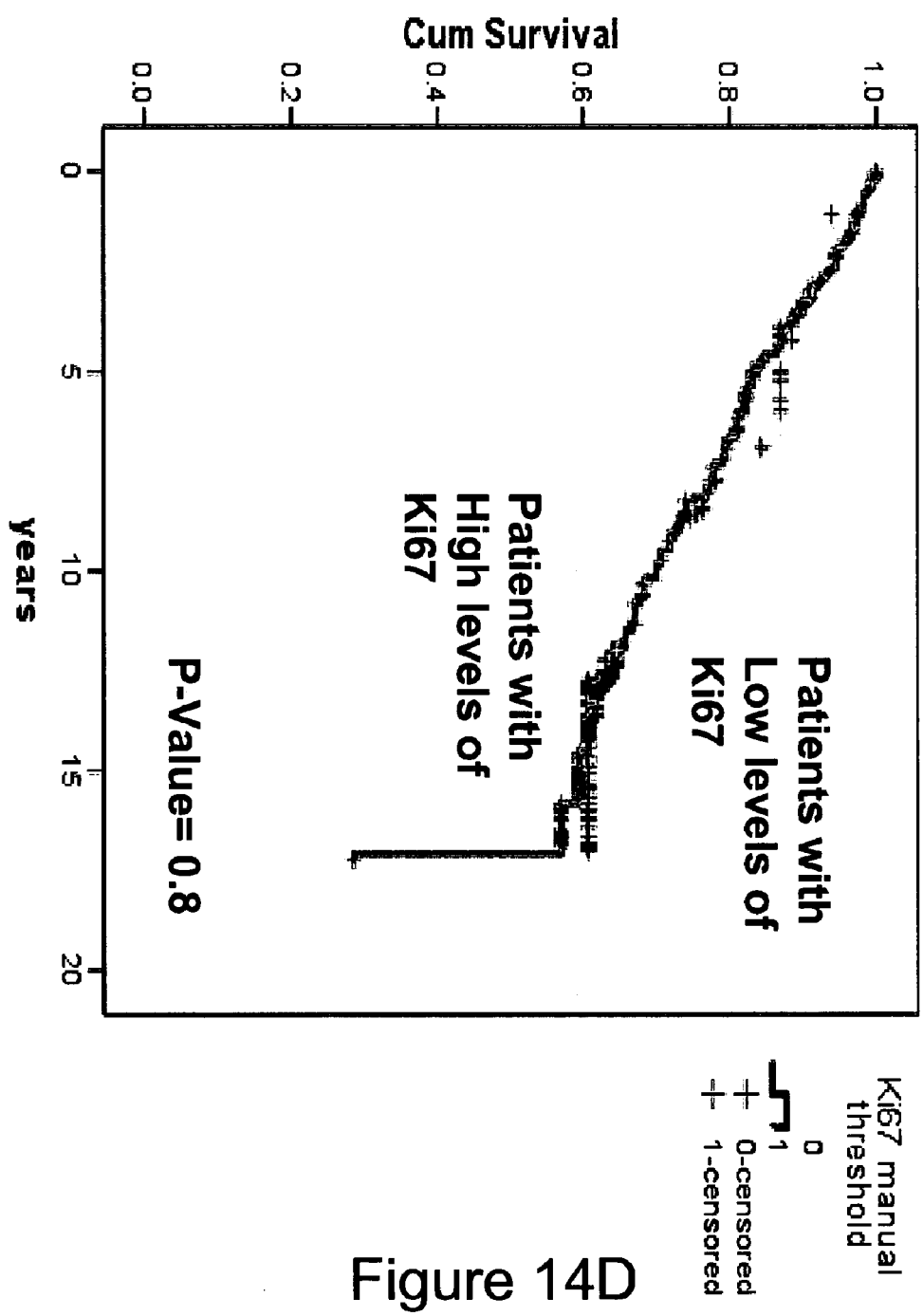
Figure 14E:
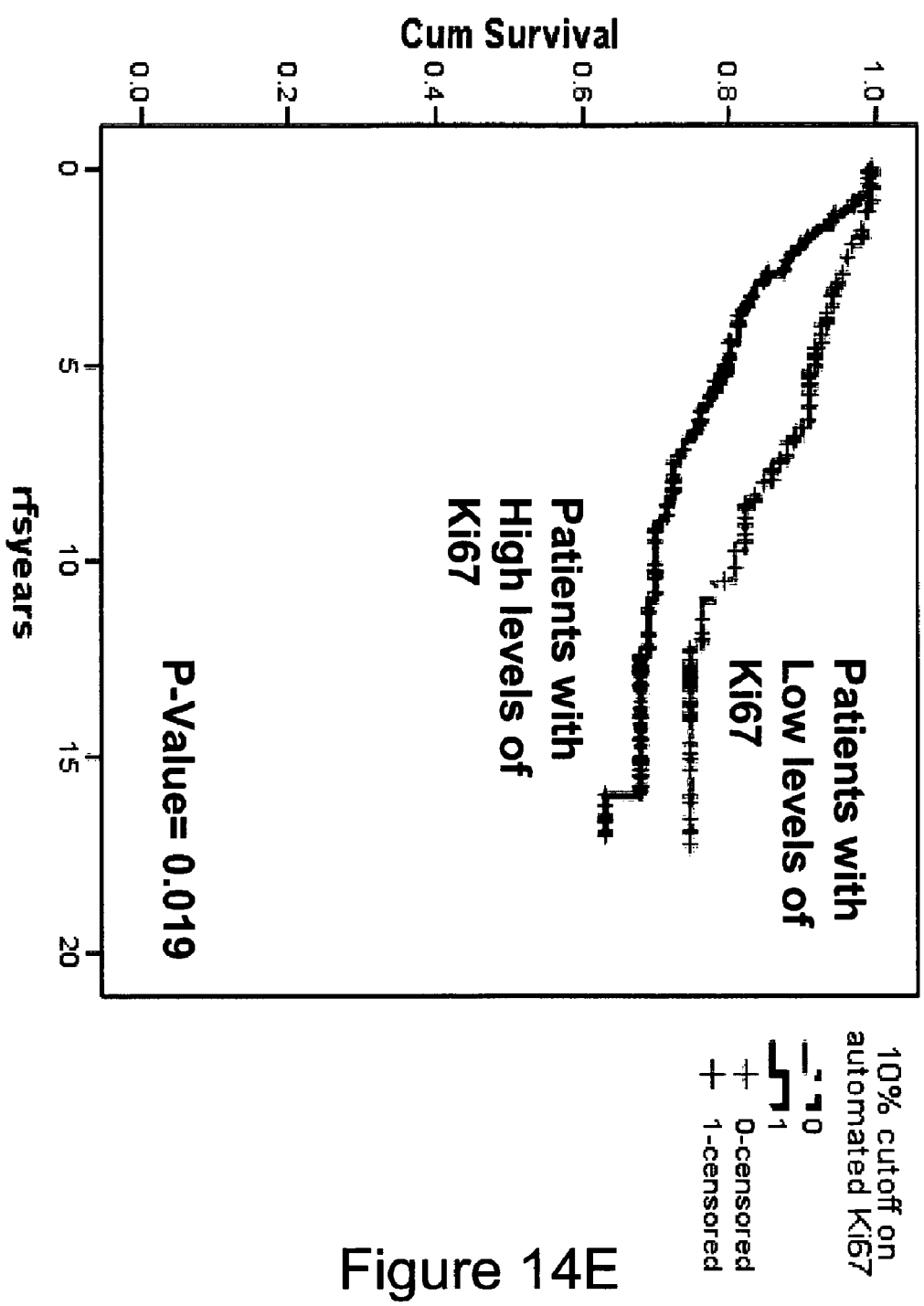
Figure 14F:
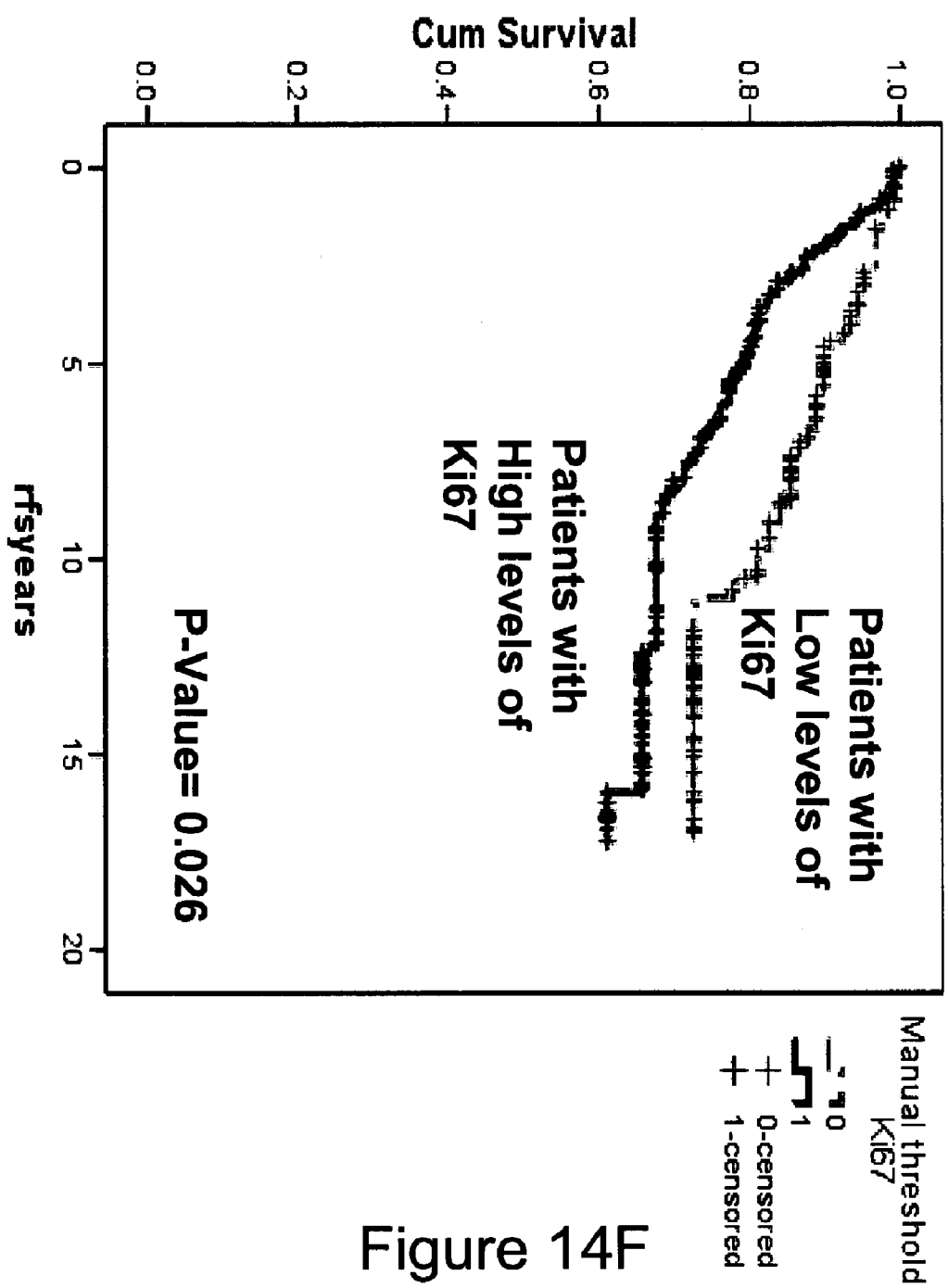
Figure 15A:
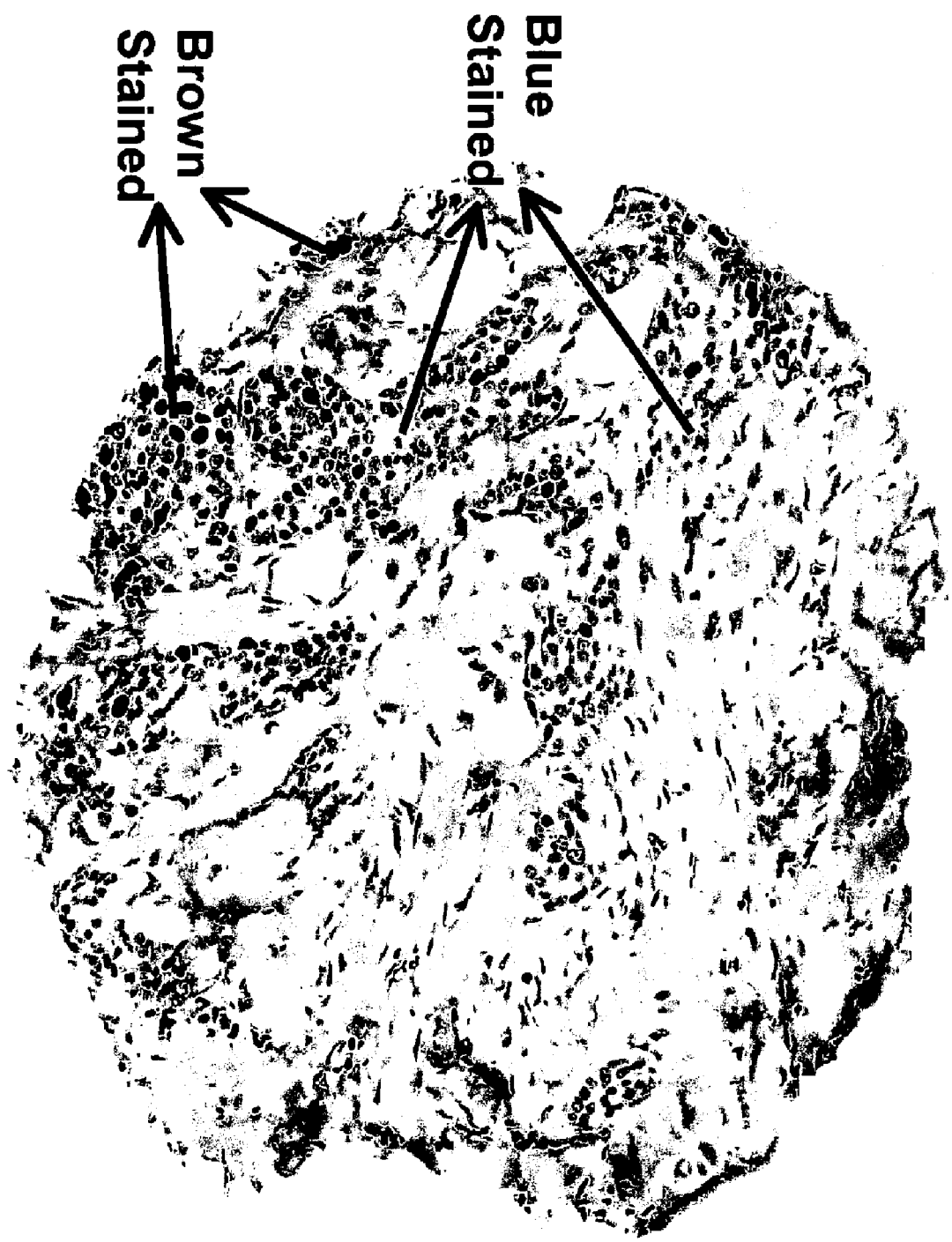
FIGS. 15A and 15B show images of a breast tissue core marked for biomarker Ki67 and DAB stained.
Figure 15B:
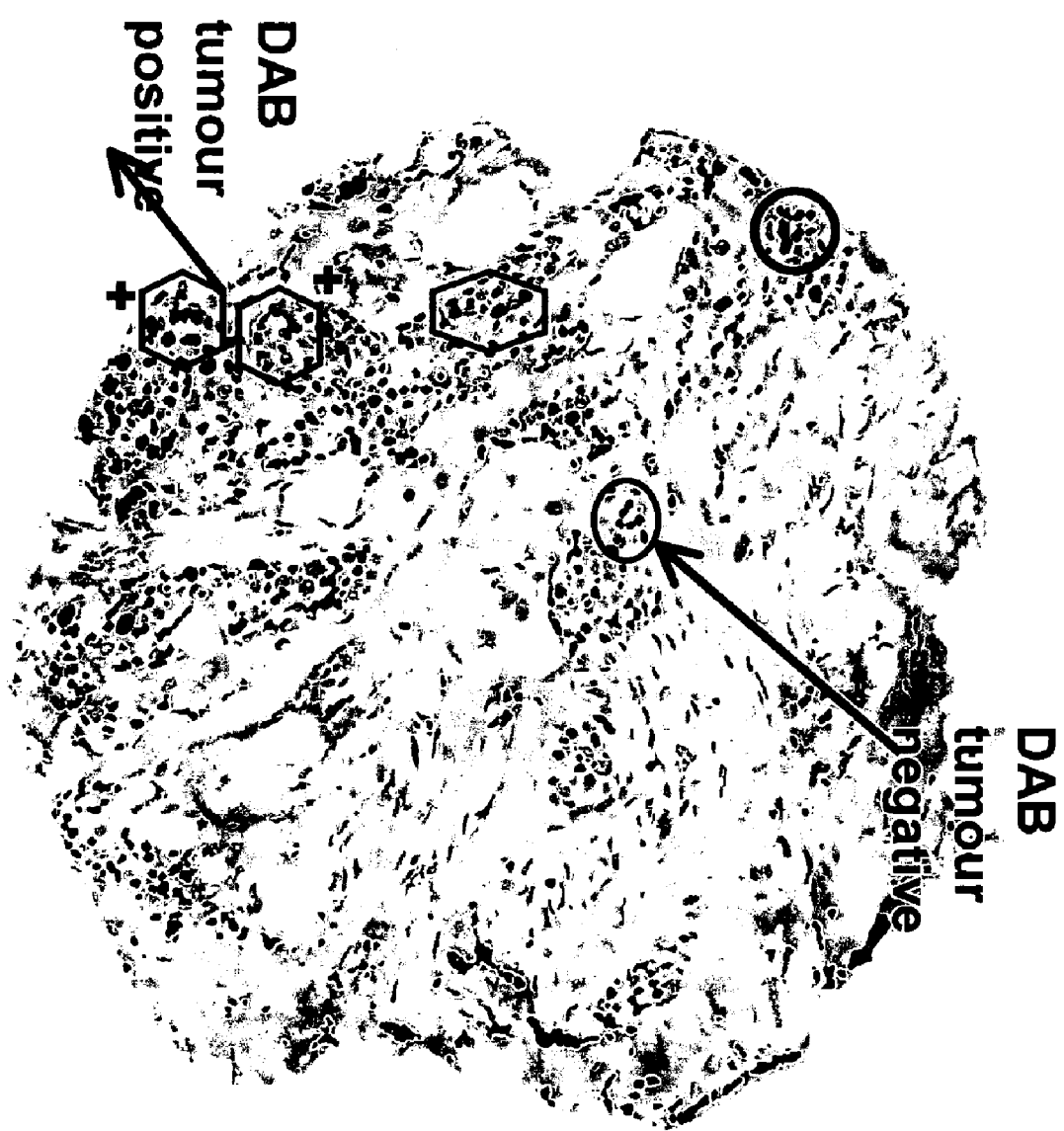

FIG. 14A shows the distribution of the automated scores within the manual scores as defined by the pathologist. FIG. 14B shows the distribution of the automated scores within the manual scores as defined by the pathologist if either positive or negative. FIG. 14C shows breast cancer specific (BCS) survival functions from Kaplan-Meier analysis for patients with negative Ki67 status and positive Ki67 status as defined by tresholding at 10% the automated Ki67 output. FIG. 14D shows BCS survival functions from Kaplan-Meier analysis for patients with negative Ki67 status and positive Ki67 status as they were manually defined by the pathologist. FIG. 14E shows recurrence free survival (RFS) survival functions from Kaplan-Meier analysis for patients with negative Ki67 status and positive Ki67 status as defined by thresholding at 10% the automated Ki67 output. FIG. 14F shows RFS survival functions from Kaplan-Meier analysis for patients with negative Ki67 status and positive Ki67 status as they were manually defined by the pathologist. FIG. 15A shows image of a breast tissue core marked for biomarker Ki67 and DAB stained with annotated areas of DAB negative (labelled blue) and DAB positive (labelled brown) tumour patterns. FIG. 15B shows areas of demarked positive DAB tumour (which are red) and negative tumour areas not expressing Ki67 shown demarked (which are blue).

Furthermore our findings shows that thresholding of the automated continuous output of Ki67 quantification shows a good correlation with manual pathologist binary (either positive or negative) annotations. Kaplan-Meier analysis of survival show similar survival trends for patients with high and low level of Ki67.

Breast Cancer Arrays p53

Samples from two hundred ninety-nine consecutive primary invasive breast cancer patients seen at CCF between 1995 and 1996 were arrayed on a single tissue array. A duplicate block was constructed using independent cores from the same patient set. Each tissue array patient had a 5-year clinical follow-up information. Tissue arrays were stained using monoclonal antibodies targeting p53. Nuclear staining of p53 was assessed both as the fraction of positive cells (0 to 10%, 11 to 50% and 51 to 100%) and the staining intensity in the cytoplasm (negative=0, weak=1, moderate=2, strong=3).

The results of our analyses are shown in FIG. 13. With reference to FIGS. 13A to F, the level of expression for the p53 biomarker was manually quantified as being "weak", "moderate" or "strong expression" by a pathologist. FIG. 13A shows an image of a breast tissue core marked for p53 and DAB stained, showing "weak" patterns, annotated areas of DAB negative (labelled blue) and DAB positive (labelled brown) tumour patterns. FIG. 13B shows areas of positive DAB tumour (demarked positive areas are red) and tumour areas not expressing p53 (demarked negatives are blue). FIG. 13C shows an image of a breast tissue core marked for p53, showing "moderate" patterns, with annotated areas of DAB negative (labelled blue) and DAB positive (labelled brown) tumour patterns. FIG. 13D shows areas of demarked positive DAB tumour (which are red) and negative tumour areas not expressing p53 shown demarked (which are blue). FIG. 13E shows an image of a breast tissue core marked for p53, showing "strong" patterns, with annotated areas of DAB negative (labelled blue) and DAB positive (labelled brown) tumour patterns. FIG. 13F shows areas of demarked positive DAB tumour areas (which are red) and negative tumour areas not expressing p53 shown demarked (which are blue).

The spearman correlation test was used to test the correlation between manual and automated scores. After comparing the automated scores with the manual pathologist based scores we observed an excellent index of correlation (correlation coefficient 0.8).

All publications mentioned in the above specification, and references cited in said publications, are herein incorporated by reference. Various modifications and variations of the described methods and system of the present invention will be apparent to those skilled in the art without departing from the scope and spirit of the present invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

REFERENCES

1. Conneely, O M, Jericevic, B M, and Lydon, J P. Progesterone receptors in mammary gland development and tumourigenesis. J Mammary Gland Biol Neoplasia, 2003. 8: 205-14.
2. Ryden, L, Linderholm, B, Nielsen, N H, Emdin, S, Jonsson, P E, and Landberg, G. Tumour specific VEGF-A and VEGFR2/KDR protein are co-expressed in breast cancer. Breast Cancer Res Treat, 2003. 82: 147-54.
3. Beatson, G. On the treatment of inoperable cases of carcinoma of the mamma: suggestions for a new method of treatment with illustrative cases. Lancet, 1896. 2: 104-107.
4. Bonadonna, G, Brusamolino, E, Valagussa, P, Rossi, A, Brugnatelli, L, Brambilla, C, De Lena, M, Tancini, G, Bajetta, E, Musumeci, R, and Veronesi, U. Combination chemotherapy as an adjuvant treatment in operable breast cancer. N Engl J Med, 1976. 294: 405-10.
5. Pagani, O, O'Neill, A, Castiglione, M, Gelber, R D, Goldhirsch, A, Rudenstam, C M, Lindtner, J, Collins, J, Crivellari, D, Coates, A, Cavalli, F, Thurlimann, B, Simoncini, E, Fey, M, Price, K, and Senn, H J. Prognostic impact of amenorrhoea after adjuvant chemotherapy in premenopausal breast cancer patients with axillary node involvement: results of the International Breast Cancer Study Group (IBCSG) Trial VI. Eur J Cancer, 1998. 34: 632-40.
6. EBCTG. Effects of chemotherapy and hormonal therapy for early breast cancer on recurrence and 15-year survival: an overview of the randomised trials. Lancet, 2005. 365: 1687-717.
7. Shang, Y. and Brown, M. Molecular determinants for the tissue specificity of SERMs. Science, 2002. 295: 2465-8.
8. Emens, L A and Davidson, N E. Adjuvant hormonal therapy for premenopausal women with breast cancer. Clin Cancer Res, 2003. 9: 486S-94S.
9. Rutqvist, L E. Adjuvant endocrine therapy. Best Pract Res Clin Endocrinol Metab, 2004. 18: 81-95.
10. Goldhirsch, A, Wood, W C, Gelber, R D, Coates, A S, Thurlimann, B, and Senn, H J. Meeting highlights: updated international expert consensus on the primary therapy of early breast cancer. 2003. 21: 3357-65.
11. Coombes, R C, Hall, E, Gibson, L J, Paridaens, R, Jassem, J, Delozier, T, Jones, S E, Alvarez, I, Bertelli, G, Ortmann, O, Coates, A S, Bajetta, E, Dodwell, D, Coleman, R E, Fallowfield, L J, Mickiewicz, E, Andersen, J, Lonning, P E, Cocconi, G, Stewart, A, Stuart, N, Snowdon, C F, Carpentieri, M, Massimini, G, Bliss, J M, and van de Velde, C. A randomized trial of exemestane after two to three years of tamoxifen therapy in postmenopausal women with primary breast cancer. N Engl J Med, 2004. 350: 1081-92.
12. Howell, A, Cuzick, J, Baum, M, Buzdar, A, Dowsett, M, Forbes, J F, Hoctin-Boes, G, Houghton, J, Locker, G Y, and Tobias, J S. Results of the ATAC (Arimidex, Tamoxifen, Alone or in Combination) trial after completion of 5 years' adjuvant treatment for breast cancer. Lancet, 2005. 365: 60-2.
13. Goldhirsch, A, Glick, J H, Gelber, R D, Coates, A S, Thurlimann, B, and Senn, H J. Meeting highlights: international expert consensus on the primary therapy of early breast cancer 2005. Ann Oncol, 2005. 16: 1569-83.
14. McCarty, K S, Jr., Miller, L S, Cox, E B, Konrath, J, and McCarty, K S, Sr. Estrogen receptor analyses. Correlation of biochemical and immunohistochemical methods using monoclonal antireceptor antibodies. Arch Pathol Lab Med, 1985. 109: 716-21.
15. Reiner, A, Neumeister, B, Spona, J, Reiner, G, Schemper, M, and Jakesz, R. Immunocytochemical localization of estrogen and progesterone receptor and prognosis in human primary breast cancer. Cancer Res, 1990. 50: 7057-61.
16. Barnes, D M, Harris, W H, Smith, P, Millis, R R, and Rubens, R D. Immunohistochemical determination of oestrogen receptor: comparison of different methods of assessment of staining and correlation with clinical outcome of breast cancer patients. Br J Cancer, 1996. 74: 1445-51.
17. Fisher, E R, Anderson, S, Dean, S, Dabbs, D, Fisher, B, Siderits, R, Pritchard, J, Pereira, T, Geyer, C, and Wolmark, N. Solving the dilemma of the immunohistochemical and other methods used for scoring estrogen receptor and progesterone receptor in patients with invasive breast carcinoma. Cancer, 2005. 103: 164-73.
18. Rudiger, T, Hofler, H, Kreipe, H H, Nizze, H, Pfeifer, U, Stein, H, Dallenbach, FE, Fischer, H P, Mengel, M, von Wasielewski, R, and Muller-Hermelink, H K. Quality assurance in immunohistochemistry: results of an interlaboratory trial involving 172 pathologists. Am J Surg Pathol, 2002. 26: 873-82.
19. Cross, S S. Observer accuracy in estimating proportions in images: implications for the semiquantitative assessment of staining reactions and a proposal for a new system. J Clin Pathol, 2001. 54: 385-90.
20. Lehr, H A, Jacobs, T W, Yaziji, H, Schnitt, S J, and Gown, A M. Quantitative evaluation of HER-2/neu status in breast cancer by fluorescence in situ hybridization and by immunohistochemistry with image analysis. Am J Clin Pathol, 2001. 115: 814-22.
21. Umemura, S, Itoh, J, Itoh, H, Serizawa, A, Saito, Y, Suzuki, Y, Tokuda, Y, Tajima, T, and Osamura, R Y. Immunohistochemical evaluation of hormone receptors in breast cancer: which scoring system is suitable for highly sensitive procedures? Appl Immunohistochem Mol Morphol, 2004. 12: 8-13.
22. Brennan, D J, Kelly, C, Rexhepaj E, Dervan, P A, Duffy, M J, and Gallagher, W M. Contribution of DNA and Tissue Microarray Technology to the Identification and Validation of Biomarkers and Personalised Medicine in Breast Cancer. Cancer Genomics and Proteomics, 2007. 4: 3-16.
23. Ryden, L, Jirstrom, K, Bendahl, P O, Ferno, M, Nordenskjold, B, Stal, O, Thorstenson, S, Jonsson, PE, and Landberg, G. Tumour-specific expression of vascular endothelial growth factor receptor 2 but not vascular endothelial growth factor or human epidermal growth factor receptor 2 is associated with impaired response to adjuvant tamoxifen in premenopausal breast cancer. 2005. 23: 4695-704.
24. Ryden, L, Jonsson, P E, Chebil, G, Dufmats, M, Ferno, M, Jirstrom, K, Kallstrom, A C, Landberg, G, Stal, O, Thorstenson, S, and Nordenskjold, B. Two years of adjuvant tamoxifen in premenopausal patients with breast cancer: a randomised, controlled trial with long-term follow-up. 2005. 41: 256-64.
25. O'Brien, S, Fagan, A, Fox, E, Millikan, R, Culhane, A, Brennan, D, McCann, A, Hegarty, S, Moyna, S, Duffy, M, Higgins, D, Jirstrom, K, Landberg, G, and Gallagher, W. CENP-F expression is associated with poor prognosis and chromosomal instability in patients with primary breast cancer. Int J Cancer, 2007. 120: 1434-43.
26. Shi, T, Seligson, D, Belldegrun, A S, Palotie, A, and Horvath, S. Tumour classification by tissue microarray profiling: random forest clustering applied to renal cell carcinoma. Mod Pathol, 2005. 18: 547-57.
27. Seligson, D B, Horvath, S, Shi, T, Yu, H, Tze, S, Grunstein, M, and Kurdistani, S K. Global histone modification patterns predict risk of prostate cancer recurrence. Nature, 2005. 435: 1262-6.
28. Kononen, J, Bubendorf, L, Kallioniemi, A, Barlund, M, Schraml, P, Leighton, S, Torhorst, J, Mihatsch, M J, Sauter, G, and Kallioniemi, O P. Tissue microarrays for high-throughput molecular profiling of tumour specimens. Nat Med, 1998. 4: 844-7.
29. Braunschweig, T, Chung, J Y, and Hewitt, S M. Tissue microarrays: bridging the gap between research and the clinic. Expert Rev Proteomics, 2005. 2: 325-36.
30. Coons, A C, Jones, R N. Immunological properties of an antibody containing a fluorescent group. Proc Soc Exp Biol Med, 1941. 47: 200-202.
31. Camp, R L, Chung, G G, and Rimm, D L. Automated subcellular localization and quantification of protein expression in tissue microarrays. Nat Med, 2002. 8: 1323-7.
32. Fernandez, D C, Bhargava, R, Hewitt, S M, and Levin, I W. Infrared spectroscopic imaging for histopathologic recognition. Nat Biotechnol, 2005. 23: 469-74.

The invention claimed is:

1. A method for the analysis of an image of a biological sample comprising one or more candidate objects of interest comprising the steps of:
  (a) obtaining a digitised image of the biological sample;
  (b) separating the image of the biological sample into a First Image and a Second Image, the separating step comprising;
     (i) defining a first threshold for hue saturation intensity and three colour stains (RGB colour space) properties of a first optical enhancer and using the first threshold properties in the digitised image to produce the First Image comprising the background and the three colour stains (RGB colour space) information of the first optical enhancer and
     (ii) defining a second threshold for hue saturation intensity and three colour stains (RGB colour space) properties of a second optical enhancer and using the second threshold properties in the digitised image to produce the Second Image comprising the background and the three colour stains (RGB colour space) information of the second optical enhancer;
  (c) assimilating the morphological features or morphological pattern of the one or more candidate objects of interest in the First Image, the assimilating step comprising processing the First Image by conducing colour space transformation to convert the three colour stains (RGB colour space) information to a perceptually uniform colour space followed by a segmentation step comprising firstly conducting colour demarcation and secondly conducting watershed segmentation to create a 3D view of the candidate objects of interest from which the morphological features or morphological pattern are measured;
  (d) applying to the Second Image the morphological features or morphological pattern assimilated from the First Image by matching the morphological features or morphological pattern assimilated from the First Image with morphological features or morphological pattern in the Second Image;

(e) eliminating from the Second Image objects with non-matching morphological features or non-matching morphological pattern with the one or more candidate objects of interest in the First Image; and (f) quantitating the level of expression of the one or more candidate objects of interest in the First Image using the matching morphological features or morphological pattern of the one or more candidate objects in the First Image and the Second Image.

2. The method according to claim 1, wherein the Second Image is optically enhanced by processing the Second Image by conducting colour space transformation to convert the three colour stains (RGB colour space) information to a perceptually uniform colour space followed by a segmentation step comprising firstly conducting colour demarcation and secondly conducting watershed segmentation to create a 3D view of the candidate objects of interest from which the morphological features or morphological pattern are measured.

3. The method of claim 2, wherein the morphological pattern comprises a spatially adjacent group of one or more candidate objects of interest in the First Image and said pattern is assimilated by measuring the distance between the candidate objects of interest and then grouping the candidate objects of interest into at least a first spatially adjacent group and a second spatially distant group such that the mean distance between and the mean area encompassed by the candidate objects of interest in the one or more spatially adjacent group represents a candidate positive group.

4. The method of claim 2, wherein the morphological features or morphological pattern of the one or more candidate objects of interest in the First Image is assimilated by measuring morphological characteristics of the candidate objects of interest and then grouping the candidate objects of interest according to the measured morphological characteristics to form one or more candidate positive groups.

5. The method of claim 3 or 4, wherein the morphological features or morphological pattern of the one or more candidate positive groups in the First Image is matched with the same morphological features or morphological pattern of the one or more candidate objects of interest in the Second Image to form one or more candidate negative groups in the Second Image.

6. The method of claim 5, further comprising the step of eliminating from the Second Image objects with morphological features or morphological pattern which do not match with the one or more candidate positive groups.

7. A non-transitory computer readable medium encoded with a computer program that when loaded and executed by a computer causes the computer to perform the method according to claim 1.

8. An apparatus for quantification of one or more candidate objects of interest in a biological sample including
(a) means for obtaining a digitised image of the biological sample;
(b) means for separating the image of the biological samples into a First Image and a Second Image, the separating means comprising:
  (i) means for defining a first threshold for hue saturation intensity and three colour stains (RGB colour space) properties of a first optical enhancer and using the first threshold properties in the digitised image to produce the First Image comprising the background and the three colour stains (RGB colour space) information of the first optical enhancer and
  (ii) means for defining a second threshold for hue saturation intensity and three colour stains (RGB colour space) properties of a second optical enhancer and using the second threshold properties in the digitised image to produce the Second Image comprising the background and the three colour stains (RGB colour space) information of the second optical enhancer;
(c) means for assimilating morphological features or morphological pattern of the one or more candidate objects of interest in the First Image, the assimilating means comprising means for processing the First Image by conducing colour space transformation to convert the three colour stains (RGB colour space) information to a perceptually uniform colour space and means for segmentation comprising means for firstly conducting colour demarcation and secondly conducting watershed segmentation to create a 3D view of the candidate objects of interest from which the morphological features or morphological pattern are measured;
(d) means for applying to the Second Image the morphological features or morphological pattern assimilated from the First Image comprising means for matching the morphological features or morphological pattern assimilated from the First Image with morphological features or morphological pattern in the Second Image;
(e) means for eliminating from the Second Image objects with non-matching morphological features or non-matching morphological patterns with the one or more candidate objects of interest in the First Image; and
(f) means for quantitating the level of expression of the one or more candidate objects of interest in the First Image using the matching morphological features or morphological patterns of the one or more candidate objects in the First Image and the Second Image.

9. A system for quantification of one or more candidate object of interest in a biological sample comprising:
(a) means for obtaining a digitised image of the biological sample;
(b) means for separating an image of a biological sample into a First Image and a Second Image, the separating means comprising:
  (i) means for defining a first threshold for hue saturation intensity and three colour stains (RGB colour space) properties of a first optical enhancer and using the first threshold properties in the digitised image to produce the First Image comprising the background and the three colour stains (RGB colour space) information of the first optical enhancer and
  (ii) means for defining a second threshold for hue saturation intensity and three colour stains (RGB colour space) properties of a second optical enhancer and using the second threshold properties in the digitised image to produce the Second Image comprising the background and the three colour stains (RGB colour space) information of the second optical enhancer;
(c) means for assimilating morphological features or morphological pattern of the one or more candidate objects of interest in the First Image, the assimilating means comprising means for processing the First Image by conducing colour space transformation to convert the three colour stains (RGB colour space) information to a perceptually uniform colour space and means for segmentation comprising means for firstly conducting colour demarcation and secondly conducting watershed segmentation to create a 3D view of the candidate objects of interest from which the morphological features or morphological pattern are measured;

(d) means for applying to the Second Image the morphological features or morphological pattern assimilated from the First Image, comprising means for matching the morphological features or morphological pattern assimilated from the First Image with morphological features or morphological pattern in the Second Image;

(e) means for eliminating from the Second Image objects with non-matching morphological features or non-matching morphological patterns with the one or more candidate objects of interest in the First Image; and (f) means for quantitating the level of expression of the one or more candidate objects of interest in the First Image using the matching morphological features or morphological patterns of the one or more candidate objects in the First Image and the Second Image.

10. The system of claim 9, which is a computer implemented system.

11. A method for determining the level of expression of one or more candidate objects of interest in a biological sample, wherein the method comprises immunohistochemically staining the biological sample; and (a) obtaining a digitised image of the biological sample;

(b) separating the image of the biological sample into a First Image and a Second Image the separating step comprising:

(i) defining a first threshold for hue saturation intensity and three colour stains (RGB colour space) properties of a first optical enhancer and using the first threshold properties in the digitised image to produce the First Image comprising the background and the three colour stains (RGB colour space) information of the first optical enhancer and (ii) defining a second threshold for hue saturation intensity and three colour stains (RGB colour space) properties of a second optical enhancer and using the second threshold properties in the digitised image to produce the Second Image comprising the background and the three colour stains (RGB colour space) information of the second optical enhancer;

(c) assimilating the relevant morphological features or morphological pattern of the one or more candidate objects of interest in the First Image, the assimilating step comprising processing the First Image by conducting colour space transformation to convert the three colour stains (RGB colour space) information to a perceptually uniform colour space followed by a segmentation step comprising firstly conducting colour demarcation and secondly conducting watershed segmentation to create a 3D view of the candidate objects of interest from which the morphological features or morphological pattern are measured;

(d) applying to the Second Image the morphological features or morphological pattern assimilated from the First Image by matching the morphological features or morphological pattern assimilated from the First Image with morphological features or morphological pattern in the Second Image;

(e) eliminating from the Second Image objects with non-matching morphological features or non-matching morphological patterns with the one or more candidate objects of interest in the First Image; and (f) quantitating the level of expression of the one or more candidate objects or areas of interest in the First Image using the matching morphological features or morphological patterns of the one or more candidate objects in the First Image and the Second Image.

12. The method of claim 11, wherein the one or more candidate objects of interest is/are expressed in tumour cells.

13. The method of claim 11, wherein the one or more candidate objects of interest is/are expressed in a nucleus of a tumour cell.

14. The method of claim 11, wherein the one or more candidate objects of interest is/are selected from the group consisting of an Estrogen Receptor (ER) and a Progesterone Receptor (PR).

15. The method of claim 11, wherein the image of the biological sample is obtained by scanning the biological sample.

* * * * *